United States Patent
Adlem et al.

(10) Patent No.: US 10,343,982 B2
(45) Date of Patent: *Jul. 9, 2019

(54) COMPOUNDS AND MESOGENIC MEDIA

(71) Applicant: MERCK PATENT GMBH, Darmstadt (DE)

(72) Inventors: Kevin Adlem, Bournemouth (GB); Owain Llyr Parri, Ringwood (GB)

(73) Assignee: MERCK PATENT GMBH, Darmstadt (DE)

(*) Notice: Subject to any disclaimer, the term of this patent is extended or adjusted under 35 U.S.C. 154(b) by 0 days.

This patent is subject to a terminal disclaimer.

(21) Appl. No.: 15/024,066

(22) PCT Filed: Sep. 8, 2014

(86) PCT No.: PCT/EP2014/002430
§ 371 (c)(1),
(2) Date: Mar. 23, 2016

(87) PCT Pub. No.: WO2015/043713
PCT Pub. Date: Apr. 2, 2015

(65) Prior Publication Data
US 2016/0229795 A1    Aug. 11, 2016

(30) Foreign Application Priority Data
Sep. 25, 2013  (EP) .................. 13004656

(51) Int. Cl.
| C09K 19/00 | (2006.01) |
| C07C 255/57 | (2006.01) |
| C09K 19/02 | (2006.01) |
| C07C 25/18 | (2006.01) |
| C07C 255/51 | (2006.01) |
| C07C 255/54 | (2006.01) |
| C09K 19/20 | (2006.01) |
| C09K 19/58 | (2006.01) |
| C09K 19/04 | (2006.01) |

(52) U.S. Cl.
CPC ............ *C07C 255/57* (2013.01); *C07C 25/18* (2013.01); *C07C 255/51* (2013.01); *C07C 255/54* (2013.01); *C09K 19/0258* (2013.01); *C09K 19/2007* (2013.01); *C09K 19/588* (2013.01); *C09K 2019/0444* (2013.01)

(58) Field of Classification Search
CPC ................................................ C09K 19/0258
See application file for complete search history.

(56) References Cited

U.S. PATENT DOCUMENTS

| 2,196,576 A * | 4/1940 | Coleman ............. C07C 43/2055 568/643 |
| 5,576,338 A * | 11/1996 | Friesen ................ C07D 217/04 514/337 |
| 2010/0197659 A1* | 8/2010 | Dierks ................ A61K 31/165 514/211.15 |
| 2015/0315470 A1* | 11/2015 | Adlem ............... C09K 19/0258 252/299.65 |

FOREIGN PATENT DOCUMENTS

| CN | 102617304 A | 8/2012 | |
| GB | 2356629 A * | 5/2001 | ............ C09K 19/02 |
| JP | H02-255635 | 10/1990 | |

OTHER PUBLICATIONS

Buchecker et al., "Some studies on liquid crystals incorporating three membered linking units combined with 1,3 linked rings", Jun. 1996, Liquid Crystals, vol. 20 Issue 6, 811-814.*
Fergusson et al. "The dramatic influence of the location of bend and of lateral fluoro substitution on the mesomorphic properties of angular chiral esters based on a 1,3-disubstituted benzene ring", Feb. 22, 2010, Journal of Materials Chemistry, 20, 3069-3078. (Year: 2010).*
International Search Report and Written Opinion from PCT/EP2014/002430 dated Oct. 31, 2014.
Notification of Reasons for Refusal (1st Office Action) corresponding to Japanese Application No. 2016-516864—Drafting Date: May 23, 2018—Dispatching Date: May 30, 2018.
Buchecker, Richard, et al., "Some Studies on Liquid Crystals Incorporating Three Membered Linking Units Combined With 1,3 Lnked Rings", Liquid Crystals, 1996, 20(6), 811-814.
Photinos, Demetri J. et al., Molecular Flexibility in Nematics: From Alkanes to Dimer Mesogens, Journal of the Chemical Society, Faraday Transactions, 1992, 88(13), 1875-83.
Griffin, Anselm C., et al., Effect of Molecular Structure on Mesomorphism:14. Difluorinated Siamese Twin Mesogens, Liquid Crystals and Ordered Fluids, 1984, 4, 1077-87.
Ciogli, Alessia et al., Enantiomerization of Chiral Uranyl-Salophen Complexes via Unprecedented Ligand Hemilability: Toward Configurationally Stable Derivatives, Journal of Organic Chemistry, 2008, 73(16), 6108-6118.

* cited by examiner

*Primary Examiner* — Chanceity N Robinson
(74) *Attorney, Agent, or Firm* — Millen White Zelano and Branigan, PC; Csaba Henter

(57) ABSTRACT

Disclosed are compounds of formula I

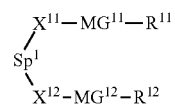

the use of compounds of formula I in liquid crystal media and in particular to flexoelectric liquid crystal devices containing the liquid crystal media.

20 Claims, No Drawings

COMPOUNDS AND MESOGENIC MEDIA

The invention relates to compounds of formula I

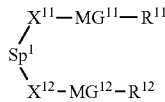

wherein $R^{11}$, $R^{12}$, $MG^{11}$, $MG^{12}$ and $Sp^1$ have the meaning given herein below, which are preferably bimesogenic compounds, to the use of compounds of formula I in liquid crystal media and particular to flexoelectric liquid crystal devices comprising a liquid crystal medium according to the present invention.

Liquid Crystal Displays (LCDs) are widely used to display information. LCDs are used for direct view displays, as well as for projection type displays. The electro-optical mode which is employed for most displays still is the twisted nematic (TN)-mode with its various modifications. Besides this mode, the super twisted nematic (STN)-mode and more recently the optically compensated bend (OCB)-mode and the electrically controlled birefringence (ECB)-mode with their various modifications, as e.g. the vertically aligned nematic (VAN), the patterned ITO vertically aligned nematic (PVA)-, the polymer stabilized vertically aligned nematic (PSVA)-mode and the multi domain vertically aligned nematic (MVA)-mode, as well as others, have been increasingly used. All these modes use an electrical field, which is substantially perpendicular to the substrates, respectively to the liquid crystal layer. Besides these modes there are also electro-optical modes employing an electrical field substantially parallel to the substrates, respectively the liquid crystal layer, like e.g. the In Plane Switching (short IPS) mode (as disclosed e.g. in DE 40 00 451 and EP 0 588 568) and the Fringe Field Switching (FFS) mode. Especially the latter mentioned electro-optical modes, which have good viewing angle properties and improved response times, are increasingly used for LCDs for modern desktop monitors and even for displays for TV and for multimedia applications and thus are competing with the TN-LCDs.

Further to these displays, new display modes using cholesteric liquid crystals having a relatively short cholesteric pitch have been proposed for use in displays exploiting the so called "flexo-electric" effect. The term "liquid crystal", "mesomorphic compound" or "mesogenic compound" (also shortly referred to as "mesogen") means a compound that under suitable conditions of temperature, pressure and concentration can exist as a mesophase (nematic, smectic, etc.) or in particular as a LC phase. Non-amphiphilic mesogenic compounds comprise for example one or more calamitic, banana-shaped or discotic mesogenic groups.

Flexoelectric liquid crystal materials are known in prior art. The flexoelectric effect is described inter alia by Chandrasekhar, "Liquid Crystals", 2nd edition, Cambridge University Press (1992) and P. G. deGennes et al., "The Physics of Liquid Crystals", 2nd edition, Oxford Science Publications (1995).

In these displays the cholesteric liquid crystals are oriented in the "uniformly lying helix" arrangement (ULH), which also give this display mode its name. For this purpose, a chiral substance which is mixed with a nematic material induces a helical twist transforming the material into a chiral nematic material, which is equivalent to a cholesteric material. The term "chiral" in general is used to describe an object that is non-superimposable on its mirror image. "Achiral" (non-chiral) objects are objects that are identical to their mirror image. The terms chiral nematic and cholesteric are used synonymously in this application, unless explicitly stated otherwise. The pitch induced by the chiral substance ($P_0$) is in a first approximation inversely proportional to the concentration (c) of the chiral material used. The constant of proportionality of this relation is called the helical twisting power (HTP) of the chiral substance and defined by equation (1)

$$HTP \equiv 1/(c \cdot P_0) \qquad (1)$$

wherein
c is the concentration of the chiral compound.

The uniform lying helix texture is realized using a chiral nematic liquid crystal with a short pitch, typically in the range from 0.2 μm to 1 μm, preferably of 1.0 μm or less, in particular of 0.5 μm or less, which is unidirectional aligned with its helical axis parallel to the substrates, e.g. glass plates, of a liquid crystal cell. In this configuration the helical axis of the chiral nematic liquid crystal is equivalent to the optical axis of a birefringent plate.

If an electrical field is applied to this configuration normal to the helical axis the optical axis is rotated in the plane of the cell, similar as the director of a ferroelectric liquid crystal rotate as in a surface stabilized ferroelectric liquid crystal display. The flexoelectric effect is characterized by fast response times typically ranging from 6 μs to 100 μs. It further features excellent grey scale capability.

The field induces a splay bend structure in the director which is accommodated by a tilt in the optical axis. The angle of the rotation of the axis is in first approximation directly and linearly proportional to the strength of the electrical field. The optical effect is best seen when the liquid crystal cell is placed between crossed polarizers with the optical axis in the unpowered state at an angle of 22.5° to the absorption axis of one of the polarizers. This angle of 22.5° is also the ideal angle of rotation of the electric field, as thus, by the inversion the electrical field, the optical axis is rotated by 45° and by appropriate selection of the relative orientations of the preferred direction of the axis of the helix, the absorption axis of the polarizer and the direction of the electric field, the optical axis can be switched from parallel to one polarizer to the center angle between both polarizers. The optimum contrast is then achieved when the total angle of the switching of the optical axis is 45°. In that case the arrangement can be used as a switchable quarter wave plate, provided the optical retardation, i.e. the product of the effective birefringence of the liquid crystal and the cell gap, is selected to be the quarter of the wave length. In this context the wavelength referred to is 550 nm, the wavelength for which the sensitivity of the human eye is highest, unless explicitly stated otherwise.

The angle of rotation of the optical axis ($\Phi$) is given in good approximation by formula (2)

$$\tan \Phi = \bar{e} P_0 E / (2\pi K) \qquad (2)$$

wherein
$P_0$ is the undisturbed pitch of the cholesteric liquid crystal,
$\bar{e}$ is the average [$\bar{e} = \frac{1}{2}(e_{splay} + e_{bend})$] of the splay flexoelectric coefficient ($e_{splay}$) and the bend flexoelectric coefficient ($e_{bend}$),
E is the electrical field strength and
K is the average [$K = \frac{1}{2}(k_{11} + k_{33})$] of the splay elastic constant ($k_{11}$) and the bend elastic constant ($K_{33}$)
and wherein
$\bar{e}/K$ is called the flexo-elastic ratio.

This angle of rotation is half the switching angle in a flexoelectric switching element.

The response time (τ) of this electro-optical effect is given in good approximation by formula (3)

$$\tau = [P_0/(2\pi)]^2 \cdot \gamma / K \quad (3)$$

wherein

γ is the effective viscosity coefficient associated with the distortion of the helix.

There is a critical field ($E_c$) to unwind the helix, which can be obtained from equation (4)

$$E_c = (\pi^2/P_0) \cdot [k_{22}/(\varepsilon_0 \cdot \Delta\varepsilon)]^{1/2} \quad (4)$$

wherein $k_{22}$ is the twist elastic constant, $\varepsilon_0$ is the permittivity of vacuum and Δε is the dielectric anisotropy of the liquid crystal.

In this mode, however, several problems still have to be resolved, which are, amongst others, difficulties in obtaining the required uniform orientation, an unfavorably high voltage required for addressing, which is incompatible with common driving electronics, a not really dark "off state", which deteriorates the contrast, and, last not least, a pronounced hysteresis in the electro-optical characteristics.

A relatively new display mode, the so-called uniformly standing helix (USH) mode, may be considered as an alternative mode to succeed the IPS, as it can show improved black levels, even compared to other display mode providing wide viewing angles (e.g. IPS, VA etc.).

For the USH mode, like for the ULH mode, flexoelectric switching has been proposed, using bimesogenic liquid crystal materials. Bimesogenic compounds are known in general from prior art (cf. also Hori, K., Iimuro, M., Nakao, A., Toriumi, H., J. Mol. Struc. 2004, 699, 23-29). The term "bimesogenic compound" relates to compounds comprising two mesogenic groups in the molecule. Just like normal mesogens they can form many mesophases, depending on their structure. In particular compounds of formula I induce a second nematic phase, when added to a nematic liquid crystal medium.

The term "mesogenic group" means in this context, a group with the ability to induce liquid crystal (LC) phase behaviour. The compounds comprising mesogenic groups do not necessarily have to exhibit an LC phase themselves. It is also possible that they show LC phase behaviour only in mixtures with other compounds. For the sake of simplicity, the term "liquid crystal" is used hereinafter for both mesogenic and LC materials.

However, due to the unfavorably high driving voltage required, to the relatively narrow phase range of the chiral nematic materials and to their irreversible switching properties, materials from prior art are not compatible for the use with current LCD driving schemes.

For displays of the USH and ULH mode, new liquid crystalline media with improved properties are required. Especially the birefringence (Δn) should be optimized for the optical mode. The birefringence Δn herein is defined in equation (5)

$$\Delta n = n_e - n_o \quad (5)$$

wherein $n_e$ is the extraordinary refractive index and $n_o$ is the ordinary refractive index, and the average refractive index $n_{av.}$ is given by the following equation (6).

$$n_{av.} = [(2n_o^2 + n_e^2)/3]^{1/2} \quad (6)$$

The extraordinary refractive index $n_e$ and the ordinary refractive index $n_o$ can be measured using an Abbe refractometer. Δn can then be calculated from equation (5).

Furthermore, for displays utilizing the USH or ULH mode the optical retardation d*Δn (effective) of the liquid crystal media should preferably be such that the equation (7)

$$\sin 2(\pi \cdot d \cdot \Delta n / \lambda) = 1 \quad (7)$$

wherein d is the cell gap and

λ is the wave length of light is satisfied. The allowance of deviation for the right hand side of equation (7) is +/−3%.

The wave length of light generally referred to in this application is 550 nm, unless explicitly specified otherwise.

The cell gap of the cells preferably is in the range from 1 μm to 20 μm, in particular within the range from 2.0 μm to 10 μm.

For the ULH/USH mode, the dielectric anisotropy (Δε) should be as small as possible, to prevent unwinding of the helix upon application of the addressing voltage. Preferably Δε should be slightly higher than 0 and very preferably be 0.1 or more, but preferably 10 or less, more preferably 7 or less and most preferably 5 or less. In the present application the term "dielectrically positive" is used for compounds or components with Δε>3.0, "dielectrically neutral" with −1.5≤Δε≤3.0 and "dielectrically negative" with Δε<−1.5. Δε is determined at a frequency of 1 kHz and at 20° C. The dielectric anisotropy of the respective compound is determined from the results of a solution of 10% of the respective individual compound in a nematic host mixture. In case the solubility of the respective compound in the host medium is less than 10% its concentration is reduced by a factor of 2 until the resultant medium is stable enough at least to allow the determination of its properties. Preferably the concentration is kept at least at 5%, however, in order to keep the significance of the results a high as possible. The capacitance of the test mixtures are determined both in a cell with homeotropic and with homogeneous alignment. The cell gap of both types of cells is approximately 20 μm. The voltage applied is a rectangular wave with a frequency of 1 kHz and a root mean square value typically of 0.5 V to 1.0 V, however, it is always selected to be below the capacitive threshold of the respective test mixture.

Δε is defined as $(\varepsilon_\parallel - \varepsilon_\perp)$, whereas $\varepsilon_{av.}$ is $(\varepsilon_\parallel + 2\varepsilon_\perp)/3$. The dielectric permittivity of the compounds is determined from the change of the respective values of a host medium upon addition of the compounds of interest. The values are extrapolated to a concentration of the compounds of interest of 100%. A typical The host mixture is disclosed in H. J. Coles et al., J. Appl. Phys. 2006, 99, 034104 and has the composition given in the table.

TABLE 1

| Host mixture composition | |
|---|---|
| Compound | Concentration |
| F-PGI-ZI9Z-GP-F | 25% |
| F-PGI-ZI11Z-GP-F | 25% |
| F-PGI-O5O-PP-N | 9.5% |
| F-PGI-O7O-PP-N | 39% |
| CD-1 | 1.5% |

Besides the above mentioned parameters, the media have to exhibit a suitably wide range of the nematic phase, a rather small rotational viscosity and an at least moderately high specific resistivity.

Similar liquid crystal compositions with short cholesteric pitch for flexoelectric devices are known from EP 0 971 016, GB 2 356 629 and Coles, H. J., Musgrave, B., Coles, M. J., and Willmott, J., J. Mater. Chem., 11, p. 2709-2716 (2001). EP 0 971 016 reports on mesogenic estradiols, which, as such, have a high flexoelectric coefficient. GB 2 356 629 suggests the use of bimesogenic compounds in flexoelectric devices. The flexoelectric effect herein has been investigated in pure cholesteric liquid crystal compounds and in mixtures of homologous compounds only so far. Most of these compounds were used in binary mixtures consisting of a chiral additive and a nematic liquid crystal material being either a simple, conventional monomesogenic material or a bimesogenic one. These materials do have several drawbacks for practical applications, like insufficiently wide temperature ranges of the chiral nematic—or cholesteric phase, too small flexoelectric ratios, small angles of rotation.

Symmetrical dimeric compounds showing liquid crystalline behaviour are disclosed in Joo-Hoon Park et al. "Liquid Crystalline Properties of Dimers Having o-, m- and p-Positional Molecular structures", Bill. Korean Chem. Soc., 2012, Vol. 33, No. 5, pp. 1647-1652.

One aim of the invention was to provide improved flexoelectric devices that exhibit high switching angles and fast response times. Another aim was to provide liquid crystal materials with advantageous properties, in particular for use in flexoelectric displays that enable good uniform alignment over the entire area of the display cell without the use of a mechanical shearing process, good contrast, high switching angles and fast response times also at low temperatures. The liquid crystal mixtures and preferably also the single compounds should exhibit low melting points, broad chiral nematic phase ranges, short temperature independent pitch lengths and high flexoelectric coefficients. Other aims of the present invention are immediately evident to the person skilled in the art from the following detailed description.

The inventors have found out that the above aims can be surprisingly achieved by providing bimesogenic compounds according to the present invention. These compounds, when used in chiral nematic liquid crystal mixtures, lead to low melting points, broad chiral nematic phases. In particular, they exhibit relatively high values of the elastic constant $k_{11}$, low values of the bend elastic constant $k_{33}$ and high values of the flexoelectric coefficient.

Thus, the present invention relates to compounds of formula I, preferably to bimesogenic compounds of formula I

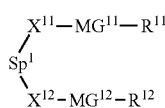

I wherein $R^{11}$ and $R^{12}$ are each independently H, F, Cl, CN, NCS or a straight-chain or branched alkyl group with 1 to 25 C atoms which may be unsubstituted, mono- or polysubstituted by halogen or CN, it being also possible for one or more non-adjacent $CH_2$ groups to be replaced, in each occurrence independently from one another, by —O—, —S—, —NH—, —N(CH$_3$)—, —CO—, —COO—, —OCO—, —O—CO—O—, —S—CO—, —CO—S—, —CH=CH—, —CH=CF—, —CF=CF— or —C≡C— in such a manner that oxygen atoms are not linked directly to one another, preferably a polar group, more preferably F, Cl, CN, OCF$_3$ or CF$_3$, more preferably F or Cl, most preferably F, $MG^{11}$ and $MG^{12}$ are each independently a cyclic group, preferably a mesogenic group, which is a 6-atomic ring or which comprises one, two or more 6-atomic rings, in case of comprising two or more 6-atomic rings at least two of these may be linked by a 2-atomic linking group, preferably selected from the group of linking groups —CO—O—, —O—CO—, —CH$_2$—O—, —O—CH$_2$—, —CF$_2$—O— and —O—CF$_2$—, and wherein additionally $MG^{11}$ is a or comprises a (i.e. one) 1,3-phenylene, wherein optionally one or two non-adjacent CH groups each may be replaced by an N-atom, and which optionally is substituted by one or more halogen atoms, preferably F and/or Cl, and/or by one or more alkyl group(s) each independently having 1 to 9 C atoms, preferably by one alkyl group having 1 to 9 C atoms and/or by one more alkoxy group(s) each independently having 1 to 9 C atoms, preferably by one alkoxy group having 1 to 9 C atoms, optionally said 1,3-phenylene is substituted by at least one alkyl group having 1 to 5 C atoms, preferably by CH$_3$ or by C$_2$H$_5$, and/or by at least one alkoxy group —O—C$_n$H$_{2n+1}$ with 1 to 4 C atoms, i.e. n=1, 2, 3 or 4, preferably this ring is linked to or adjacent to the group $Sp^1$, $Sp^1$ is a spacer group comprising 1, 2, 3, 4 or 5 to 40 C atoms, wherein one or more non-adjacent and non-terminal CH$_2$ groups may also be replaced by —O—, —S—, —NH—, —N(CH$_3$)—, —CO—, —O—CO—, —S—CO—, —O—COO—, —CO—S—, —CO—O—, —CH(halogen)-, —CH(CN)—, —CH=CH— or —C≡C—, however in such a way that no two O-atoms are adjacent to one another, now two —CH=CH— groups are adjacent to each other and no two groups selected from —O—CO—, —S—CO—, —O—COO—, —CO—S—, —CO—O— and —CH=CH— are adjacent to each other, preferably —(CH$_2$)$_n$— (i.e. 1, n-alkylene with n C-atoms), with n an integer, preferably from 2 to 19, more preferably from 2 to 11, most preferably an even integer (i.e. 2, 4, 6, 8 or 10), wherein one or more H atoms in —(CH$_2$)$_n$— may independently of each other optionally be replaced by F or CH$_3$ and/or one or more non-adjacent —CH$_2$— groups may be replaced by —O—, $X^{11}$ and $X^{12}$ are each independently of one another a group selected from —CH=CH—, —C≡C—, —O—, —CF$_2$—O—, —O—CF$_2$—, —CO—O—, —O—CO—, —O—CO—O—, —S—, —CS—S—, —S—CS—, —CO—S—, —S—CO—, —S—CO—S— and —S—CS—S— or a single bond, preferably selected from —O—, —CO—O—, —O—CO—, —S—CO— and —CO—S— or a single bond,
most preferably —CO—S—, —S—CO—, —O—CO— or —CO—O—, however, under the condition that in —$X^{11}$-$Sp^1$-$X^{12}$— no two O-atoms are adjacent to one another, now two —CH=CH— groups are adjacent to each other and no two groups selected from —O—CO—, —S—CO—, —O—COO—, —CO—S—, —CO—O— and —CH=CH— are adjacent to each other.

Preferably $MG^{11}$ is 1,3-phenylene or comprises a 1,3-phenylene moiety.

Preferably in formula I
—$X^{11}$-$Sp^1$-$X^{12}$— is —O—CO-$Sp^1$-CO—O—, —O-$Sp^1$-O—, -$Sp^1$- or —S—CO-$Sp^1$-CO—S—,
$Sp^1$ is —(CH$_2$)$_n$— with
n 1, 2, 3, 4 or an integer from 5 to 15, most preferably an even integer and, most preferably 6 or 8, wherein one or more H atoms in —(CH$_2$)$_n$— may independently of each other optionally be replaced by F or CH$_3$ and/or one or more non-adjacent —CH$_2$— groups may be replaced by —O—.

Preferred compounds of formula I are compounds in which
MG$^{11}$ is a group of (partial) formula II*

-A*$^{11}$-(Z*$^{11}$-A*$^{12}$)$_k$-   II* and
MG$^{12}$ is a group of (partial) formula II

-A$^{11}$-(Z$^{11}$-A$^{12}$)$_l$-   II wherein
Z$^{11}$ and Z*$^{11}$ are, independently of each other in each occurrence, a single bond, —COO—, —OCO—, —O—CO—O—, —OCH$_2$—, —CH$_2$O—, —OCF$_2$—, —CF$_2$O—, —CH$_2$CH$_2$—, —(CH$_2$)$_4$—, —CF$_2$CF$_2$—, —CH=CH—, —CF=CF—, —CH=CH—COO—, —OCO—CH=CH— or —C≡C—, optionally substituted with one or more of F, preferably a single bond,
one of
A*$^{11}$ and A*$^{12}$ present in MG$^{11}$ is
  1,3-phenylene, wherein optionally one or two non-adjacent CH groups each may be replaced by an N-atom, and which optionally is substituted by one or more halogen atoms and/or by one or more alkyl group(s) each independently having 1 to 9 C atoms, preferably by one alkyl group having 1 to 9 C atoms or by one more alkoxy group(s) each independently having 1 to 9 C atoms, preferably by one alkoxy group having 1 to 9 C atoms,
  optionally said 1,3-phenylene is substituted by at least one alkyl group having 1 to 5 C atoms, preferably by CH$_3$ or by C$_2$H$_5$, and/or by at least one alkoxy group, and
the other A*$^{11}$ and A*$^{12}$ present in MG$^{11}$
and A$^{11}$ and A$^{12}$ are each independently of each other in each occurrence 1,4-phenylene, wherein in addition one or more CH groups may be replaced by N, trans-1,4-cyclohexylene in which, in addition, one or two non-adjacent CH$_2$ groups may be replaced by O and/or S, 1,4-cyclohexenylene, 1,4-bicyclo-(2,2,2)-octylene, piperidine-1,4-diyl, naphthalene-2,6-diyl, decahydro-naphthalene-2,6-diyl, 1,2,3,4-tetrahydro-naphthalene-2,6-diyl, cyclobutane-1,3-diyl, spiro[3.3]heptane-2,6-diyl or dispiro[3.1.3.1]decane-2,8-diyl, it being possible for all these groups to be unsubstituted, mono-, di-, tri- or tetrasubstituted with F, Cl, CN or alkyl, alkoxy, alkylcarbonyl or alkoxycarbonyl groups with 1 to 7 C atoms, wherein one or more H atoms may be substituted by F or Cl, preferably F, Cl, CH$_3$ or CF$_3$, and
k and l are independently of each other 0, 1, 2, 3 or 4, preferably 1, 2 or 3 and l alternatively also 0 and, most preferably, 1 or 2 and l alternatively also 0.

Especially preferred are compounds of formula I wherein the cyclic respectively mesogenic groups MG$^{11}$ and MG$^{12}$ at each occurrence independently from each other comprise one, two or three six-membered rings, preferably two or three six-membered rings.

A smaller group of preferred cyclic, preferably mesogenic groups MG$^{12}$ of formula II is listed below. For reasons of simplicity, Phe in these groups is 1,4-phenylene or alkyl-1,4-phenylene, PheL is a 1,4-phenylene group which is substituted by 1 to 4 groups L, with L being preferably F, Cl, CN, OH, NO$_2$ or an optionally fluorinated alkoxy or alkanoyl group with 1 to 7 C atoms, very preferably F, Cl, CN, OH, NO$_2$, CH$_3$, C$_2$H$_5$, OCH$_3$, OC$_2$H$_5$, COCH$_3$, COC$_2$H$_5$, COOCH$_3$, COOC$_2$H$_5$, CF$_3$, OCF$_3$, OCHF$_2$, OC$_2$F$_5$, in particular F, Cl, CN, CH$_3$, C$_2$H$_5$, OCH$_3$, COCH$_3$ and OCF$_3$, most preferably F, Cl, CH$_3$, OCH$_3$ and COCH$_3$ and Cyc is 1,4-cyclohexylene. This list comprises the subformulae shown below as well as their mirror images

| | |
|---|---|
| -Phe- | II-0 |
| -PheL- II- | 0' |
| -Phe-Z-Phe- | II-1 |
| -Phe-Z-Cyc- | II-2 |
| -Cyc-Z-Cyc- | II-3 |
| -Phe-Z-PheL- | II-4 |
| -PheL-Z-Phe- | II-5 |
| -PheL-Z-Cyc- | II-6 |
| -PheL-Z-PheL- | II-7 |
| -Phe-Z-Phe-Z-Phe- | II-8 |
| -Phe-Z-Phe-Z-Cyc- | II-9 |
| -Phe-Z-Cyc-Z-Phe- | II-10 |
| -Cyc-Z-Phe-Z-Cyc- | II-11 |
| -Phe-Z-Cyc-Z-Cyc- | II-12 |
| -Cyc-Z-Cyc-Z-Cyc- | II-13 |
| -Phe-Z-Phe-Z-PheL- | II-14 |
| -Phe-Z-PheL-Z-Phe- | II-15 |
| -PheL-Z-Phe-Z-Phe- | II-16 |
| -PheL-Z-Phe-Z-PheL- | II-17 |
| -PheL-Z-PheL-Z-Phe- | II-18 |
| -PheL-Z-PheL-Z-PheL- | II-19 |
| -Phe-Z-PheL-Z-Cyc- | II-20 |
| -Phe-Z-Cyc-Z-PheL- | II-21 |
| -Cyc-Z-Phe-Z-PheL- | II-22 |
| -PheL-Z-Cyc-Z-PheL- | II-23 |
| -PheL-Z-PheL-Z-Cyc- | II-24 |
| -PheL-Z-Cyc-Z-Cyc- | II-25 |
| -Cyc-Z-PheL-Z-Cyc- | II-26 | wherein preferably
Cyc is 1,4-cyclohexlene, preferably trans-1,4-cyclohexlene,
Phe is 1,4-phenylene or alkyl-1,4-phenylene,
PheL is 1,4-phenylene, which is substituted by one, two or three fluorine atoms, by one or two Cl atoms or by one Cl atom and one F atom, and
Z has one of the meanings of Z$^{11}$ as given under partial formula II, at least one is preferably selected from —COO—, —OCO—, —O—CO—O—, —OCH$_2$—, —CH$_2$O—, —OCF$_2$— or —CF$_2$O—.

Particularly preferred are the sub-formulae II-0, II-0', II-1, II-4, II-5, II-7, II-8, II-14, II-15, II-16, II-17, II-18 and II-19 and most preferred is the sub-formula II-1.

A smaller group of preferred cyclic, preferably mesogenic groups $MG^{11}$ of formula II* is listed below. Wherein the identical abbreviations have the respective meanings given under formulae II-1 to II-26 above and, for reasons of simplicity, Phe* in these groups is 1,3-phenylene, 4-alkyl-1,3-phenylene or 4-alkoxy-1,3-phenylene, Phe*L is a 1,3-phenylene group, which is substituted by 1 to 4 groups L, preferably by one or two groups L, or 4-alkyl-1,3-phenylene or 4-alkoxy-1,3-phenylene, which is substituted by 1 to 3 groups L, preferably by 1 group L, with L in each case independently being preferably F, Cl, CN, OH, $NO_2$ or an optionally fluorinated alkoxy or alkanoyl group with 1 to 7 C atoms, very preferably F, Cl, CN, OH, $NO_2$, $CH_3$, $C_2H_5$, $OCH_3$, $OC_2H_5$, $COCH_3$, $COC_2H_5$, $COOCH_3$, $COOC_2H_5$, $CF_3$, $OCF_3$, $OCHF_2$, $OC_2F_5$, in particular F, Cl, CN, $CH_3$, $C_2H_5$, $OCH_3$, $COCH_3$ and $OCF_3$, most preferably F, Cl, $CH_3$, $OCH_3$ and $COCH_3$ and Cyc is 1,4-cyclohexylene. This list comprises the sub-formulae shown below as well as their mirror images

| | |
|---|---|
| -Phe*- | II*-0 |
| -Phe*L- | II*-0' |
| -Phe*-Z-Phe- | II*-1 |
| -Phe-Z-Phe*- | II*-1 |
| -Phe*-Z-Cyc- | II*-2 |
| -Phe*-Z-PheL- | II*-4 |
| -Phe*L-Z-Phe- | II*-5 |
| -Phe*L-Z-Cyc- | II*-6 |
| -Phe*L-Z-PheL- | II*-7 |
| -Phe*-Z-Phe-Z-Phe- | II*-8 |
| -Phe*-Z-Phe-Z-Cyc- | II*-9 |
| -Phe*-Z-Cyc-Z-Phe- | II*-10 |
| -Cyc-Z-Phe*-Z-Cyc- | II*-11 |
| -Phe*-Z-Cyc-Z-Cyc- | II*-12 |
| -Phe*-Z-Phe-Z-PheL- | II*-13 |
| -Phe-Z-Phe*-Z-PheL- | II*-14 |
| -Phe*-Z-PheL-Z-Phe- | II*-15 |
| -Phe*L-Z-Phe-Z-Phe- | II*-16 |
| -Phe*L-Z-Phe-Z-PheL- | II*-17 |
| -Phe*L-Z-PheL-Z-Phe- | II*-18 |
| -Phe*L-Z-PheL-Z-PheL- | II*-19 |
| -Phe*-Z-PheL-Z-Cyc- | II*-20 |
| -Phe*-Z-Cyc-Z-PheL- | II*-21 |
| -Cyc-Z-Phe*-Z-PheL- | II*-22 |
| -Phe*L-Z-Cyc-Z-PheL- | II*-23 |
| -Phe*L-Z-PheL-Z-Cyc- | II*-24 |
| -Phe*L-Z-Cyc-Z-Cyc- | II*-25 |
| -Cyc-Z-Phe*L-Z-Cyc- | II*-26 | wherein preferably

Cyc is 1,4-cyclohexlene, preferably trans-1,4-cyclohexlene,
Phe* is 1,3-phenylene or alkyl-1,3-phenylene,
Phe is 1,4-phenylene or alkyl-1,4-phenylene, include 1,3-phenylene,
Phe*L is 1,3-phenylene, which is substituted by one, two or three fluorine atoms, by one or two Cl atoms or by one Cl atom and one F atom,
PheL is 1,4-phenylene, which is substituted by one, two or three fluorine atoms, by one or two Cl atoms or by one Cl atom and one F atom, and
Z has one of the meanings of $Z^{*11}$ as given under partial formula II*, at least one is preferably selected from —COO—, —OCO—, —O—CO—O—, —$OCH_2$—, —$CH_2O$—, —$OCF_2$— or —$CF_2O$—.

Particularly preferred are the sub-formulae II*-0, II*-0', II*-1, II*-4, II*-5, II*-7, II*-8, II*-14, II*-15, II*-16, II*-17, II*-18 and II*-19 and most preferred is the sub-formula II*-1.

In these preferred groups Z in each case independently has one of the meanings of $Z^{11}$ as given under formula I. Preferably one of Z is —COO—, —OCO—, —$CH_2$—O—, —O—$CH_2$—, —$CF_2$—O— or —O—$CF_2$—, more preferably —COO—, —O—$CH_2$— or —$CF_2$—O—, and the others preferably are a single bond.

Very preferably the cyclic, preferably mesogenic group $MG^{11}$ is selected from the following formulae II*aa1, II*a1 II*d1, II*aa2 and II*2a to II*d2 and their mirror images

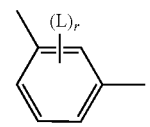

II*aa1

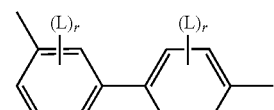

II*a1

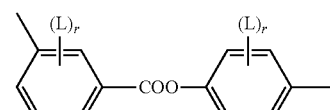

II*b1

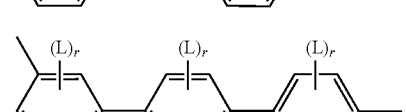

II*c1

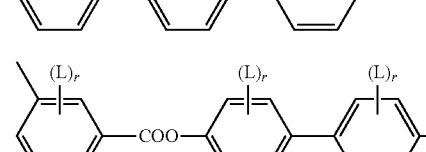

II*d1

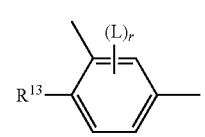

II*aa2

-continued

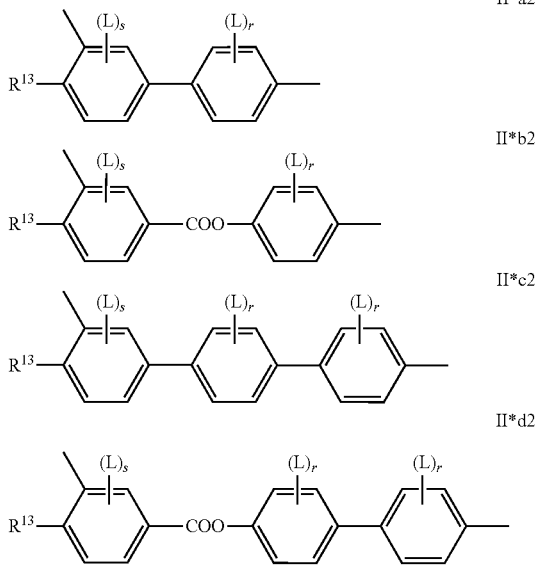

wherein

Z has one of the meanings of $Z^{*11}$ as given under partial formula II*, at least one is preferably selected from —COO—, —OCO—, —O—CO—O—, —OCH$_2$—, —CH$_2$O—, —OCF$_2$— or —CF$_2$O—.

L is in each occurrence independently of each other R, F or Cl, preferably R or F, r is in each occurrence independently of each other 0, 1, 2 or 3, preferably 0, 1 or 2, s is 0, 1 or 2, preferably 0 or 1, R is alkyl having 1 to 5 C-atoms, preferably n-alkyl, more preferably methyl or ethyl, and $R^{13}$ is alkyl having 1 to 9 C atoms, or alkoxy having 1 to 9 C atoms, preferably alkyl having 1 to 5 C-atoms, preferably n-alkyl, more preferably methyl or ethyl.

Preferred are the formulae II*a1, II*b1 and II*c1, and, particularly preferred, II*a1.

The group

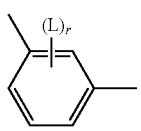

in these preferred formulae is very preferably denoting

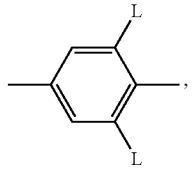

furthermore

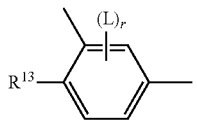

wherein
L is in each occurrence independently of each other R, as defined above, F or Cl.

The group

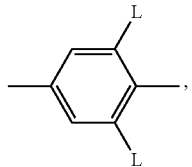

in these preferred formulae is very preferably denoting

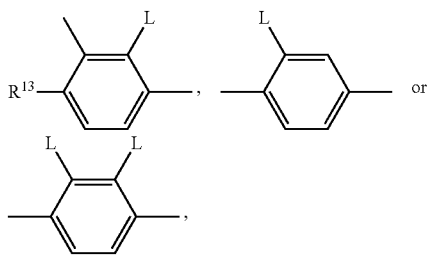

furthermore

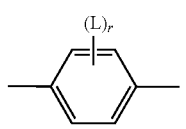

wherein
L is in each occurrence independently of each other R, as defined above, F or Cl, and
$R^{13}$ is as defined above and preferably an alkyl or an alkoxy group.

Very preferably the mesogenic group $MG^{12}$ is selected from the following formulae IIaa and IIa to IIo and their mirror images IIaa IIa

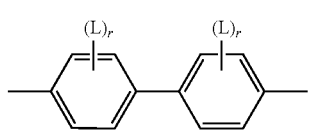

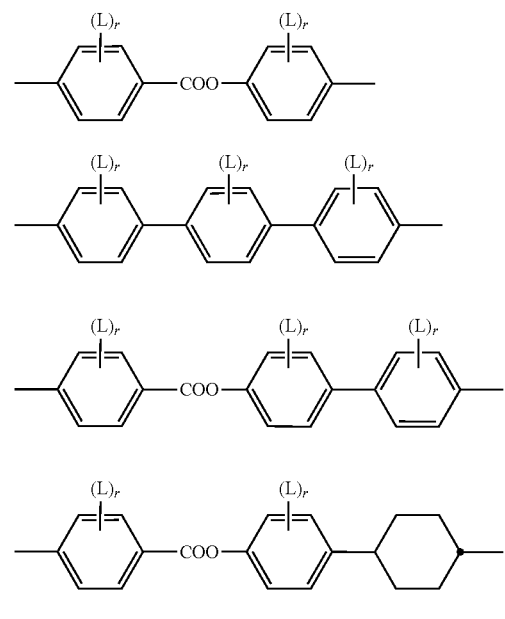

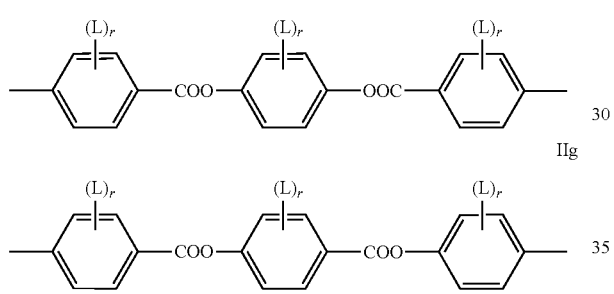

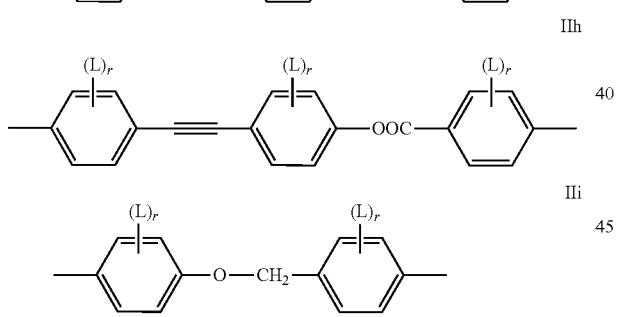

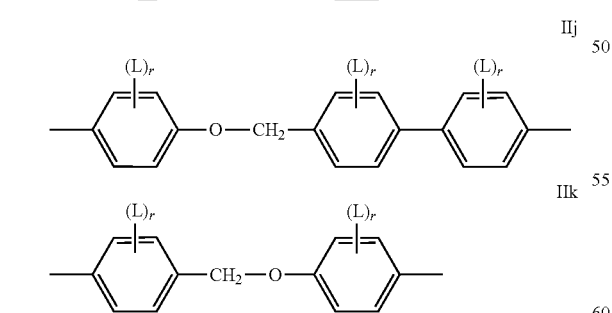

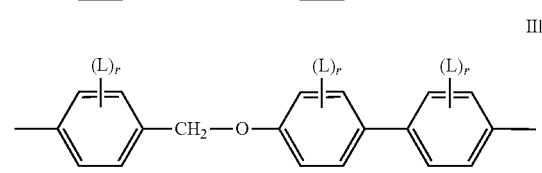

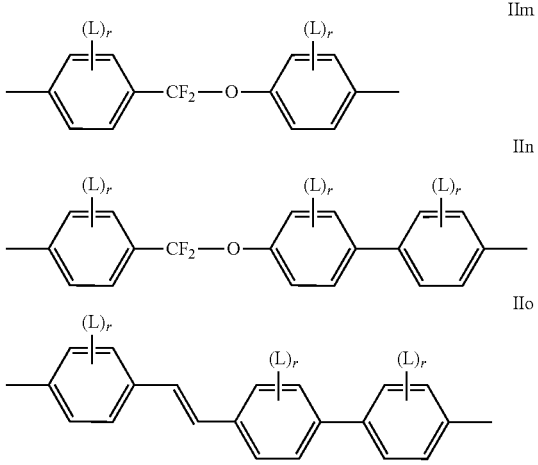

wherein
L is in each occurrence independently of each other R, F or Cl, preferably R or F,
r is in each occurrence independently of each other 0, 1, 2 or 3, preferably 0, 1 or 2.
The group

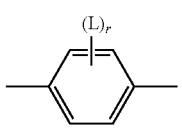

in these preferred formulae is very preferably denoting

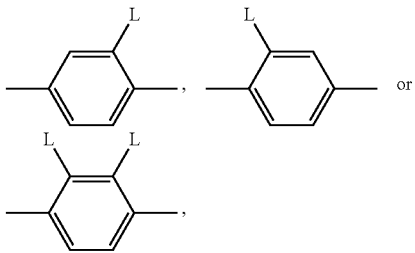

furthermore

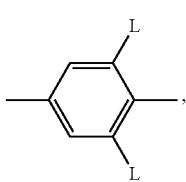

wherein
L is in each occurrence independently of each other R, F or Cl,
R is alkyl having 1 to 5 C-atoms, preferably n-alkyl, more preferably methyl or ethyl.

Particularly preferred are the sub-formulae IIa, IIb and IIc.

Most preferably $MG^{11}$ is selected from the following formulae II*-aa-2-1, II*a2-1 and II*c2-1

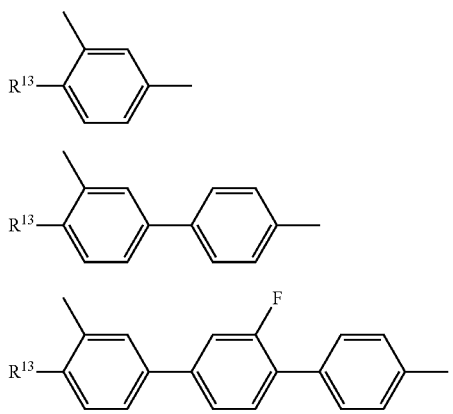

II*aa2-1

II*a2-1

II*c2-1 wherein $R^{13}$ has the meaning given above or optionally may be H and preferably is alkyl having 1 to 5 C-atoms or alkoxy having 1 to 5 C-atoms, preferably n-alkyl or n-alkoxy, more preferably methyl or ethyl or alkoxy having 1 to 3 C atoms and, most preferably, is methyl.

In case of compounds with an unpolar group, $R^{11}$ and $R^{12}$ are preferably alkyl with up to 15 C atoms or alkoxy with 1 to 15 C atoms.

If $R^{11}$ or $R^{12}$ is an alkyl or alkoxy radical, i.e. where the terminal $CH_2$ group is replaced by —O—, this may be straight-chain or branched. It is preferably straight-chain, has 2, 3, 4, 5, 6, 7 or 8 carbon atoms and accordingly is preferably ethyl, propyl, butyl, pentyl, hexyl, heptyl, octyl, ethoxy, propoxy, butoxy, pentoxy, hexoxy, heptoxy or octoxy, furthermore methyl, nonyl, decyl, undecyl, dodecyl, tridecyl, tetradecyl, pentadecyl, nonoxy, decoxy, undecoxy, dodecoxy, tridecoxy or tetradecoxy, for example.

Oxaalkyl, i.e. where one $CH_2$ group is replaced by —O—, is preferably straight-chain 2-oxapropyl(=methoxymethyl), 2-(=ethoxymethyl) or 3-oxabutyl(=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-,7-, 8- or 9-oxadecyl, for example.

In case of a compounds with a terminal polar group, $R^{11}$ and $R^{12}$ are selected from CN, $NO_2$, halogen, $OCH_3$, OCN, SCN, $COR^x$, $COOR^x$ or a mono- oligo- or polyfluorinated alkyl or alkoxy group with 1 to 4 C atoms. $R^x$ is optionally fluorinated alkyl with 1 to 4, preferably 1 to 3 C atoms. Halogen is preferably F or Cl, more preferably F.

Especially preferably $R^{11}$ and $R^{12}$ in formula I are selected of H, F, Cl, CN, $NO_2$, $OCH_3$, $COCH_3$, $COC_2H_5$, $COOCH_3$, $COOC_2H_5$, $CF_3$, $C_2F_5$, $OCF_3$, $OCHF_2$, and $OC_2F_5$, in particular of H, F, Cl, CN, $OCH_3$ and $OCF_3$, especially of H, F, CN and $OCF_3$.

In addition, compounds of formula I containing an achiral branched group $R^{11}$ and/or $R^{12}$ may occasionally be of importance, for example, due to a reduction in the tendency towards crystallisation. Branched groups of this type generally do not contain more than one chain branch. Preferred achiral branched groups are isopropyl, isobutyl(=methylpropyl), isopentyl(=3-methylbutyl), isopropoxy, 2-methylpropoxy and 3-methylbutoxy.

The spacer group $Sp^1$ is preferably a linear or branched alkylene group having 1, 3 or 5 to 40 C atoms, in particular 1, 3 or 5 to 25 C atoms, very preferably 1, 3 or 5 to 15 C atoms, and most preferably 5 to 15 C atoms, in which, in addition, one or more non-adjacent and non-terminal $CH_2$ groups may be replaced by —O—, —S—, —NH—, —N($CH_3$)—, —CO—, —O—CO—, —S—CO—, —O—COO—, —CO—S—, —CO—O—, —CH(halogen)-, —CH(CN)—, —CH=CH— or —C≡C—.

"Terminal" $CH_2$ groups are those bound to the respective linking group "$X^{11}$" and/or "$X^{11}$" or directly to the respective cyclic, preferably mesogenic group $MG^{11}$ and/or the respective mesogenic group $MG^{12}$. Accordingly, "non-terminal" $CH_2$ groups are not bound to the respective linking group "$X^{11}$" and/or "$X^{11}$" or directly to the respective cyclic, preferably mesogenic group $MG^{11}$ and/or the respective mesogenic group $MG^{12}$.

Typical spacer groups are for example —$(CH_2)_o$—, —$(CH_2CH_2O)_p$—$CH_2CH_2$—, with o being an integer from 5 to 40, in particular from 5 to 25, very preferably from 5 to 15, and p being an integer from 1 to 8, in particular 1, 2, 3 or 4.

Preferred spacer groups are pentylene, hexylene, heptylene, octylene, nonylene, decylene, undecylene, dodecylene, octadecylene, diethyleneoxyethylene, dimethyleneoxybutylene, pentenylene, heptenylene, nonenylene and undecenylene, for example.

Especially preferred are inventive compounds of formula I wherein Sp is denoting alkylene with 5 to 15 C atoms. Straight-chain alkylene groups are especially preferred.

Preferred are spacer groups, which are straight-chain alkylene with odd numbers of C atoms, preferably a having 5, 7, 9, 11, 13 or 15 C atoms, very preferred are straight-chain alkylene spacers having 7, 9, and 11 C atoms.

In another embodiment of the present invention the spacer groups are straight-chain alkylenes with even numbers of C atoms, preferably having 6, 8, 10, 12 and 14 C atoms. This embodiment is particularly preferred if one of $X^{11}$ and $X^{12}$ consists of one atom, i.e. is —S— or —O—, or of three atoms, e.g. is —S—CO—, —S—CO—S— or —S—CS—S—, and the other does not consist of one or three C atoms.

In a preferred embodiment of the present invention the inventive compounds of formula I comprise $Sp^1$ is denoting complete deuterated alkylene with 5 to 15 C atoms. Very preferred are deuterated straight-chain alkylene groups. Most preferred are partially deuterated straight-chain alkylene groups.

One preferred embodiment of the present invention are compounds of formula I wherein the groups $R^{11}$-$MG^{11}$-$X^{11}$— and $R^{12}$-$MG^{12}$-$X^{12}$— are identical to one another.

Another preferred embodiment of the present invention are compounds of formula I wherein $R^{11}$-$MG^{11}$-$X^{11}$— and $R^{12}$-$MG^{12}$-$X^{12}$— in formula I are are different from each other.

Preferred compounds of formula I are selected from the group of compounds of formulae IAA and IA to IE, IAA' and IA' to IE', preferably of formulae IAA and/or IA and/or IC,

IAA

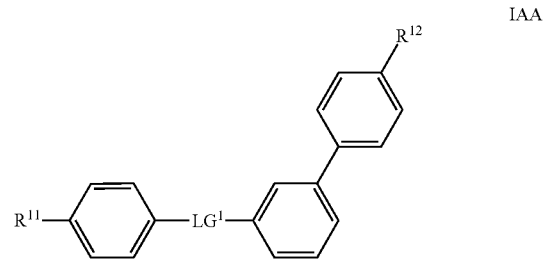

IA
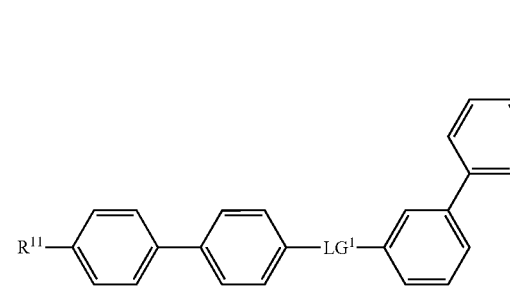
IB
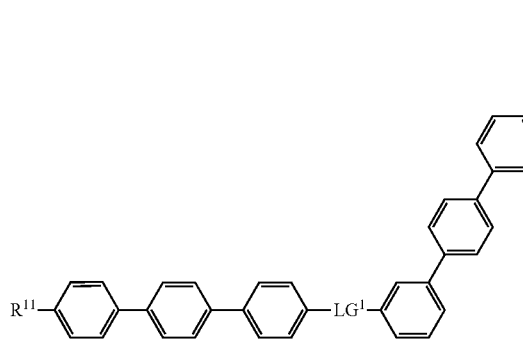
IC
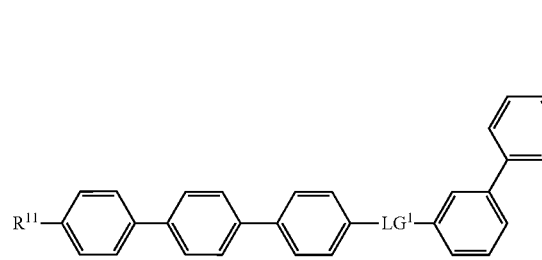
ID
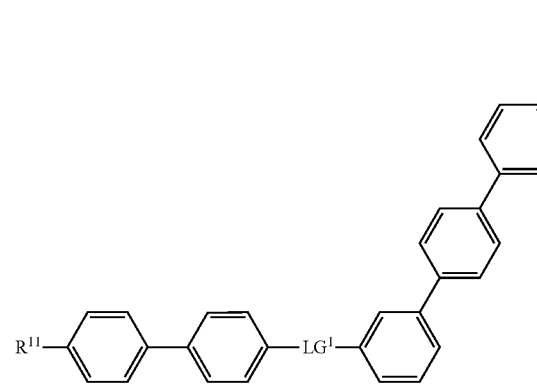
IE
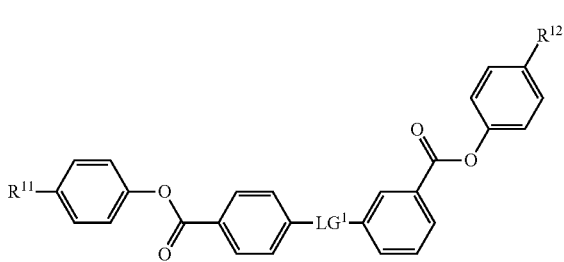
IAA'
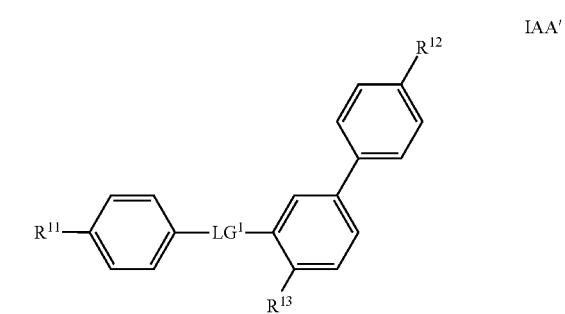
IA'
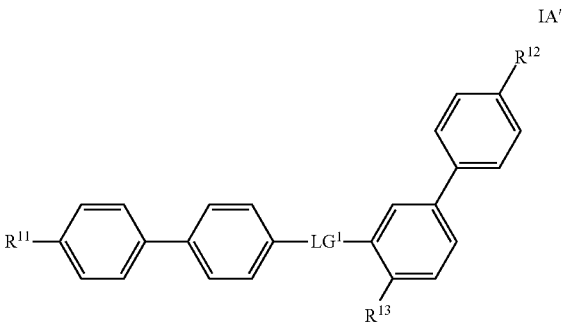
IB'
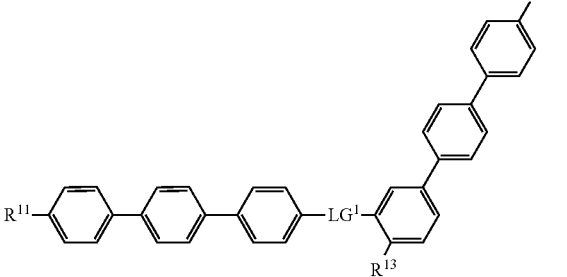
IC'
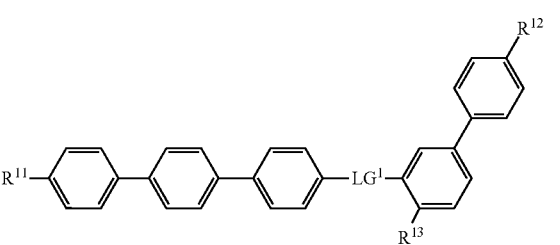
ID'
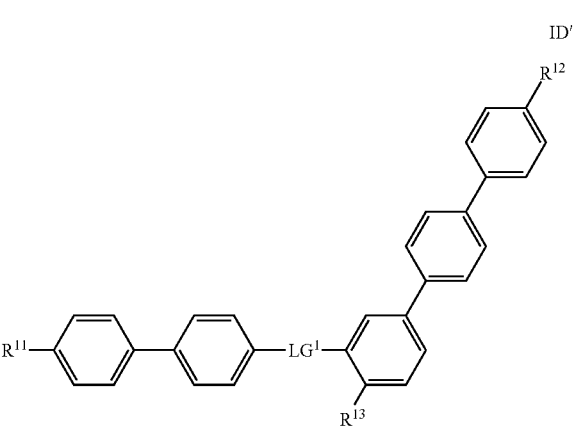

-continued

IE'

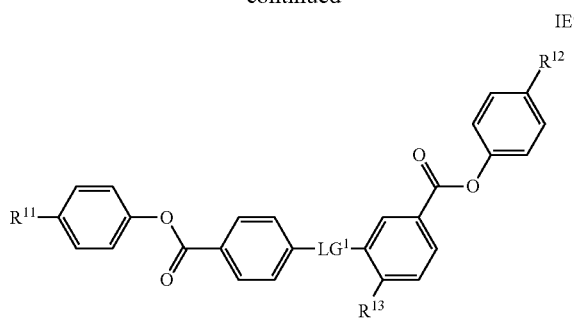

wherein
LG$^1$ is —X$^{11}$-Sp$^1$-X$^{12}$—,
and
the parameters have the respective meanings given above including the preferred meanings,
preferably at least one of the 1,3-phenylene rings is substituted by an alkyl group R and/or an alkoxy group (R—O) and/or by one or more F or Cl-atoms, preferably by one alkyl group and/or one or more F atoms and all of the 1,4-phenylene rings are optionally further substituted by one or more F or Cl-atoms, preferably at most by one Cl or by one or two F-atoms each, and
LG$^1$ preferably is —O—CO-Sp$^1$-CO—O—, —O-Sp$^1$-O—, -Sp$^1$- or —S—CO-Sp$^1$-CO—S—, more preferably —O—CO-Sp$^1$-CO—O—, —O-Sp$^1$-O— or -Sp$^1$-,
Sp$^1$ preferably is —(CH$_2$)$_n$— with
n an integer from 1 to 15, most preferably an even integer and, most preferably 2, 4, 6 or 8.

Particularly preferred compounds of formula IA are selected from the group of compounds of formulae IA-1 to IA-3 wherein the parameters have the respective meanings given above including the preferred meanings and
preferably R$^{11}$ and R$^{12}$ are independently from each other as defined above, OCF$_3$, CF$_3$, F or CN, more preferably F or CN and most preferably CN.

Particularly preferred compounds are selected from the group of formulae given above, which bear 0, 2 or 4 F atoms in lateral positions (i.e. as L).

In a preferred embodiment of the present invention R$^{11}$ is OCF$_3$ or CN, preferably CN, and R$^{12}$ is OCF$_3$, F or CN, preferably also CN.

The compounds of formula I can be synthesized according to or in analogy to methods which are known per se and which are described in standard works of organic chemistry such as, for example, Houben-Weyl, Methoden der organischen Chemie, Thieme-Verlag, Stuttgart. A preferred method of preparation can be taken from the following synthesis schemes.

The compounds of formula I are preferably accessible according to the following general reaction schemes.

Reaction Scheme I

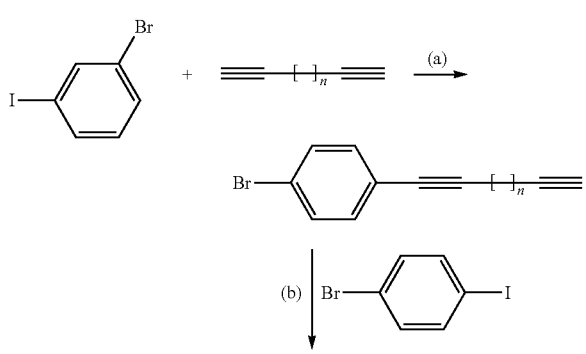

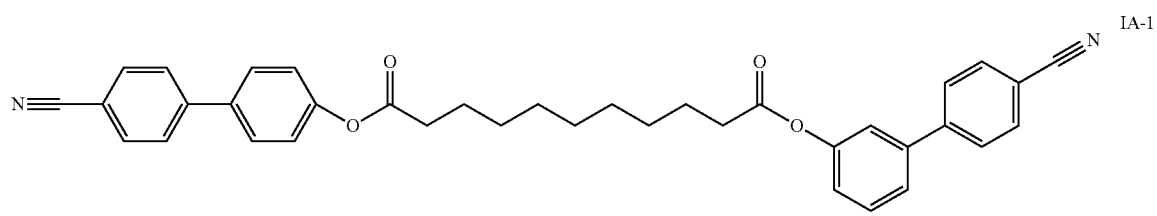

IA-1

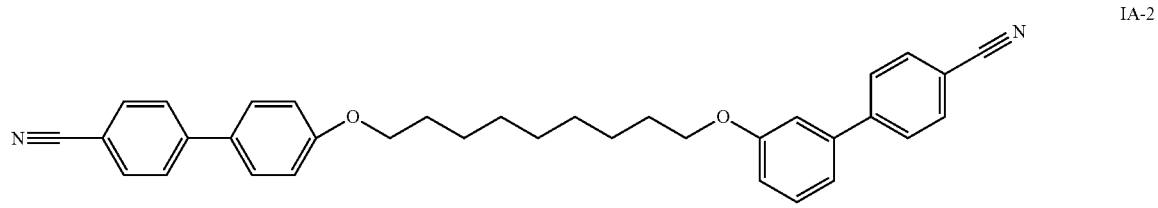

IA-2

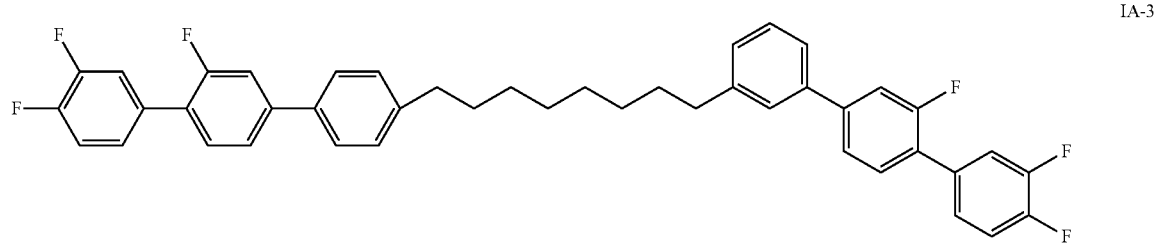

IA-3

21
-continued

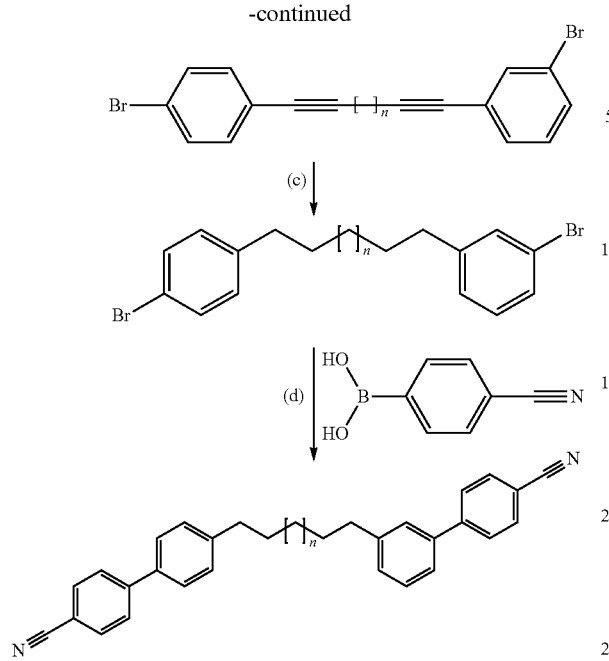

22 wherein n is an integer from 2 to 15, preferably 2, 4, 6 or 8, preferably an even integer and most preferably 6 or 8, R independently in each occurrence has one of the meanings given for $R^{11}$ and in the second occurrence alternatively may have one of the additional meanings given for $R^{12}$ including the preferred meanings of these groups, and the conditions of the successive reactions are as follows:

a) $Pd(PPh_3)_2Cl_2$, CuI, Diisopropylamine $(NH(iPr.)_2)$, THF;

b) $Pd(PPh_3)_2Cl_2$, CuI, $NH(iPr)_2$, THF;

c) Pt/C, $H_2$; and d) $Pd(PPh_3)_2Cl_2$, THF, $NaCO_3$, $H_2O$.

All phenylene moieties shown in this scheme and in the following schemes may independently of each other be optionally bearing one, two or three, preferably by no or one, F— or Cl—, preferably F—, atom.

An exemplary reaction scheme for the preparation of such a fluorinated compound is shown in the following scheme.

Reaction Scheme II

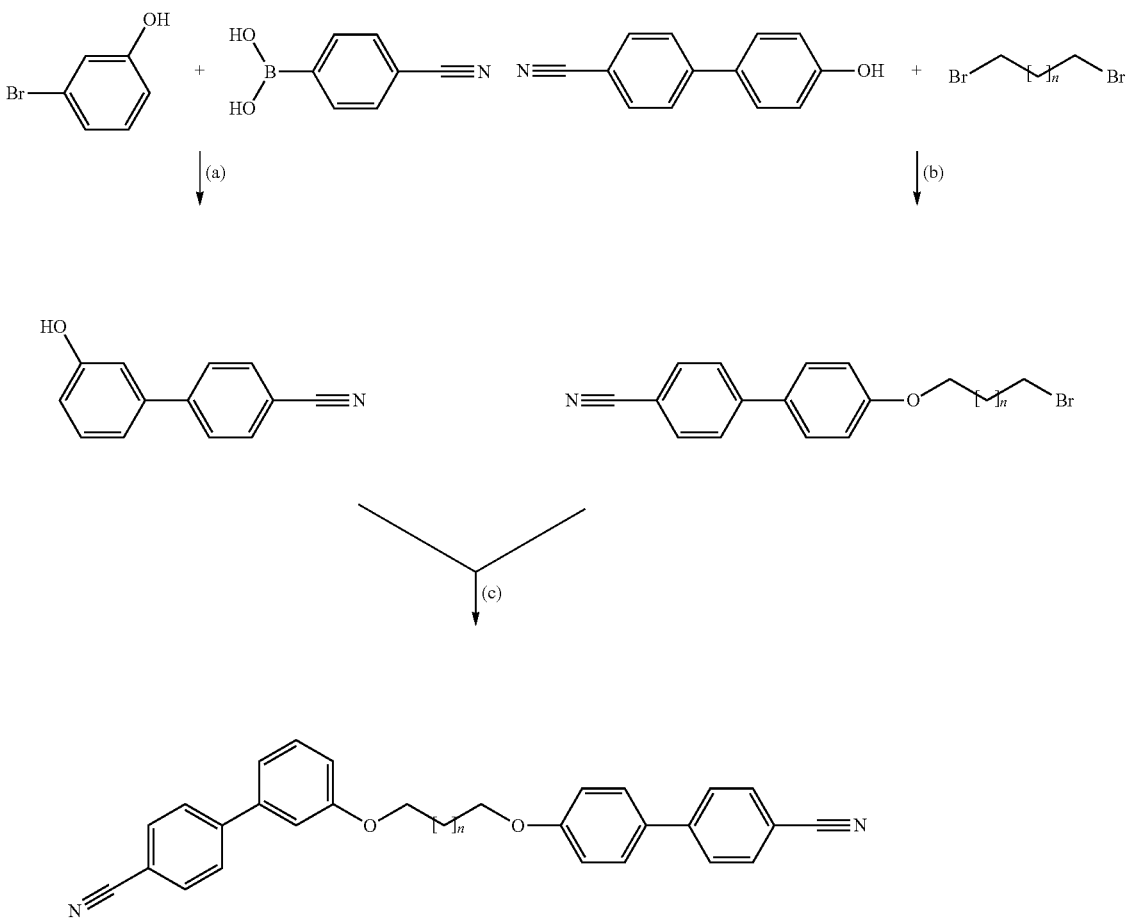

wherein n is an integer of 0, 1, 2, 3 of or from 4 to 15, preferably 3, 4, 5, 6, 7 or 8 and the conditions of the successive reactions are as follows:

a) Pd(dppf)Cl$_2$, Na$_2$CO$_3$, H$_2$O, Dioxane;
b) K$_2$CO$_3$, (CH$_3$)$_2$CO; and
c) K$_2$CO$_3$, (CH$_3$)$_2$CO.

Reaction Scheme III

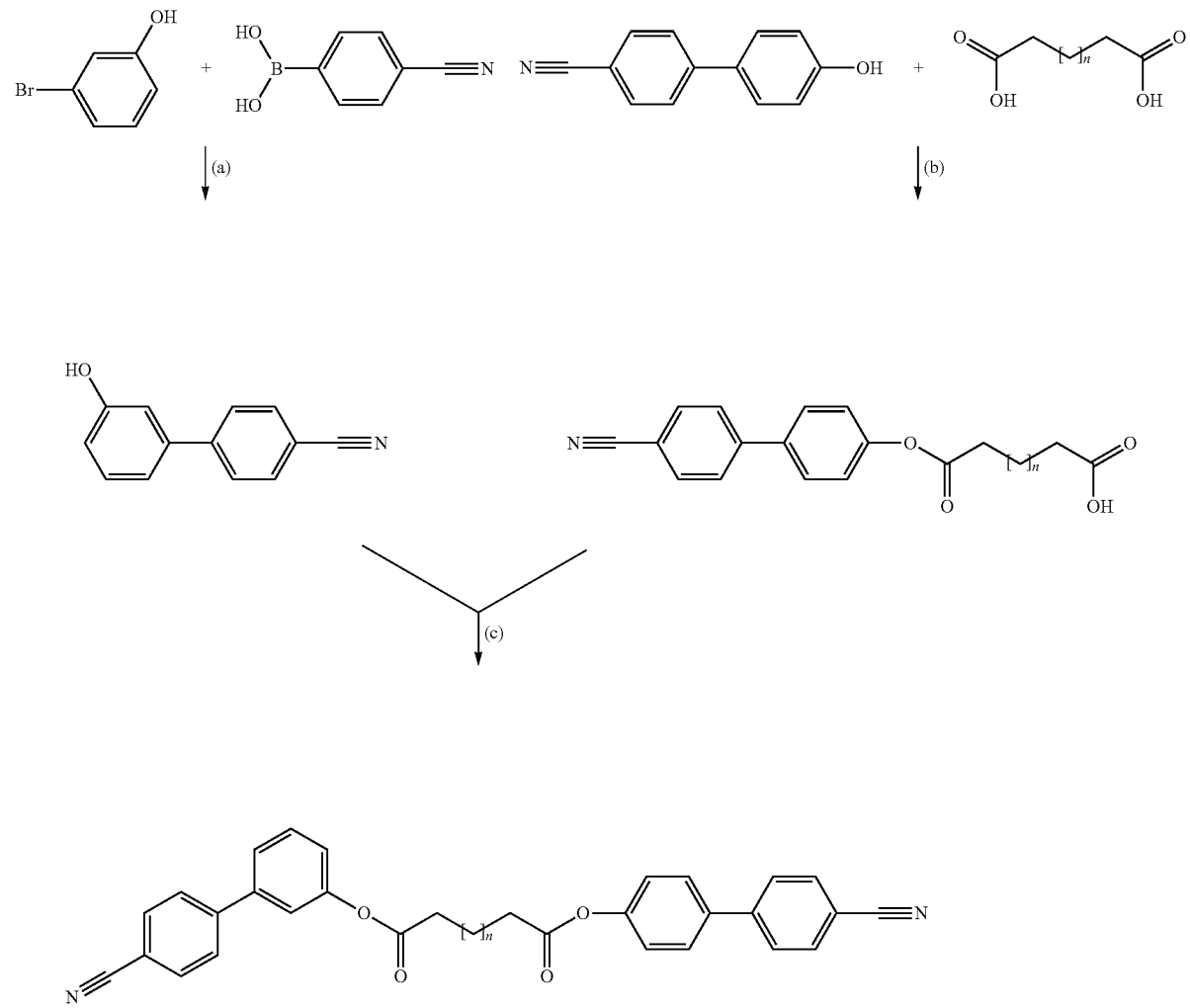

wherein n is an integer of 0, 1, 2, 3, 4 or from 5 to 15, preferably 3, 4, 5, 6, 7 or 8 and the conditions of the successive reactions are as follows:
a) Pd(dppf)Cl$_2$, Na$_2$CO$_3$, H$_2$O, Dioxane;
b) DCC, DMAP, DCM; and
c) DCC, DMAP, DCM.

Reaction Scheme IV (Non-symmetrical compounds)

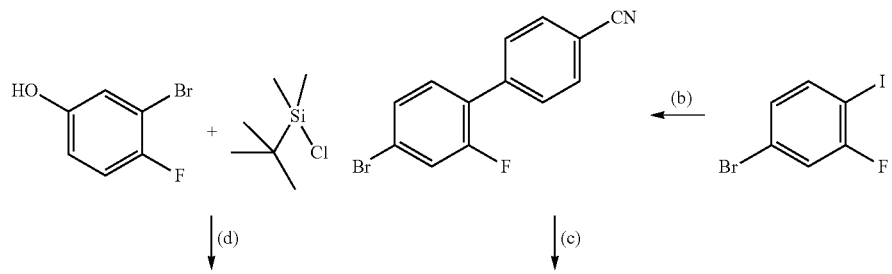

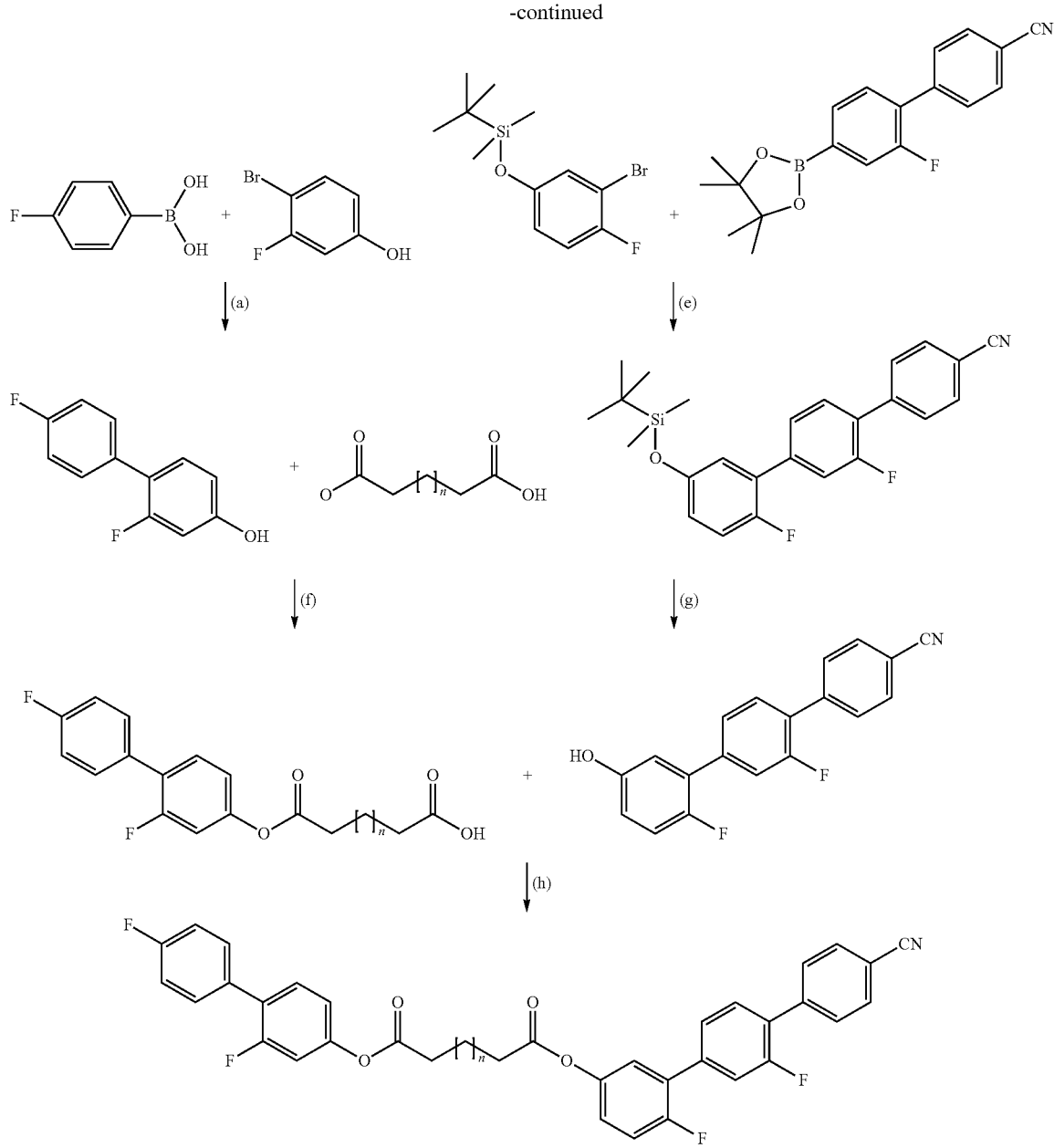

wherein n is an integer of of 0, 1 or from 2 to 15, preferably 3, 4, 5, 6, 7 or 8 and the conditions of the successive reactions are as follows:

a) Pd(dppf)Cl$_2$, Na$_2$CO$_3$, H$_2$O, Dioxane;
b) Pd(PPh$_3$)$_2$Cl$_2$, THF, NaCO$_3$, H$_2$O;
c) Pd(dppf)Cl$_2$, K$_2$CO$_3$, THF;
d) (C$_2$H$_5$)$_3$N, THF;
e) Pd(PPh$_3$)$_4$, K$_3$PO$_4$, Dioxane;
f) TFAA, DCM;
g) TBAF, THF; and
h) TFAA, DCM.

Another object of the invention is the use of compounds of formula I, preferably of bimesogenic compounds of formula I in liquid crystalline media.

Compounds of formula I, when added to a nematic liquid crystalline mixture, producing a phase below the nematic. In this context, a first indication of the influence of bimesogenic compounds on nematic liquid crystal mixtures was reported by Barnes, P. J., Douglas, A. G., Heeks, S. K., Luckhurst, G. R., Liquid Crystals, 1993, Vol.13, No.4, 603-613. This reference exemplifies highly polar alkyl spacered dimers and perceives a phase below the nematic, concluding it is a type of smectic.

A photo evidence of an existing mesophase below the nematic phase was published by Henderson, P. A., Niemeyer, O., Imrie, C. T. in Liquid Crystals, 2001, Vol. 28, No.3, 463-472, which was not further investigated.

In Liquid Crystals, 2005, Vol. 32, No. 11-12, 1499-1513 Henderson, P. A., Seddon, J. M. and Imrie, C. T. reported, that the new phase below the nematic belonged in some special examples to a smectic C phase. A additional nematic phase below the first nematic was reported by Panov, V. P., Ngaraj, M., Vij, J. K., Panarin, Y. P., Kohlmeier, A., Tamba, M. G., Lewis, R. A. and Mehl, G. H. in Phys. Rev. Lett. 2010, 105, 1678011-1678014.

In this context, liquid crystal mixtures comprising the new and inventive, preferably bimesogenic compounds of formula I show also a novel mesophase that is being assigned as a second nematic phase. This mesophase exists at a lower temperature than the original nematic liquid crystalline phase and has been observed in the unique mixture concepts presented by this application.

Accordingly, the preferably bimesogenic compounds of formula I according to the present invention allow the second nematic phase to be induced in nematic mixtures that do not have this phase normally. Furthermore, varying the amounts of compounds of formula I allow the phase behaviour of the second nematic to be tailored to the required temperature.

The invention thus relates to a liquid-crystalline medium which comprises at least one compound of the formula I.

Some preferred embodiments of the mixtures according to the invention are indicated below.

Preferred are compounds of formula I wherein the cyclic or mesogenic groups $MG^{11}$ and $MG^{12}$ at each occurrence independently from each other comprise one, two or three six-membered rings, preferably two or three six-membered rings.

Particularly preferred are the partial formulae II-1, II-4, II-6, II-7, II-13, II-14, II-15, II-16, II-17 and II-18.

Preferably $R^{11}$ and $R^{12}$ in formula I are selected of H, F, Cl, CN, $NO_2$, $OCH_3$, $COCH_3$, $COC_2H_5$, $COOCH_3$, $COOC_2H_5$, $CF_3$, $C_2F_5$, $OCF_3$, $OCHF_2$, and $OC_2F_5$, in particular of H, F, Cl, CN, $OCH_3$ and $OCF_3$, especially of H, F, CN and $OCF_3$.

The media according to the invention preferably comprise one, two, three, four or more, preferably one, two or three, compounds of the formula I.

The amount of compounds of formula I in the liquid crystalline medium is preferably from 1 to 50%, in particular from 5 to 40%, very preferably 10 to 30% by weight of the total mixture.

In a preferred embodiment the liquid crystalline medium according to the present invention comprises additionally one or more compounds of formula III, like those or similar to those known from GB 2 356 629.

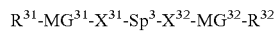

$$R^{31}\text{-}MG^{31}\text{-}X^{31}\text{-}Sp^3\text{-}X^{32}\text{-}MG^{32}\text{-}R^{32} \qquad \qquad III$$

wherein
$R^{31}$ and $R^{32}$ are each independently H, F, Cl, CN, NCS or a straight-chain or branched alkyl group with 1 to 25 C atoms which may be unsubstituted, mono- or polysubstituted by halogen or CN, it being also possible for one or more non-adjacent $CH_2$ groups to be replaced, in each case independently from one another, by —O—, —S—, —NH—, —N($CH_3$)—, —CO—, —COO—, —OCO—, —O—CO—O—, —S—CO—, —CO—S—, —CH=CH—, —CH=CF—, —CF=CF— or —C≡C— in such a manner that oxygen atoms are not linked directly to one another,
halogen preferably is F, or Cl, more preferably F,
$MG^{31}$ and $MG^{32}$ are each independently a mesogenic group,
$Sp^3$ is a spacer group comprising 5 to 40 C atoms, wherein one or more non-adjacent $CH_2$ groups may also be replaced by —O—, —S—, —NH—, —N($CH_3$)—, —CO—, —O—CO—, —S—CO—, —O—COO—, —CO—S—, —CO—O—, —CH(halogen)-, —CH (CN)—, —CH=CH— or —C≡C—, and
$X^{31}$ and $X^{32}$ are each independently —O—, —S—, —CO—, —COO—, —OCO—, —O—CO—O—, —CO—NH—, —NH—CO—, —$CH_2CH_2$—, —$OCH_2$—, —$CH_2O$—, —$SCH_2$—, —$CH_2S$—, —CH=CH—, —CH=CH—COO—, —OCO— CH=CH—, —C≡C— or a single bond.

The mesogenic groups $MG^{31}$ and $MG^{32}$ are preferably selected of formula II and preferably of its sub-formulae.

Especially preferred are compounds of formula III wherein $R^{31}$-$MG^{31}$-$X^{31}$— and $R^{32}$-$MG^{32}$-$X^{32}$— are identical.

Another preferred embodiment of the present invention relates to compounds of formula III wherein $R^{31}$-$MG^{31}$-$X^{31}$— and $R^{32}$-$MG^{32}$-$X^{32}$— are different.

Especially preferred are compounds of formula III wherein the mesogenic groups $MG^{31}$ and $MG^{32}$ comprise one, two or three six-membered rings very preferably are the mesogenic groups selected from formula II and, more preferably, of its sub-formulae, as listed below.

For $MG^{31}$ and $MG^{32}$ in formula III are particularly preferred are the sub-formulae II-1, II-4, II-5, II-8, II-15 and II-19. In these preferred groups Z in each case independently has one of the meanings of $Z^1$ as given in formula II. Preferably Z is —COO—, —OCO—, —$CH_2CH_2$—, —C≡C— or a single bond.

Very preferably the mesogenic groups $MG^{31}$ and $MG^{32}$ are selected from the formulae IIa to IIo and their mirror images.

In case of compounds with a non-polar group, $R^{31}$ and $R^{32}$ are preferably alkyl with up to 15 C atoms or alkoxy with 2 to 15 C atoms.

If $R^{31}$ or $R^{32}$ is an alkyl or alkoxy radical, i.e. where the terminal $CH_2$ group is replaced by —O—, this may be straight-chain or branched. It is preferably straight-chain, has 2, 3, 4, 5, 6, 7 or 8 carbon atoms and accordingly is preferably ethyl, propyl, butyl, pentyl, hexyl, heptyl, octyl, ethoxy, propoxy, butoxy, pentoxy, hexoxy, heptoxy, or octoxy, furthermore methyl, nonyl, decyl, undecyl, dodecyl, tridecyl, tetradecyl, pentadecyl, nonoxy, decoxy, undecoxy, dodecoxy, tridecoxy or tetradecoxy, for example.

Oxaalkyl, i.e. where one $CH_2$ group is replaced by —O—, is preferably straight-chain 2-oxapropyl(=methoxymethyl), 2-(=ethoxymethyl) or 3-oxabutyl(=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-,7-, 8- or 9-oxadecyl, for example.

In case of a compounds with a terminal polar group, $R^{31}$ and $R^{32}$ are selected from CN, $NO_2$, halogen, $OCH_3$, OCN, SCN, $COR^x$, $COOR^x$ or a mono- oligo- or polyfluorinated alkyl or alkoxy group with 1 to 4 C atoms. $R^x$ is optionally fluorinated alkyl with 1 to 4, preferably 1 to 3 C atoms. Halogen is preferably F or Cl, more preferably F.

Especially preferably $R^{31}$ and $R^{32}$ in formula III are selected of F, Cl, CN, $NO_2$, $OCH_3$, $COCH_3$, $COC_2H_5$, $COOCH_3$, $COOC_2H_5$, $CF_3$, $C_2F_5$, $OCF_3$, $OCHF_2$, and $OC_2F_5$, in particular of F, Cl, CN, $OCH_3$ and $OCF_3$.

As for the spacer group $Sp^3$ in formula III all groups can be used that are known for this purpose to the skilled in the art. The spacer group Sp is preferably a linear or branched alkylene group having 5 to 40 C atoms, in particular 5 to 25 C atoms, very preferably 5 to 15 C atoms, in which, in addition, one or more non-adjacent $CH_2$ groups may be replaced by —O—, —S—, —NH—, —N($CH_3$)—, —CO—, —O—CO—, —S—CO—, —O—COO—, —CO—S—, —CO—O—, —CH(halogen)-, —CH(CN)—, —CH=CH— or —C≡C—.

Typical spacer groups for formula III are for example —$(CH_2)_o$—, —$(CH_2CH_2O)_p$—$CH_2CH_2$—, —$CH_2CH_2$—S—$CH_2CH_2$— or —$CH_2CH_2$—NH—$CH_2CH_2$—, with o being an integer from 5 to 40, in particular from 5 to 25, very preferably from 5 to 15, and p being an integer from 1 to 8, in particular 1, 2, 3 or 4.

Preferred spacer groups are pentylene, hexylene, heptylene, octylene, nonylene, decylene, undecylene, dodecylene, octadecylene, diethyleneoxyethylene, dimethyleneoxybutylene, pentenylene, heptenylene, nonenylene and undecenylene, for example.

Especially preferred are inventive compounds of formula III wherein $Sp^3$ is denoting alkylene with 5 to 15 C atoms. Straight-chain alkylene groups are especially preferred.

In another preferred embodiment of the invention the chiral compounds of formula III comprise at least one spacer group $Sp^1$ that is a chiral group of the formula IV.

$X^{31}$ and $X^{32}$ in formula III denote preferably —O—, —CO—, —COO—, —OCO—, —O—CO—O— or a single bond. Particularly preferred are the following compounds selected from formulae III-1 to III-4 each other preferably F, Cl, CN, OH, $NO_2$ or an optionally fluorinated alkyl, alkoxy or alkanoyl group with 1 to 7 C atoms, very preferably F, Cl, CN, OH, $NO_2$, $CH_3$, $C_2H_5$, $OCH_3$, $OC_2H_5$, $COCH_3$, $COC_2H_5$, $COOCH_3$, $COOC_2H_5$, $CF_3$, $OCF_3$, $OCHF_2$, $OC_2F_5$, in particular F, Cl, CN, $CH_3$, $C_2H_5$, $OCH_3$, $COCH_3$ and $OCF_3$, most preferably F, Cl,

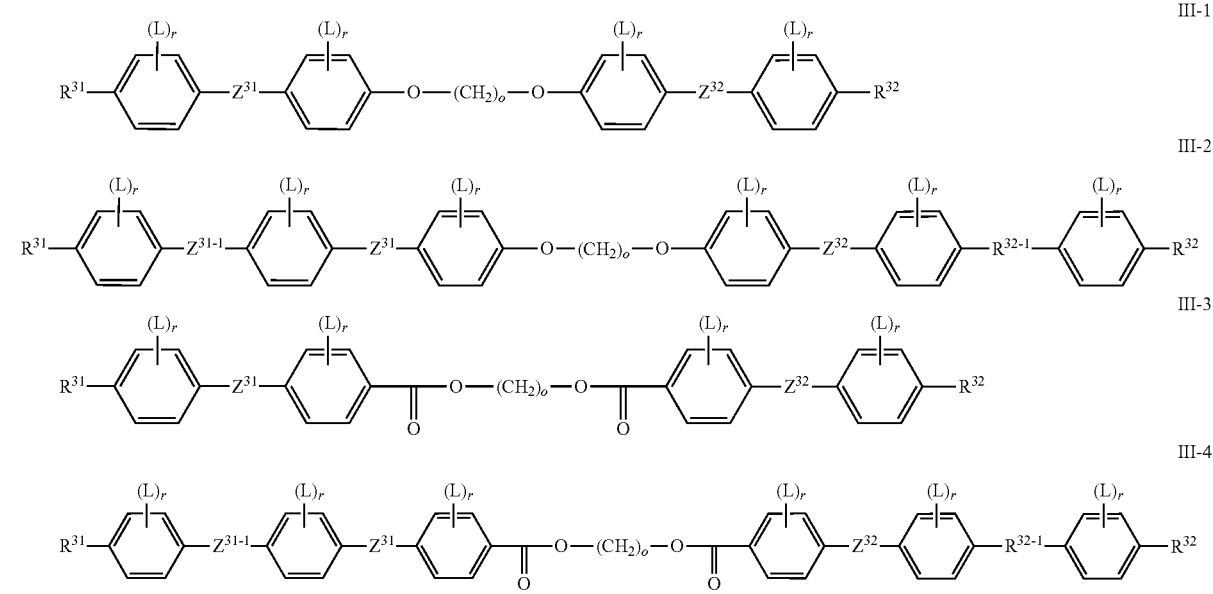

wherein $R^{31}$, $R^{32}$ have the meaning given under formula III, $Z^{31}$ and $Z^{31-I}$ are defined as $Z^{31}$ and $Z^{32}$ and $Z^{32-I}$ are respectively the reverse groups of $Z^{31}$ and $Z^{32-I}$ in formula III and o and r are independently at each occurrence as defined above, including the preferred meanings of these groups and wherein L is in each occurrence independently of $CH_3$, $OCH_3$ and $COCH_3$ and from which compounds of formula I are excluded.

Particularly preferred mixtures according to the invention comprise one or more compounds of the formulae III-1a to III-1e and III-3a to III-3b

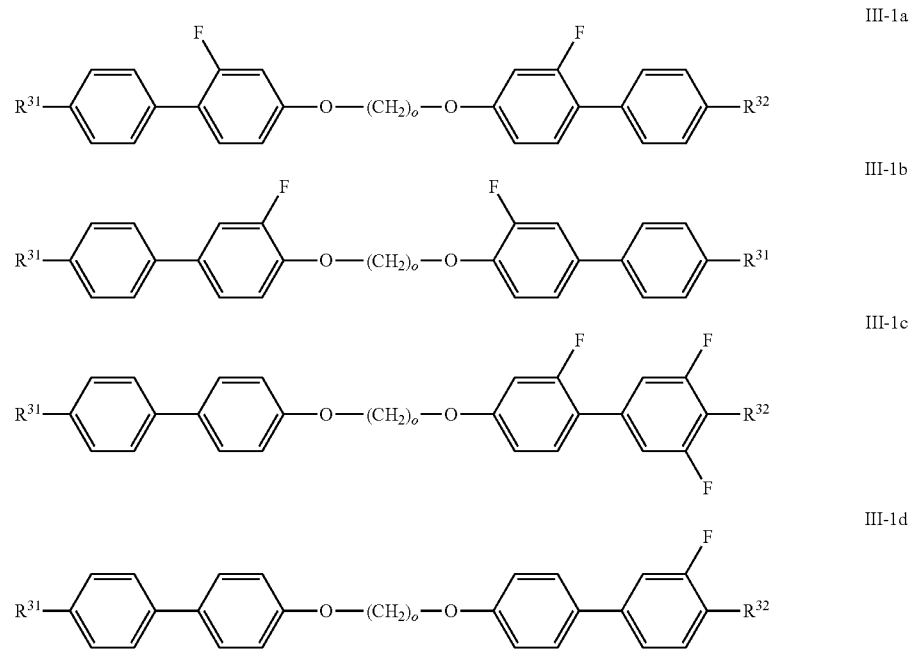

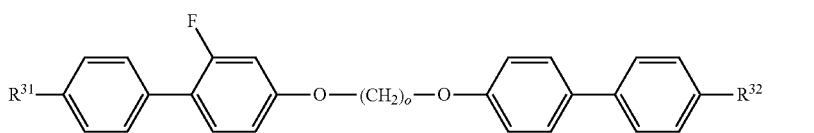

III-1e

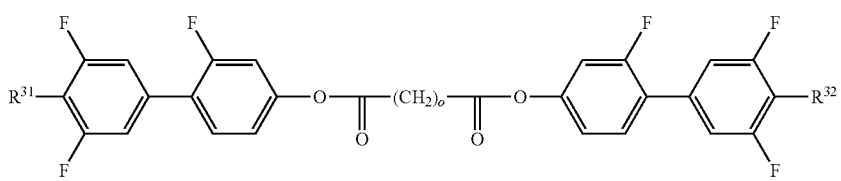

III-3a

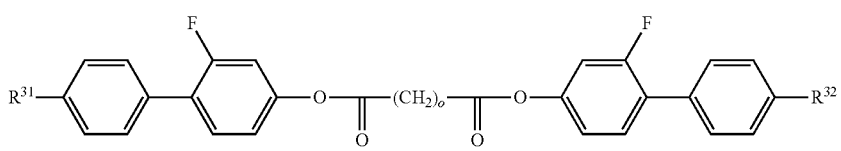

III-3b wherein the parameters are as defined above.

In a preferred embodiment of the invention the liquid crystalline medium is consisting of 2 to 25, preferably 3 to 15 compounds of formula III.

The amount of compounds of formula III in the liquid crystalline medium is preferably from 10 to 95%, in particular from 15 to 90%, very preferably 20 to 85% by weight of the total mixture.

Preferably, the proportion of compounds of the formulae III-1a and/or III-1b and/or III-1c and/or III-1e and or III-3a and/or III-3b in the medium as a whole is preferably at least 70% by weight.

Particularly preferred media according to the invention comprise at least one or more chiral dopants which themselves do not necessarily have to show a liquid crystalline phase and give good uniform alignment themselves.

Especially preferred are chiral dopants selected from formula IV wherein E and F are each independently 1,4-phenylene or trans-1,4-cyclo-hexylene, v is 0 or 1, $Z^0$ is —COO—, —OCO—, —CH$_2$CH$_2$— or a single bond, and R is alkyl, alkoxy or alkanoyl with 1 to 12 C atoms.

The compounds of formula IV and their synthesis are described in WO 98/00428. Especially preferred is the compound CD-1, as shown in table D below. The compounds of formula V and their synthesis are described in GB 2,328,207.

Especially preferred are chiral dopants with a high helical twisting power (HTP), in particular those disclosed in WO 98/00428.

Further typically used chiral dopants are e.g. the commercially available R/S-5011, CD-1, R/S-811 and CB-15 (from Merck KGaA, Darmstadt, Germany).

IV

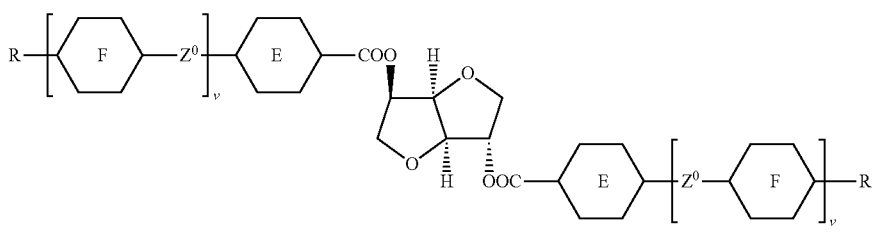

and formula V

V

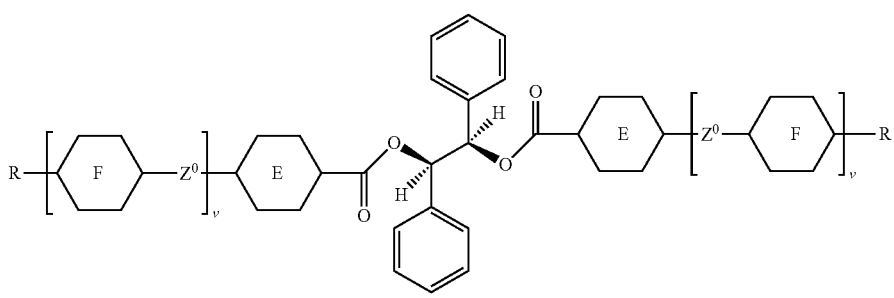

including the respective (S,S) enantiomer,

The above mentioned chiral compounds R/S-5011 and CD-1 and the compounds of formula IV and V exhibit a very high helical twisting power (HTP), and are therefore particularly useful for the purpose of the present invention.

The liquid crystalline medium preferably comprises preferably 1 to 5, in particular 1 to 3, very preferably 1 or 2 chiral dopants, preferably selected from the above formula IV, in particular CD-1, and/or formula V and/or R-5011 or S-5011, very preferably the chiral compound is R-5011, S-5011 or CD-1.

The amount of chiral compounds in the liquid crystalline medium is preferably from 1 to 20%, in particular from 1 to 15%, very preferably 1 to 10% by weight of the total mixture.

Further preferred are liquid crystalline media comprising one or more additives selected from the following formula VI

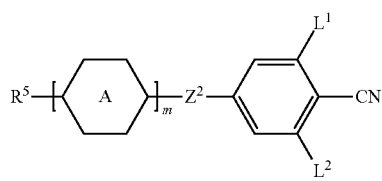

VI wherein
$R^5$ is alkyl, alkoxy, alkenyl or alkenyloxy with up to 12 C atoms,

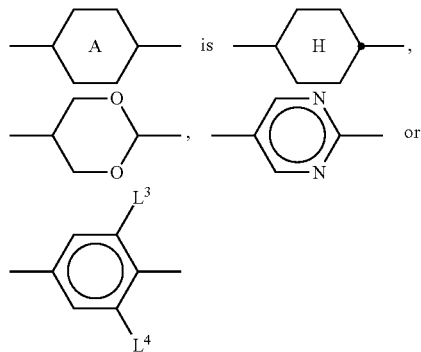

$L^1$ through $L^4$ are each independently H or F,
$Z^2$ is —COO—, —CH$_2$CH$_2$— or a single bond,
m is 1 or 2.

Particularly preferred compounds of formula VI are selected from the following formulae

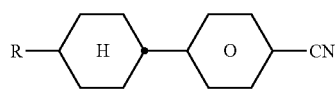

VIa

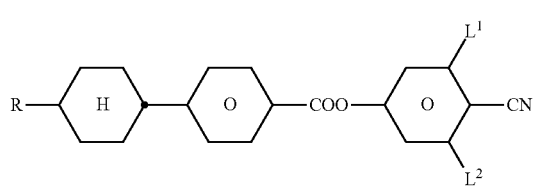

VIb

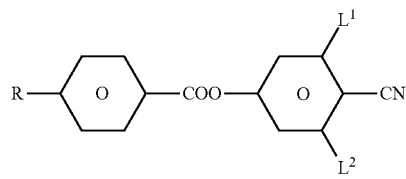

VIc

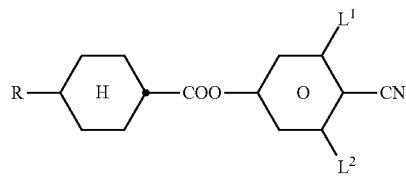

VId

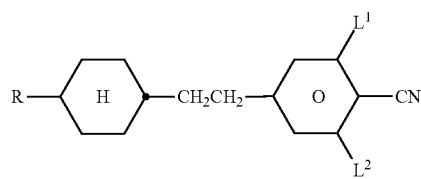

VIe

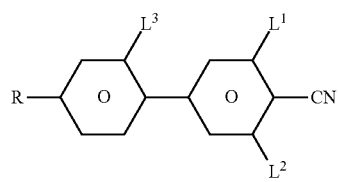

VIf wherein, R has one of the meanings of $R^5$ above and $L^1$, $L^2$ and $L^3$ have the above meanings.

The liquid crystalline medium preferably comprises preferably 1 to 5, in particular 1 to 3, very preferably 1 or 2, preferably selected from the above formulae VIa to VIf, very preferably from formulae VIf.

The amount of suitable additives of formula VI in the liquid crystalline medium is preferably from 1 to 20%, in particular from 1 to 15%, very preferably 1 to 10% by weight of the total mixture.

The liquid crystal media according to the present invention may contain further additives in usual concentrations. The total concentration of these further constituents is in the range of 0.1% to 10%, preferably 0.1% to 6%, based on the total mixture. The concentrations of the individual compounds used each are preferably in the range of 0.1% to 3%. The concentration of these and of similar additives is not taken into consideration for the values and ranges of the concentrations of the liquid crystal components and compounds of the liquid crystal media in this application. This also holds for the concentration of the dichroic dyes used in the mixtures, which are not counted when the concentrations of the compounds respectively the components of the host medium are specified. The concentration of the respective additives is always given relative to the final doped mixture.

The liquid crystal media according to the present invention consists of several compounds, preferably of 3 to 30, more preferably of 4 to 20 and most preferably of 4 to 16 compounds. These compounds are mixed in conventional way. As a rule, the required amount of the compound used in the smaller amount is dissolved in the compound used in the greater amount. In case the temperature is above the clearing point of the compound used in the higher concentration, it is particularly easy to observe completion of the process of dissolution. It is, however, also possible to prepare the media by other conventional ways, e.g. using so called pre-mixtures, which can be e.g. homologous or eutectic mixtures of compounds or using so called multi-bottle-systems, the constituents of which are ready to use mixtures themselves.

Particularly preferred mixture concepts are indicated below: (the acronyms used are explained in Table A).

The mixtures according to the invention preferably comprise one or more compounds of formula I in a total concentration in the range from 1 to 50%, in particular from 5 to 40%, very preferably 10 to 30% by weight of the total mixture and/or one or more compounds of formula III in a total concentration in the range from 10 to 95%, in particular from 15 to 90%, very preferably 20 to 85% by weight of the total mixture, preferably these compounds are selected from formulae III-1a to III-1e and III-3a to III-3b especially preferred they comprise N-PGI-ZInZ-GP-N, preferably N-PGI-ZI7Z-GP-N and/or N-PGI-ZI9Z-GP-N preferably in concentrations >5%, in particular 10-30%, based on the mixture as a whole, and/or F-UIGI-ZInZ-GU-F, preferably F-UIGI-ZI9Z-GU-F, preferably in concentrations >5%, in particular 10-30%, based on the mixture as a whole, and/or F-PGI-OnO-PP-N, preferably F-PGI-O9O-PP-, preferably in concentrations of >1%, in particular 1-20%, based on the mixture as a whole, and/or N-PP-OnO-PG-OT, preferably N-PP-O7O-PG-OT, preferably in concentrations of >5%, in particular 5-30%, based on the mixture as a whole, and/or N-PP-OnO-GU-F, preferably N-PP-O9O-GU-F, preferably in concentrations of >1%, in particular 1-20%, based on the mixture as a whole, and/or F-PGI-OnO-GP-F, preferably F-PGI-O7O-GP-F and/or F-PGI-O9O-GP-F preferably in concentrations of >1%, in particular 1-20%, based on the mixture as a whole, and/or N-GIGIGI-n-GGG-N, in particular N-GIGIGI-9-GGG-N, preferably in concentration >5%, in particular 10-30%, based on the mixture as a whole, and/or N-PGI-n-GP-N, preferably N-PGI-9-GP-N, preferably in concentrations >5%, in particular 15-50%, based on the mixture as a whole, and/or one or more suitable additives of formula VI in a total concentration in the range from 1 to 20%, in particular from 1 to 15%, very preferably 1 to 10% by weight of the total mixture, preferably are these compounds selected from formula VIa to VIf, especially preferred they comprise PP-n-N, preferably in concentrations of >1%, in particular 1-20%, based on the mixture as a whole, and/or one or more chiral compounds preferably in a total concentration in the range from 1 to 20%, in particular from 1 to 15%, very preferably 1 to 10% by weight of the total mixture, preferably these compounds are selected from formula IV, V, and R-5011 or S-5011, especially preferred they comprise R-5011, S-5011 or CD-1, preferably in a concentration of >1%, in particular 1-20%, based on the mixture as a whole.

The preferably bimesogenic compounds of formula I and the liquid crystalline media comprising them can be used in liquid crystal displays, such as STN, TN, AMD-TN, temperature compensation, guest-host, phase change or surface stabilized or polymer stabilized cholesteric texture (SSCT, PSCT) displays, in particular in flexoelectric devices, in active and passive optical elements like polarizers, compensators, reflectors, alignment layers, color filters or holographic elements, in adhesives, synthetic resins with anisotropic mechanical properties, cosmetics, diagnostics, liquid crystal pigments, for decorative and security applications, in nonlinear optics, optical information storage or as chiral dopants.

The compounds of formula I and the mixtures obtainable thereof are particularly useful for flexoelectric liquid crystal display. Thus, another object of the present invention is a flexoelectric display comprising one or more compounds of formula I or comprising a liquid crystal medium comprising one or more compounds of formula I.

The inventive, preferably bimesogenic, compounds of formula I and the mixtures thereof can be aligned in their cholesteric phase into different states of orientation by methods that are known to the expert, such as surface treatment or electric fields. For example, they can be aligned into the planar (Grandjean) state, into the focal conic state or into the homeotropic state. Inventive compounds of formula I comprising polar groups with a strong dipole moment can further be subjected to flexoelectric switching, and can thus be used in electrooptical switches or liquid crystal displays.

The switching between different states of orientation according to a preferred embodiment of the present invention is exemplarily described below in detail for a sample of an inventive compound of formula I.

According to this preferred embodiment, the sample is placed into a cell comprising two plane-parallel glass plates coated with electrode layers, e.g. ITO layers, and aligned in its cholesteric phase into a planar state wherein the axis of the cholesteric helix is oriented normal to the cell walls. This state is also known as Grandjean state, and the texture of the sample, which is observable e.g. in a polarization microscope, as Grandjean texture. Planar alignment can be achieved e.g. by surface treatment of the cell walls, for example by rubbing and/or coating with an alignment layer such as polyimide.

A Grandjean state with a high quality of alignment and only few defects can further be achieved by heating the sample to the isotropic phase, subsequently cooling to the chiral nematic phase at a temperature close to the chiral nematic-isotropic phase transition, and rubbing the cell.

In the planar state, the sample shows selective reflection of incident light, with the central wavelength of reflection depending on the helical pitch and the mean refractive index of the material.

When an electric field is applied to the electrodes, for example with a frequency from 10 Hz to 1 kHz, and an amplitude of up to 12 $V_{rms}/\Box m$, the sample is being switched into a homeotropic state where the helix is unwound and the molecules are oriented parallel to the field, i.e. normal to the plane of the electrodes. In the homeotropic state, the sample is transmissive when viewed in normal daylight, and appears black when being put between crossed polarizers.

Upon reduction or removal of the electric field in the homeotropic state, the sample adopts a focal conic texture, where the molecules exhibit a helically twisted structure with the helical axis being oriented perpendicular to the field, i.e. parallel to the plane of the electrodes. A focal conic state can also be achieved by applying only a weak electric field to a sample in its planar state. In the focal conic state the sample is scattering when viewed in normal daylight and appears bright between crossed polarizers.

A sample of an inventive compound in the different states of orientation exhibits different transmission of light. Therefore, the respective state of orientation, as well as its quality of alignment, can be controlled by measuring the light transmission of the sample depending on the strength of the applied electric field. Thereby it is also possible to determine the electric field strength required to achieve specific states of orientation and transitions between these different states.

In a sample of an inventive compound of formula I, the above described focal conic state consists of many disordered birefringent small domains. By applying an electric field greater than the field for nucleation of the focal conic texture, preferably with additional shearing of the cell, a uniformly aligned texture is achieved where the helical axis is parallel to the plane of the electrodes in large, well-aligned areas. In accordance with the literature on state of the art chiral nematic materials, such as P. Rudquist et al., Liq. Cryst. 23 (4), 503 (1997), this texture is also called uniformly-lying helix (ULH) texture. This texture is required to characterize the flexoelectric properties of the inventive compound.

The sequence of textures typically observed in a sample of an inventive compound of formula I on a rubbed polyimide substrate upon increasing or decreasing electric field is given below:

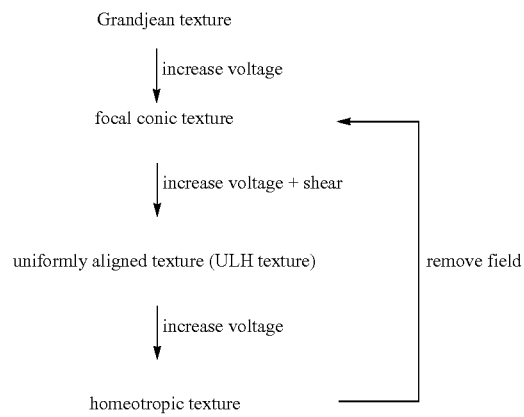

Starting from the ULH texture, the inventive flexoelectric compounds and mixtures can be subjected to flexoelectric switching by application of an electric field. This causes rotation of the optic axis of the material in the plane of the cell substrates, which leads to a change in transmission when placing the material between crossed polarizers. The flexoelectric switching of inventive materials is further described in detail in the introduction above and in the examples.

It is also possible to obtain the ULH texture, starting from the focal conic texture, by applying an electric field with a high frequency, of for example 10 kHz, to the sample whilst cooling slowly from the isotropic phase into the cholesteric phase and shearing the cell. The field frequency may differ for different compounds.

The, preferably bimesogenic, compounds of formula I are particularly useful in flexoelectric liquid crystal displays as they can easily be aligned into macroscopically uniform orientation, and lead to high values of the elastic constant $k_{11}$ and a high flexoelectric coefficient e in the liquid crystal medium.

The liquid crystal medium preferably exhibits a $k_{11} < 1 \times 10^{-10}$ N, preferably $< 2 \times 10^{-11}$ N, and a flexoelectric coefficient $e > 1 \times 10^{-11}$ C/m, preferably $> 1 \times 10^{-10}$ C/m.

Apart from the use in flexoelectric devices, the inventive bimesogenic compounds as well as mixtures thereof are also suitable for other types of displays and other optical and electrooptical applications, such as optical compensation or polarizing films, color filters, reflective cholesterics, optical rotatory power and optical information storage.

A further aspect of the present invention relates to a display cell wherein the cell walls exhibit hybrid alignment conditions. The term "hybrid alignment" or orientation of a liquid crystal or mesogenic material in a display cell or between two substrates means that the mesogenic groups adjacent to the first cell wall or on the first substrate exhibit homeotropic orientation and the mesogenic groups adjacent to the second cell wall or on the second substrate exhibit planar orientation.

The term "homeotropic alignment" or orientation of a liquid crystal or mesogenic material in a display cell or on a substrate means that the mesogenic groups in the liquid crystal or mesogenic material are oriented substantially perpendicular to the plane of the cell or substrate, respectively.

The term "planar alignment" or orientation of a liquid crystal or mesogenic material in a display cell or on a substrate means that the mesogenic groups in the liquid crystal or mesogenic material are oriented substantially parallel to the plane of the cell or substrate, respectively.

A flexoelectric display according to a preferred embodiment of the present invention comprises two plane parallel substrates, preferably glass plates covered with a transparent conductive layer such as indium tin oxide (ITO) on their inner surfaces, and a flexoelectric liquid crystalline medium provided between the substrates, characterized in that one of the inner substrate surfaces exhibits homeotropic alignment conditions and the opposite inner substrate surface exhibits planar alignment conditions for the liquid crystalline medium.

Planar alignment can be achieved e.g. by means of an alignment layer, for example a layer of rubbed polyimide or sputtered $SiO_x$, that is applied on top of the substrate.

Alternatively it is possible to directly rub the substrate, i.e. without applying an additional alignment layer. For example, rubbing can be achieved by means of a rubbing cloth, such as a velvet cloth, or with a flat bar coated with a rubbing cloth. In a preferred embodiment of the present invention rubbing is achieved by means of a at least one rubbing roller, like e.g. a fast spinning roller that is brushing across the substrate, or by putting the substrate between at least two rollers, wherein in each case at least one of the rollers is optionally covered with a rubbing cloth. In another preferred embodiment of the present invention rubbing is achieved by wrapping the substrate at least partially at a defined angle around a roller that is preferably coated with a rubbing cloth.

Homeotropic alignment can be achieved e.g. by means of an alignment layer coated on top of the substrate. Suitable aligning agents used on glass substrates are for example alkyltrichlorosilane or lecithine, whereas for plastic substrate thin layers of lecithine, silica or high tilt polyimide orientation films as aligning agents may be used. In a preferred embodiment of the invention silica coated plastic film is used as a substrate.

Further suitable methods to achieve planar or homeotropic alignment are described for example in J. Cognard, Mol. Cryst. Liq. Cryst. 78, Supplement 1, 1-77 (1981).

By using a display cell with hybrid alignment conditions, a very high switching angle of flexoelectric switching, fast response times and a good contrast can be achieved.

The flexoelectric display according to present invention may also comprise plastic substrates instead of glass substrates. Plastic film substrates are particularly suitable for rubbing treatment by rubbing rollers as described above.

Another object of the present invention is that compounds of formula I, when added to a nematic liquid crystalline mixture, produce a phase at a temperature below that at which the nematic phase occurs.

Accordingly, the, preferably bimesogenic, compounds of formula I according to the present invention allow the second nematic phase to be induced in nematic mixtures that do not show evidence of this phase normally. Furthermore, varying the amounts of compounds of formula I allow the phase behaviour of the second nematic to be tailored to the required temperature.

Examples for this are given and the mixtures obtainable thereof are particularly useful for flexoelectric liquid crystal display. Thus, another object of the present invention is liquid crystal media comprising one or more compounds of formula I exhibiting a second nematic phase.

Without further elaboration, it is believed that one skilled in the art can, using the preceding description, utilize the present invention to its fullest extent. The following examples are, therefore, to be construed as merely illustrative and not limitative of the remainder of the disclosure in any way whatsoever.

Unless the context clearly indicates otherwise, as used herein plural forms of the terms herein are to be construed as including the singular form and vice versa.

Throughout the description and claims of this specification, the words "comprise" and "contain" and variations of the words, for example "comprising" and "comprises", mean "including but not limited to", and are not intended to (and do not) exclude other components.

Throughout the present application it is to be understood that the angles of the bonds at a C atom being bound to three adjacent atoms, e.g. in a C=C or C=O double bond or e.g. in a benzene ring, are 120° and that the angles of the bonds at a C atom being bound to two adjacent atoms, e.g. in a C≡C or in a C≡N triple bond or in an allylic position C=C=C are 180°, unless these angles are otherwise restricted, e.g. like being part of small rings, like 3-, 5- or 5-atomic rings, notwithstanding that in some instances in some structural formulae these angles are not represented exactly.

It will be appreciated that variations to the foregoing embodiments of the invention can be made while still falling within the scope of the invention. Each feature disclosed in this specification, unless stated otherwise, may be replaced by alternative features serving the same, equivalent or similar purpose. Thus, unless stated otherwise, each feature disclosed is one example only of a generic series of equivalent or similar features.

All of the features disclosed in this specification may be combined in any combination, except combinations where at least some of such features and/or steps are mutually exclusive. In particular, the preferred features of the invention are applicable to all aspects of the invention and may be used in any combination. Likewise, features described in non-essential combinations may be used separately (not in combination).

The total concentration of all compounds in the media according to this application is 100%.

In the foregoing and in the following examples, unless otherwise indicated, all temperatures are set forth uncorrected in degrees Celsius and all parts and percentages are by weight.

The following abbreviations are used to illustrate the liquid crystalline phase behavior of the compounds: K=crystalline; N=nematic; N2=second nematic; S or Sm=smectic; Ch=cholesteric; I=isotropic; Tg=glass transition. The numbers between the symbols indicate the phase transition temperatures in ° C.

In the present application and especially in the following examples, the structures of the liquid crystal compounds are represented by abbreviations, which are also called "acronyms". The transformation of the abbreviations into the corresponding structures is straight forward according to the following three tables A to C.

All groups $C_nH_{2n+1}$, $C_mH_{2m+1}$, and $C_lH2_{l+1}$ are preferably straight chain alkyl groups with n, m and l C-atoms, respectively, all groups $C_nH_{2n}$, $C_mH_{2m}$ and $C_lH_{2l}$ are preferably $(CH_2)_n$, $(CH_2)_m$ and $(CH_2)_l$, respectively and —CH=CH— preferably is trans-respectively E vinylene.

Table A lists the symbols used for the ring elements, table B those for the linking groups and table C those for the symbols for the left hand and the right hand end groups of the molecules.

Table D lists exemplary molecular structures together with their respective codes.

TABLE A

Ring Elements

| | | | |
|---|---|---|---|
| C | (cyclohexane) | P | (benzene) |
| D | (dioxane) | DI | (dioxane isomer) |
| A | (tetrahydropyran) | AI | (tetrahydropyran isomer) |
| G | (fluorobenzene) | GI | (fluorobenzene isomer) |
| G(Cl) | (chlorobenzene) | GI(Cl) | (chlorobenzene isomer) |

TABLE A-continued

Ring Elements

G(n)  (CH₂)ₙH  (n ∈ {1; 2; 3; 4; 5})
GI(n)  H(CH₂)ₙ  (n ∈ {1; 2; 3; 4; 5})
U
UI
Y
M
MI
N
NI
np
n3f
n3fI
th
thI
th2f
th2fI
o2f
o2fI
dh
K
KI
L
LI
F
FI

TABLE B

| | Linking Groups | | | |
|---|---|---|---|---|
| n | (—CH₂—)ₙ | "n" is an integer except 0 and 2 | | |
| E | —CH₂—CH₂— | | | |
| V | —CH═CH— | | | |
| T | —C≡C— | | | |
| W | —CF₂—CF₂— | | | |
| B | —CF═CF— | | | |
| Z | —CO—O— | | ZI | —O—CO— |
| X | —CF═CH— | | XI | —CH═CF— |
| 1O | —CH₂—O— | | O1 | —O—CH₂— |
| Q | —CF₂—O— | | QI | —O—CF₂— |

TABLE C

End Groups

| Left hand side, used alone or in combination with others | | Right hand side, used alone or in combination with others | |
|---|---|---|---|
| -n- | $C_nH_{2n+1}$— | -n | —$C_nH_{2n+1}$ |
| -nO- | $C_nH_{2n+1}$—O— | -nO | —O—$C_nH_{2n+1}$ |
| -V- | CH₂═CH— | -V | —CH═CH₂ |
| -nV- | $C_nH_{2n+1}$—CH═CH— | -nV | —$C_nH_{2n}$—CH═CH₂ |
| -Vn- | CH₂═CH—$C_nH_{2n}$— | -Vn | —CH═CH—$C_nH_{2n+1}$ |
| XX-nVm- | $C_nH_{2n+1}$—CH═CH—$C_mH_{2m}$— | -nVm | —$C_nH_{2n}$—CH═CH—$C_mH_{2m+1}$ |
| -N- | N≡C— | -N | —C≡N |
| -S- | S═C═N— | -S | —N═C═S |
| -F- | F— | -F | —F |
| -CL- | Cl— | -CL | —Cl |
| -M- | CFH₂— | -M | —CFH₂ |
| -D- | CF₂H— | -D | —CF₂H |
| -T- | CF₃— | -T | —CF₃ |

TABLE C-continued

End Groups

| | | | |
|---|---|---|---|
| -MO- | CFH$_2$O— | -OM | —OCFH$_2$ |
| -DO- | CF$_2$HO— | -OD | —OCF$_2$H |
| -TO- | CF$_3$O— | -OT | —OCF$_3$ |
| -A- | H—C≡C— | -A | —C≡C—H |
| -nA- | C$_n$H$_{2n+1}$—C≡C— | -An | —C≡C—C$_n$H$_{2n+1}$ |
| -NA- | N≡C—C≡C— | -AN | —C≡C—C≡N |

| Left hand side, used in combination with others only | | Right hand side, used in combination with others only | |
|---|---|---|---|
| -...n...- | (—CH$_2$—)$_n$ | -...n... | (—CH$_2$—)$_n$ |
| -...M...- | —CFH— | -...M... | —CFH— |
| -...D...- | —CF$_2$— | -...D... | —CF$_2$— |
| -...V...- | —CH=CH— | -...V... | —CH=CH— |
| -...Z...- | —CO—O— | -...Z... | —CO—O— |
| -...ZI...- | —O—CO— | -...ZI... | —O—CO— |
| -...K...- | —CO— | -...K... | —CO— |
| -...W...- | —CF=CF— | -...W... | —CF=CF— | wherein n und m each are integers and three points "..." indicate a space for other symbols of this table.

Preferably the liquid crystalline media according to the present invention comprise, besides the compound(s) of formula I one or more compounds selected from the group of compounds of the formulae of the following table.

In this table n is an integer selected from 3 and 5 to 15, preferably from 3, 5, 7 and 9, unless explicitly defined otherwise.

TABLE D

Chiral dopants

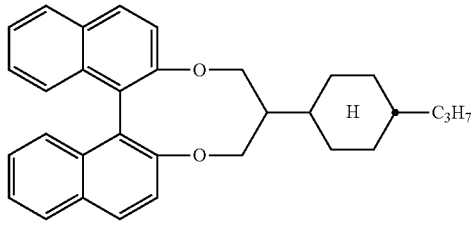

R-5011 respectively S-5011

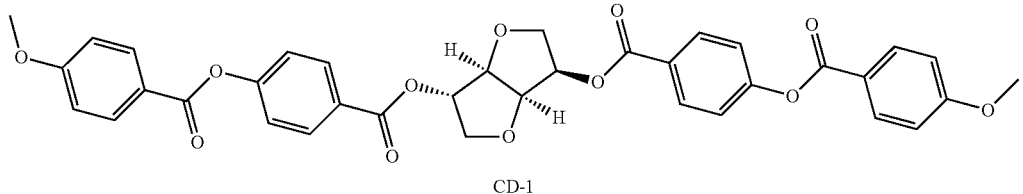

CD-1

Nematic or nematogenic compounds

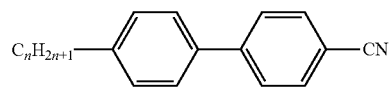

PP-n-N (n ∈ {2; 3; 4; 5; 6; 7})

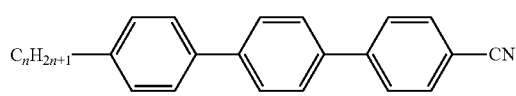

PPP-n-N (n ∈ {2; 3; 4; 5; 6; 7})

TABLE D-continued
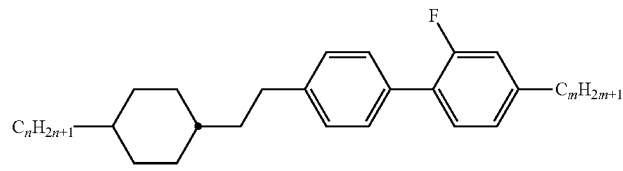
CC-n-V (n ∈ {2; 3; 4; 5; 7})
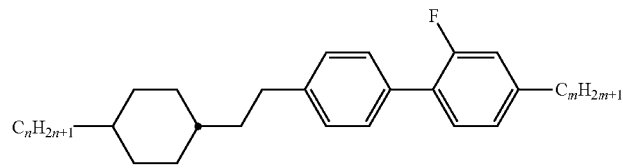
CEPGI-n-m (n ∈ {2; 3; 4; 5}, m ε {2; 3; 4; 5})
| Bimesogenic compounds |
|---|
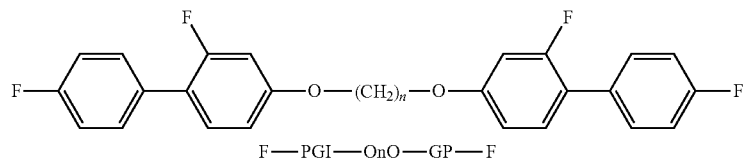
F—PGI—OnO—GP—F
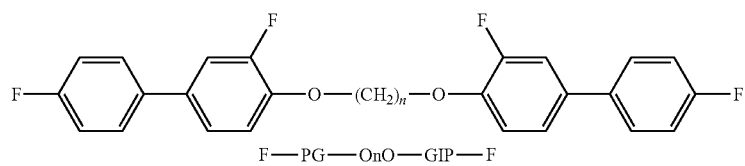
F—PG—OnO—GIP—F
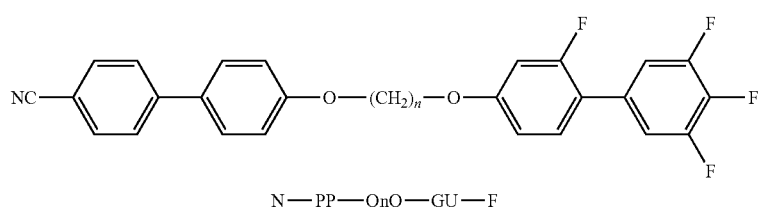
N—PP—OnO—GU—F
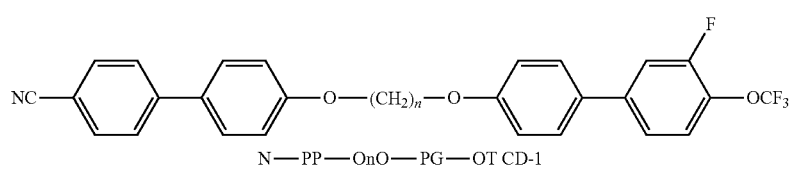
N—PP—OnO—PG—OT CD-1
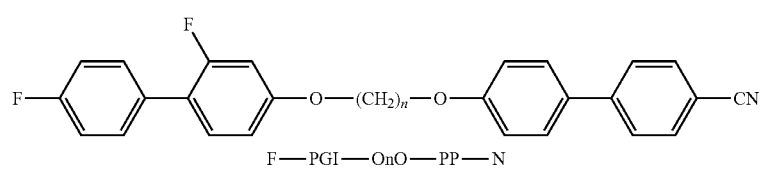
F—PGI—OnO—PP—N
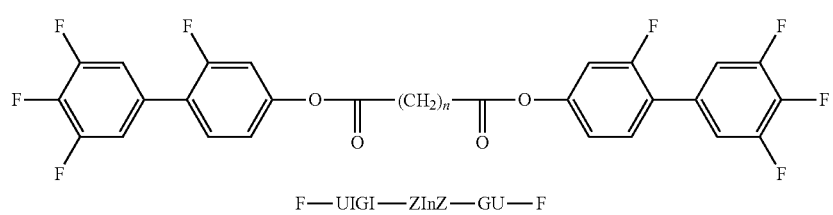
F—UIGI—ZInZ—GU—F TABLE D-continued
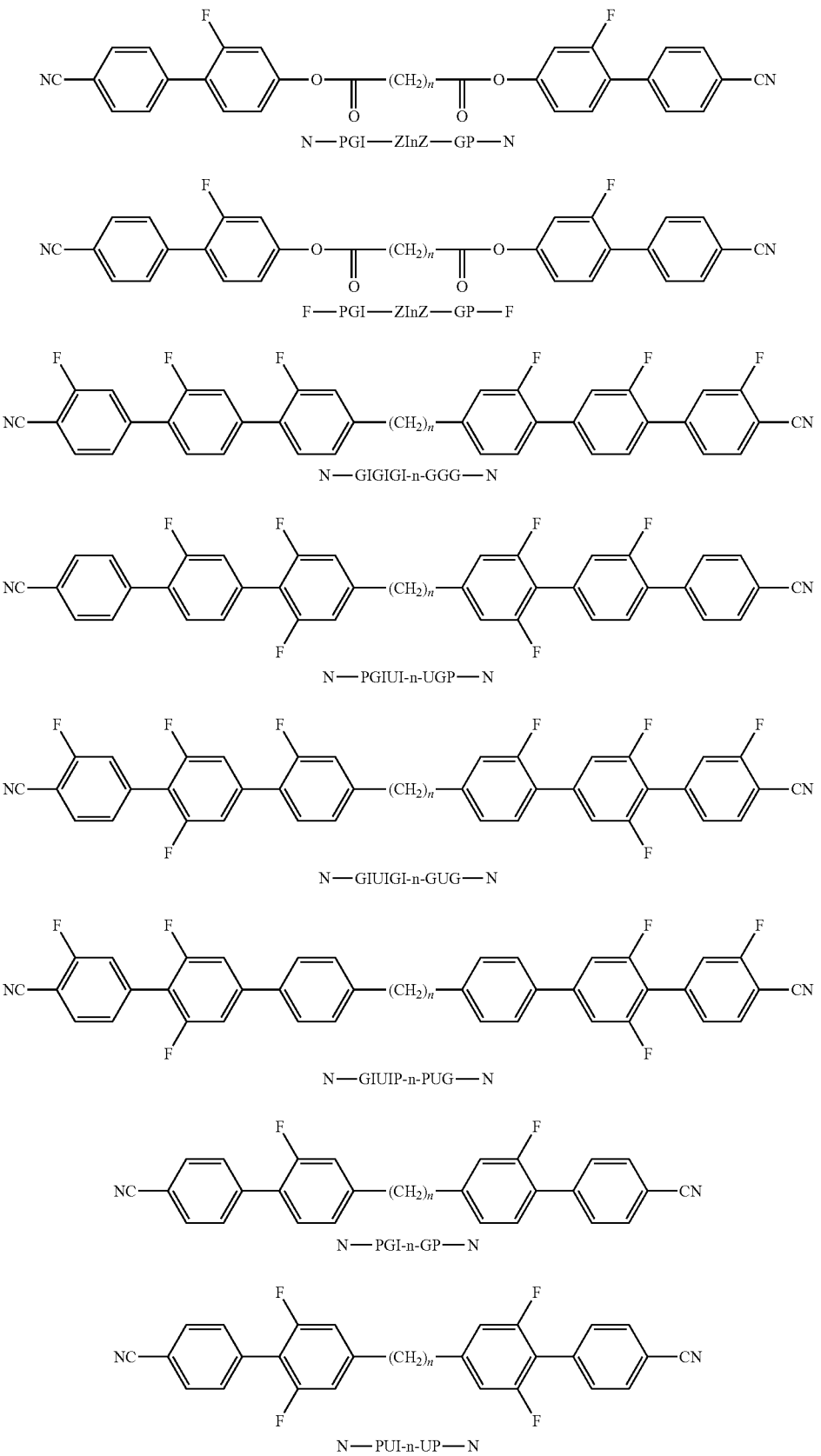

TABLE D-continued
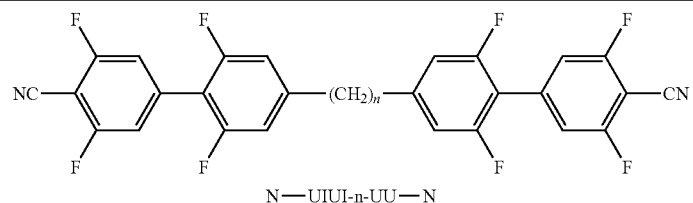
N—UIUI-n-UU—N
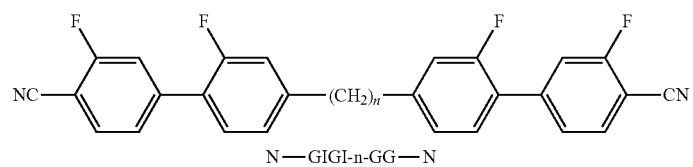
N—GIGI-n-GG—N
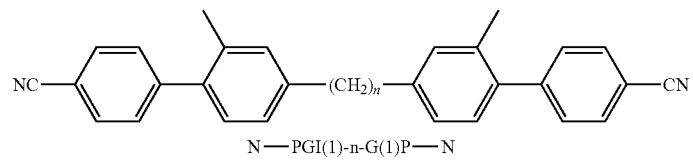
N—PGI(1)-n-G(1)P—N
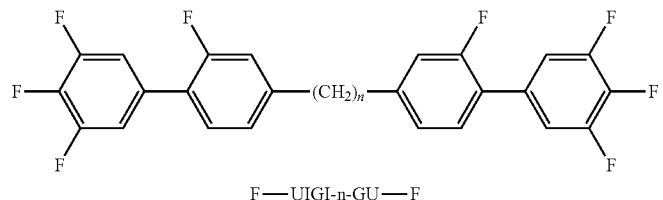
F—UIGI-n-GU—F
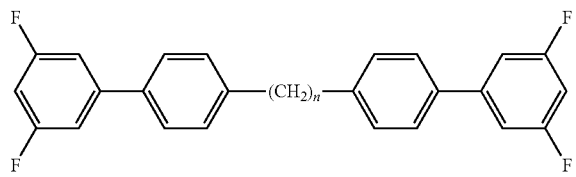
UIP-n-PU
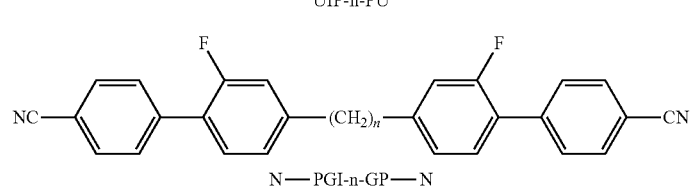
N—PGI-n-GP—N
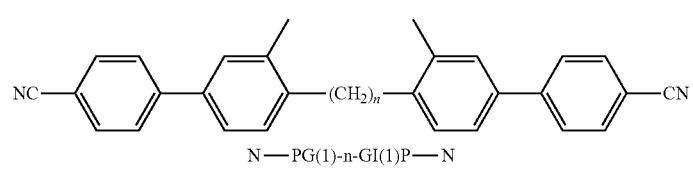
N—PG(1)-n-GI(1)P—N
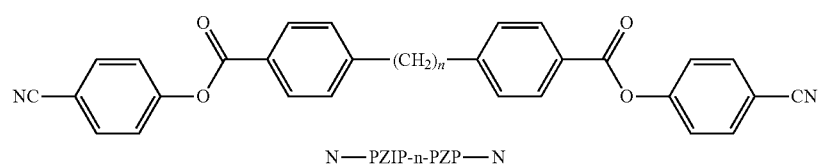
N—PZIP-n-PZP—N
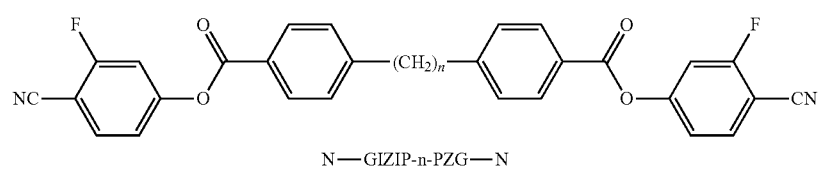
N—GIZIP-n-PZG—N TABLE D-continued
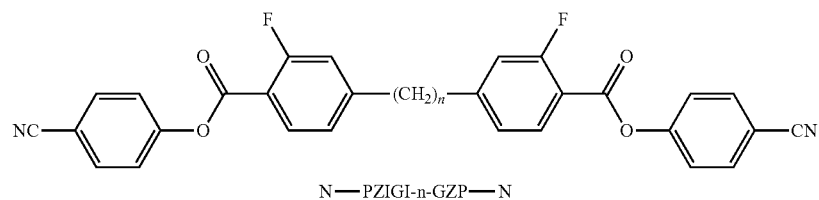
N—PZIGI-n-GZP—N
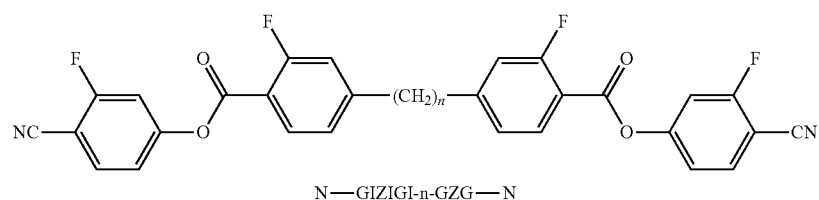
N—GIZIGI-n-GZG—N
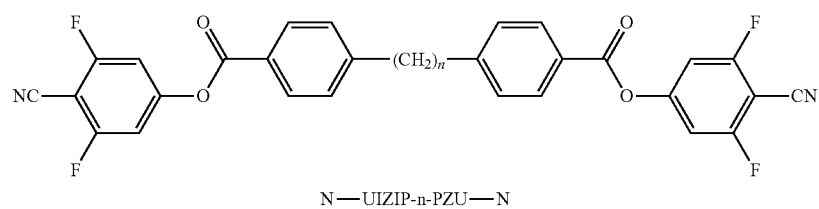
N—UIZIP-n-PZU—N
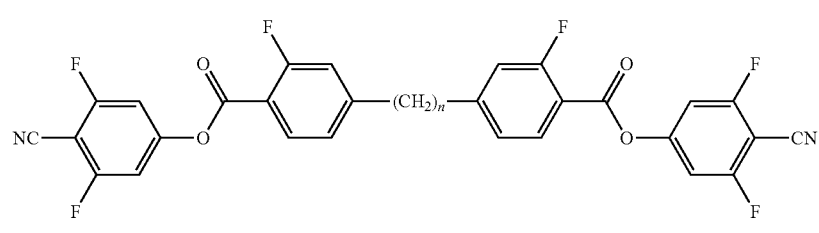
N—UIZIGI-n-GZU—N
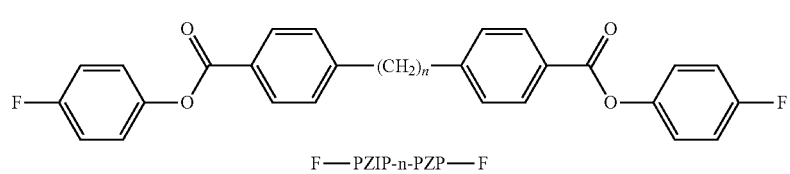
F—PZIP-n-PZP—F
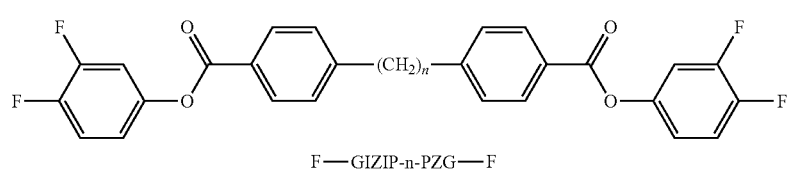
F—GIZIP-n-PZG—F
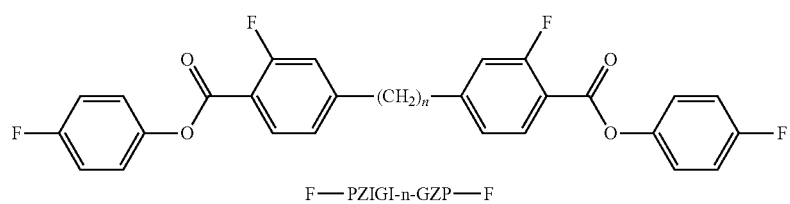
F—PZIGI-n-GZP—F
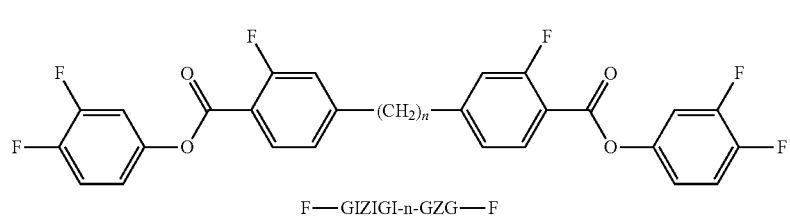
F—GIZIGI-n-GZG—F TABLE D-continued
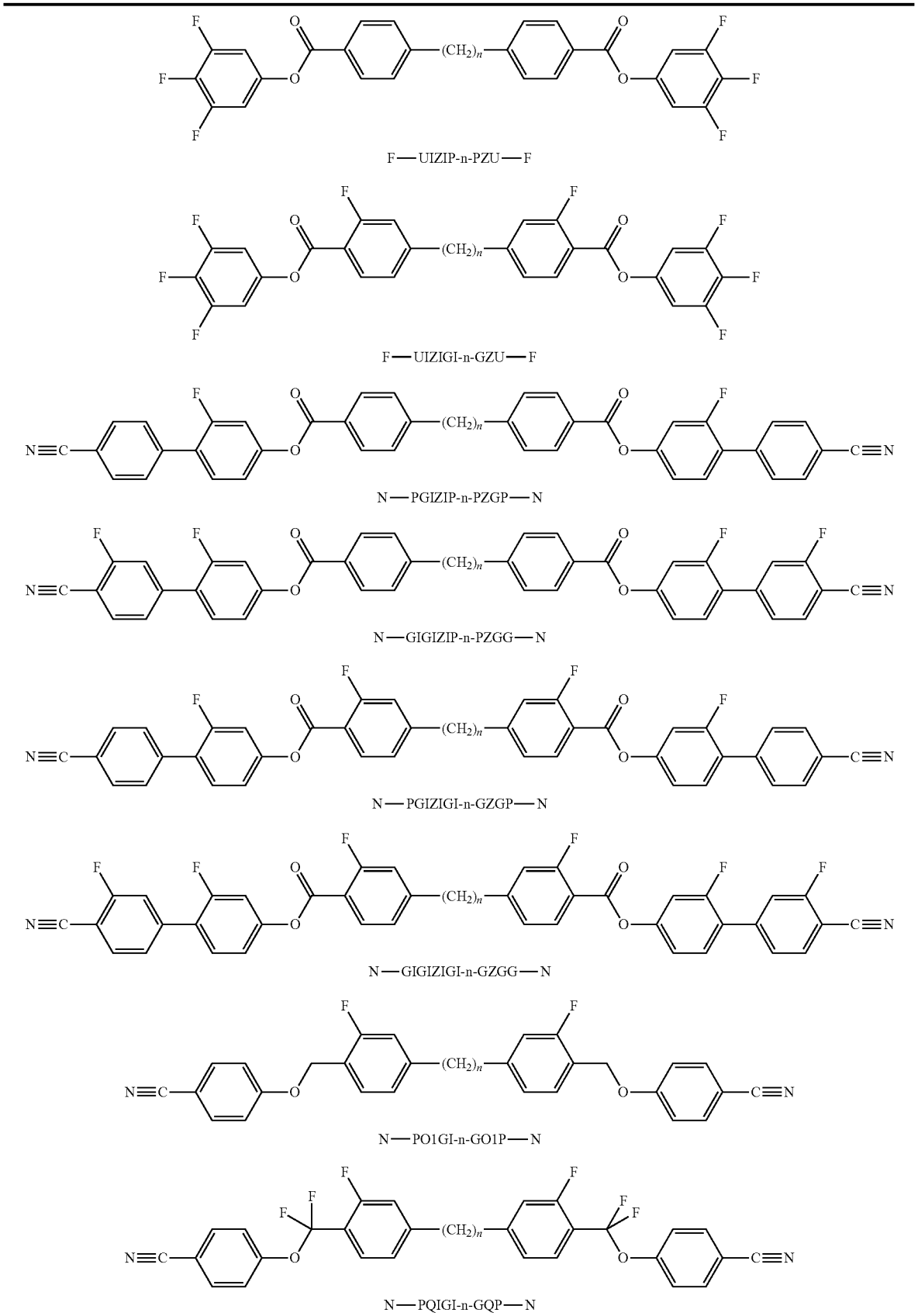

TABLE D-continued
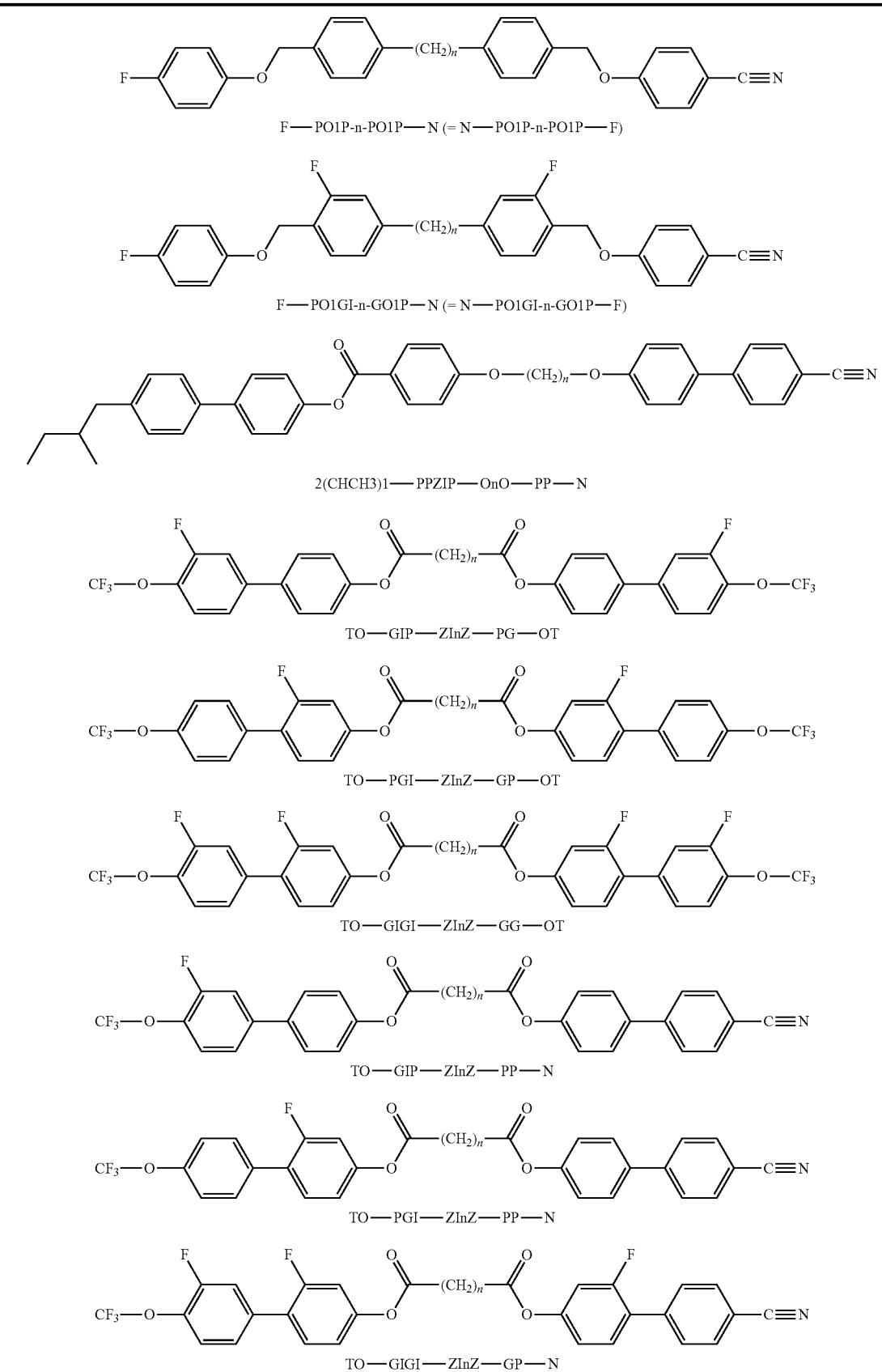

TABLE D-continued
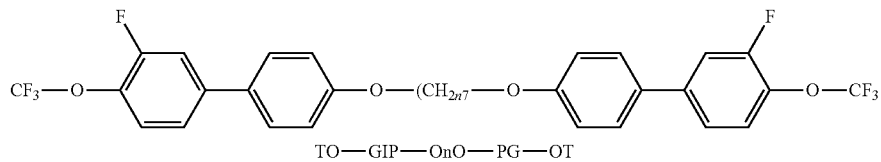
TO—GIP—OnO—PG—OT
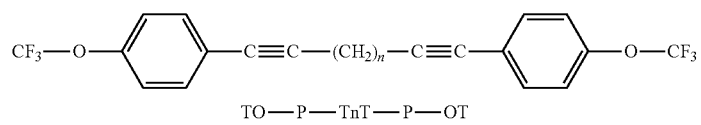
TO—P—TnT—P—OT
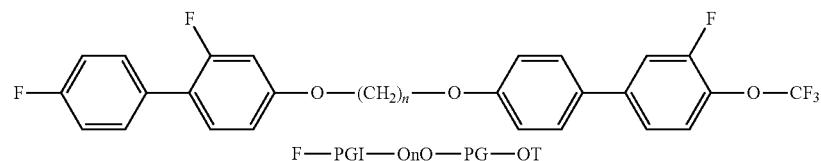
F—PGI—OnO—PG—OT
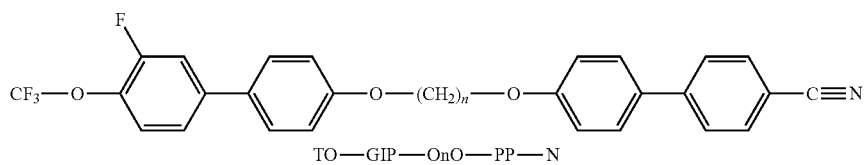
TO—GIP—OnO—PP—N
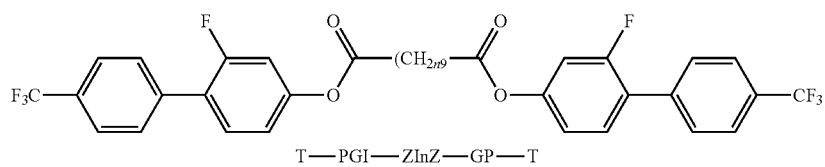
T—PGI—ZInZ—GP—T
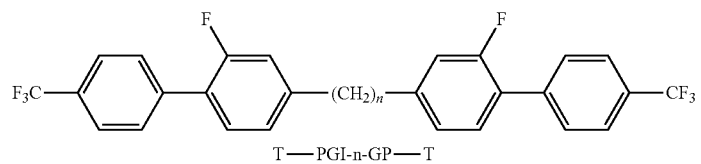
T—PGI-n-GP—T
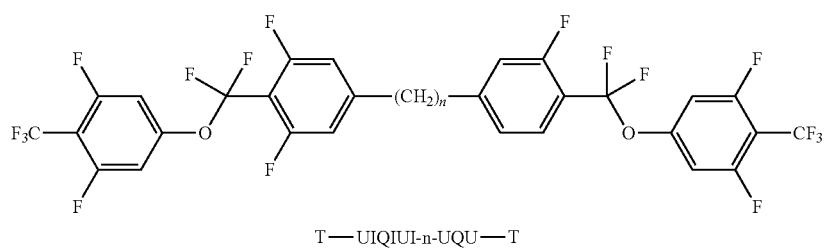
T—UIQIUI-n-UQU—T
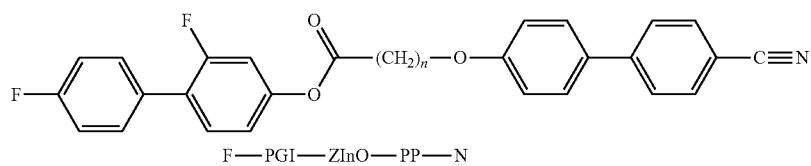
F—PGI—ZInO—PP—N
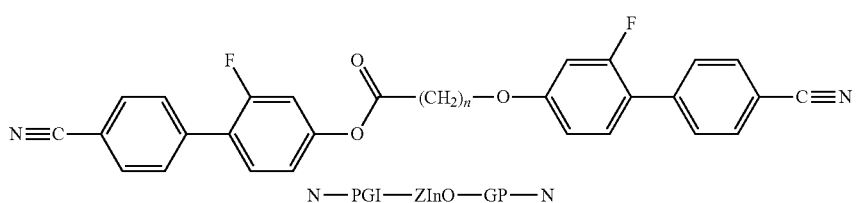
N—PGI—ZInO—GP—N TABLE D-continued
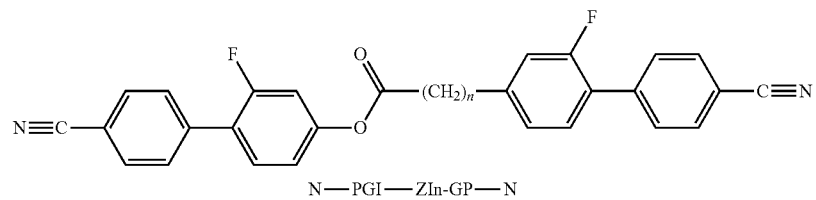
N—PGI—ZIn-GP—N
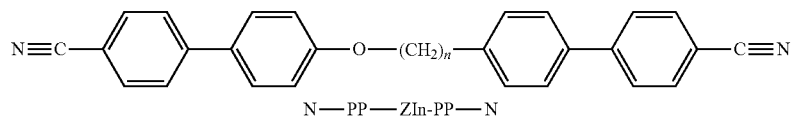
N—PP—ZIn-PP—N
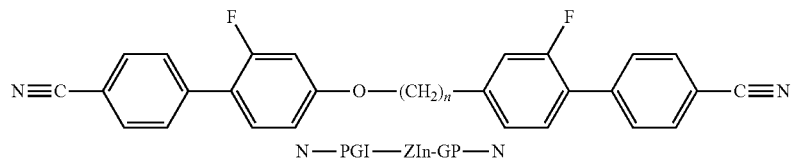
N—PGI—ZIn-GP—N
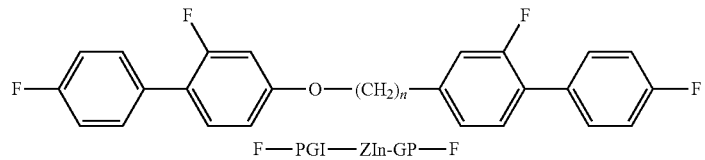
F—PGI—ZIn-GP—F
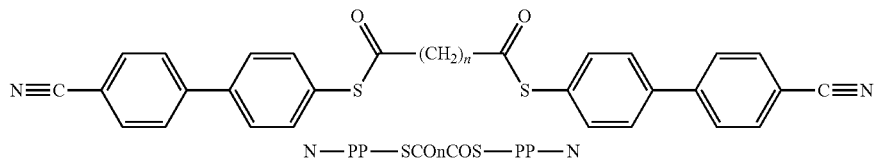
N—PP—SCOnCOS—PP—N
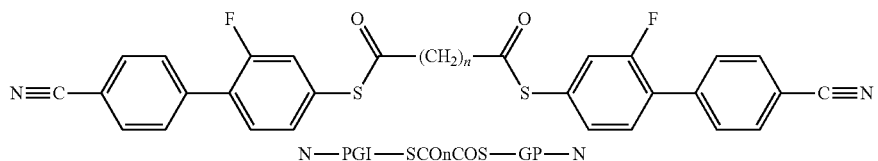
N—PGI—SCOnCOS—GP—N
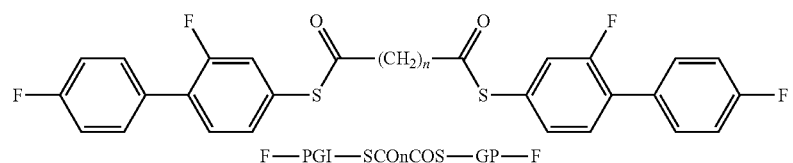
F—PGI—SCOnCOS—GP—F
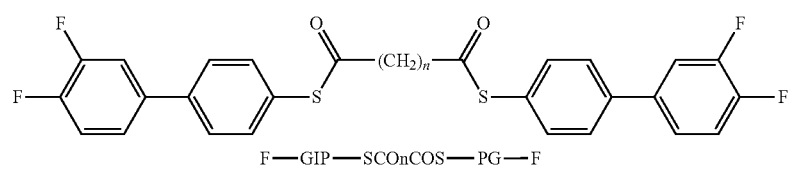
F—GIP—SCOnCOS—PG—F
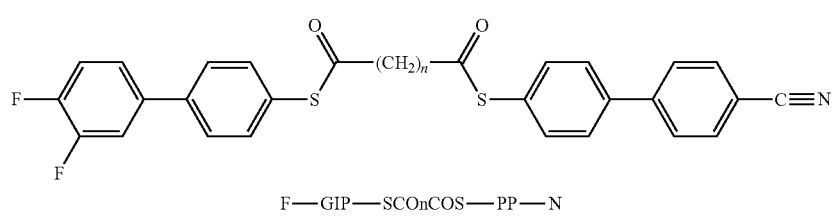
F—GIP—SCOnCOS—PP—N TABLE D-continued
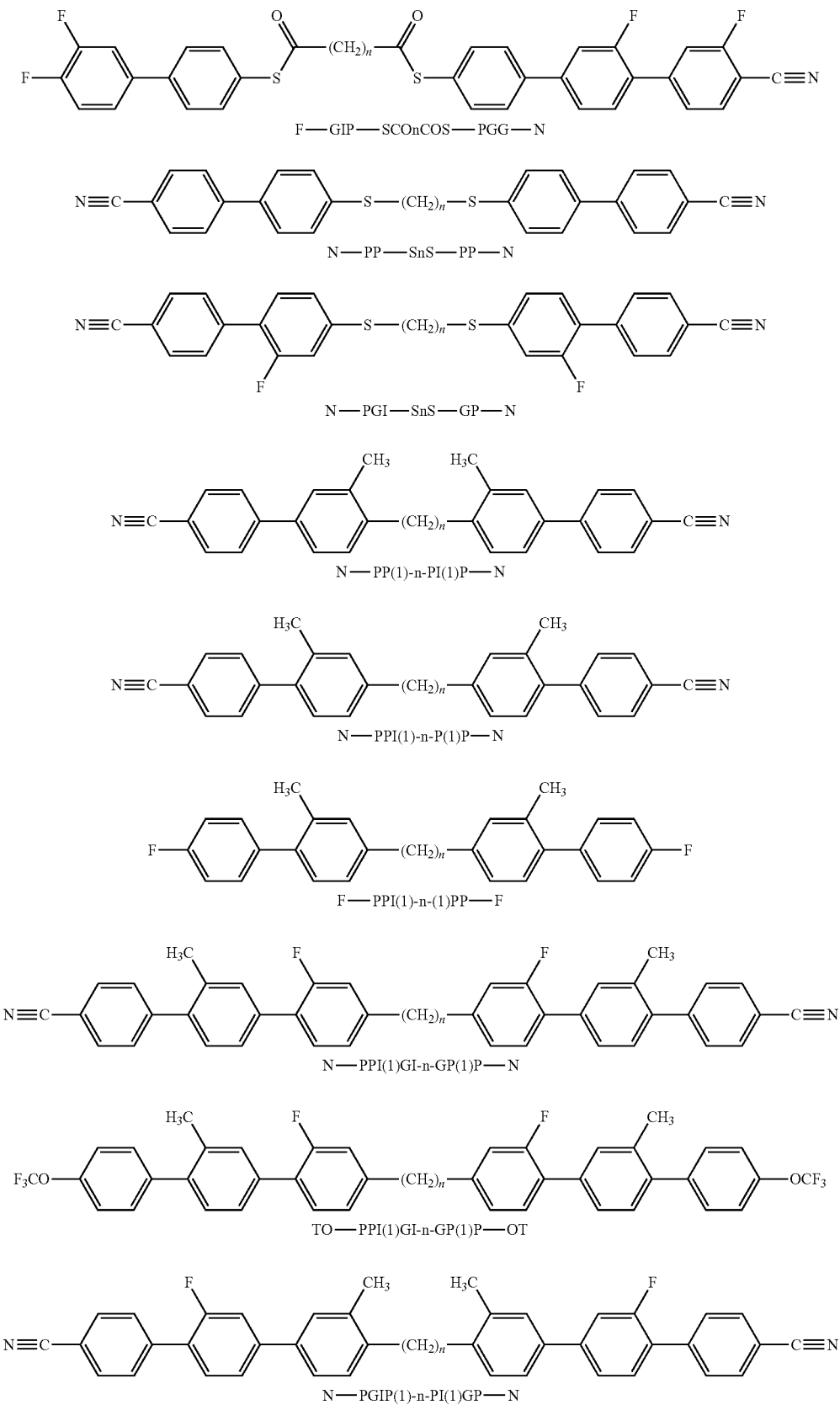

TABLE D-continued
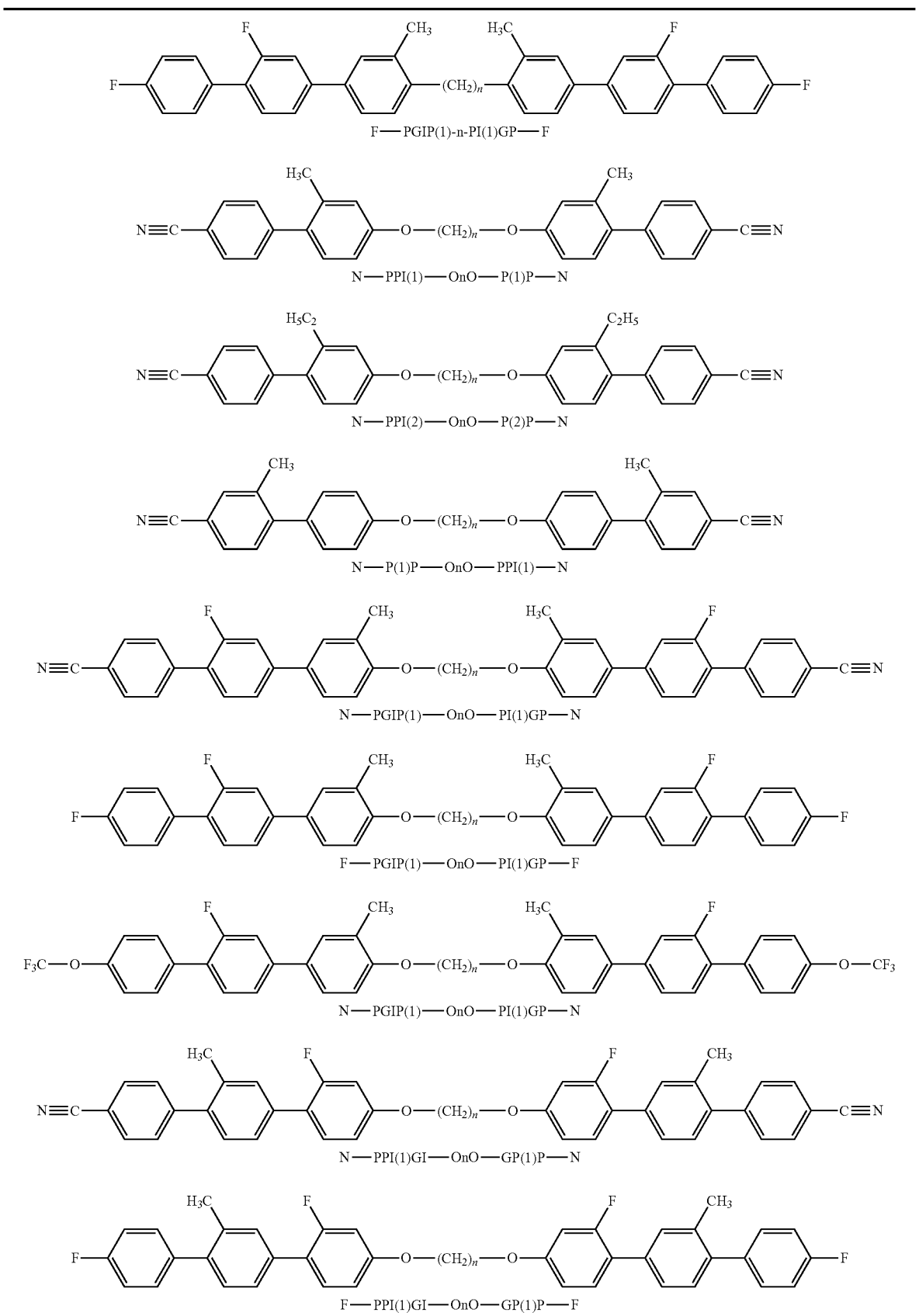

TABLE D-continued
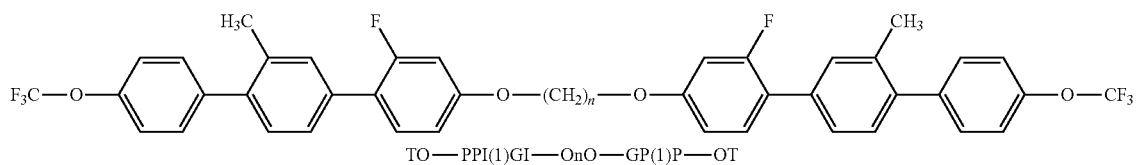
TO—PPI(1)GI—OnO—GP(1)P—OT
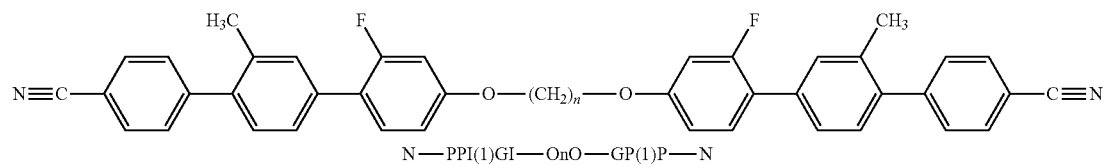
N—PPI(1)GI—OnO—GP(1)P—N
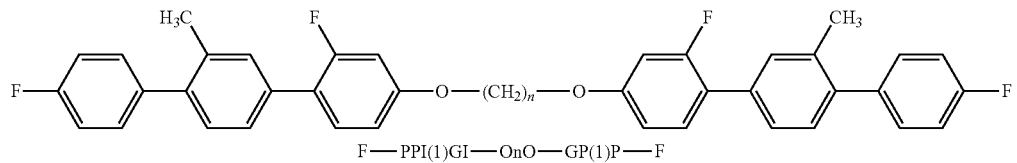
F—PPI(1)GI—OnO—GP(1)P—F
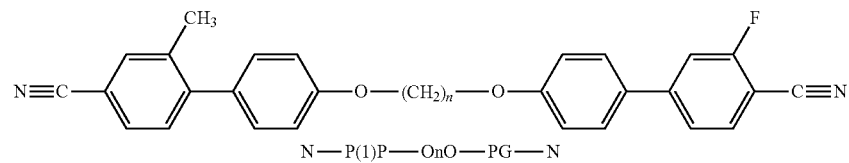
N—P(1)P—OnO—PG—N
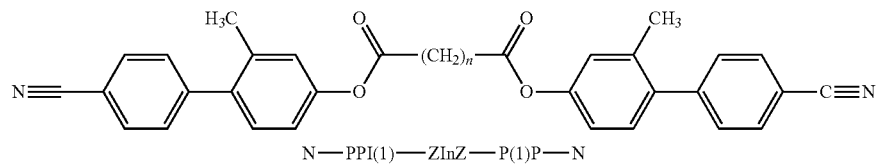
N—PPI(1)—ZInZ—P(1)P—N
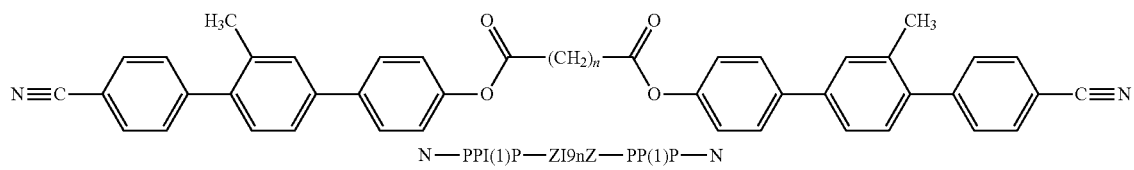
N—PPI(1)P—ZI9nZ—PP(1)P—N
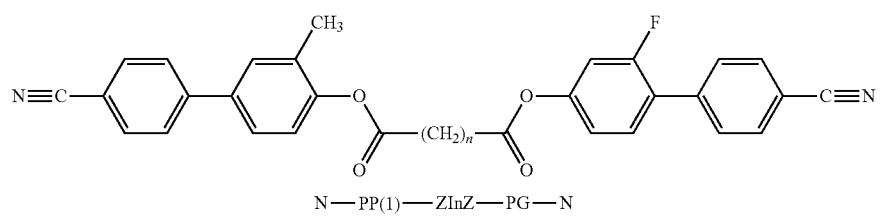
N—PP(1)—ZInZ—PG—N

COMPOUND AND SYNTHESIS EXAMPLES

SYNTHESIS EXAMPLE 1

Preparation of Nonyl-1-[4'-cyano-biphenyl-3-yl]-9-[4'-cyano-biphenyl-4-yl]:

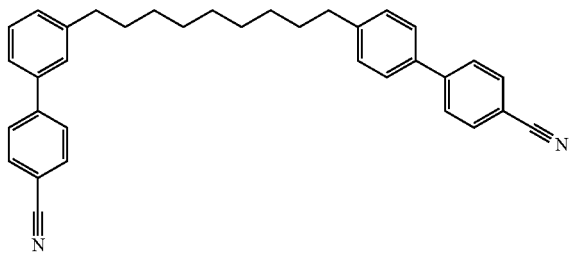 [SMILES: N#Cc1ccc(-c2ccc(CCCCCCCCCc3cccc(-c4ccc(C#N)cc4)c3)cc2)cc1]

Step 1.1

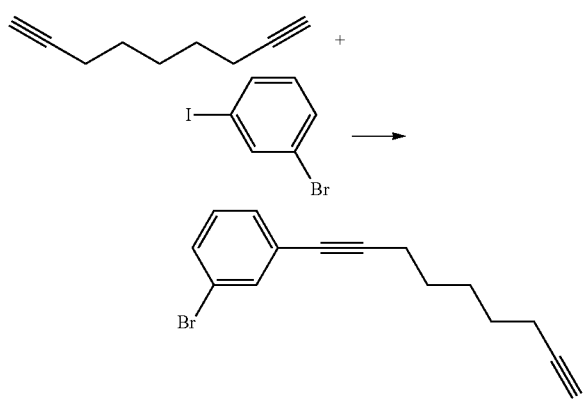

Conditions for the reaction: Pd(PPh$_3$)$_2$Cl$_2$, CuI, (C$_2$H$_5$)$_3$N, THF.

1,8-Nonadiyene (50.0 g, 416.0 mmol) is dissolved in THF (150 mL) and added into a 500 mL round bottom flask. The flask is evacuated and refilled with nitrogen 3 times. Bis(triphenylphosphine)palladium(II)dichloride (1.1 g, 1.581 mmol), copper iodide (0.23 g, 1.25 mmol) and diisopropylamine (30 mL) are added into the flask. The flask is evacuated and refilled with nitrogen gas. Then it is treated in an ultrasonic bath to degas the reaction mixture, a procedure shortly referred to as "ultasonication" or or shortly "sonication" in this application, for 30 minutes. 1,3-Bromoiodobenzene (29.4 g, 104.0 mmol) is dissolved in THF (50 mL) and added slowly over a time span of 15 minutes. A precipitate forms and the reaction mixture is stirred for 1.5 hours at room temperature, which means a temperature of approximately 20° C. throughout this application, unless explicitly stated otherwise, before it is filtered in vacuo. The filtrate is washed with water and concentrated to give the crude product as an oil. This oil is distilled to remove non reacted nonadiyene and then purified by flash chromatography using silica gel, eluting with 9:1 petrol/diethyl ether.

Step 1.2

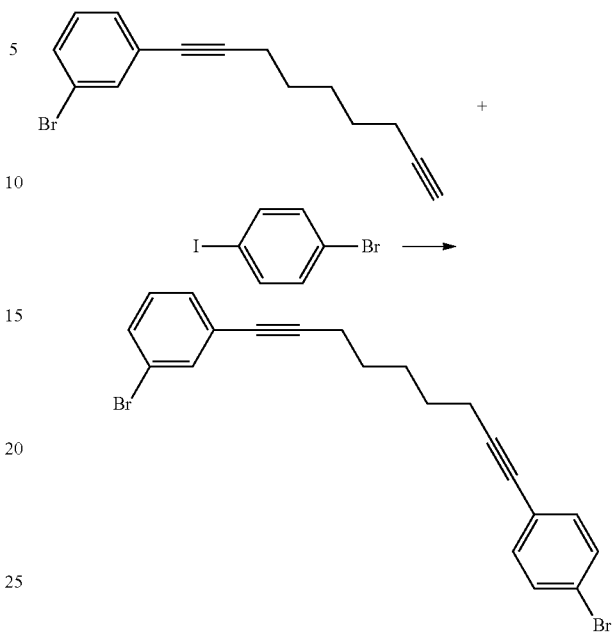

Conditions for the reaction: Pd(PPh$_3$)$_2$Cl$_2$, CuI, (C$_2$H$_5$)$_3$N, THF.

The product from the previous step, step 1.1, (6.7 g, 24.4 mmol) is solved in THF (50 mL) and added into a 250 mL round bottom flask. The flask is evacuated 3 times and refilled with nitrogen. Bis(triphenylphosphine)-palladium (II)dichloride (0.065 g, 0.09 mmol), copper iodide (0.014 g, 0.07 mmol) and diisopropylamine (10 mL) are added to the flask. The flask is evacuated and refilled with nitrogen, then sonicated for 30 minutes to degas. 1,4-Bromoiodobenzene (6.8 g, 24.3 mmol) dissolved in THF (50 mL) is added slowly over a time span of 15 minutes. A precipitate is formed and the reaction mixture is stirred for 1.5 hours at ambient temperature. On completion of the reaction the reaction mixture is filtered and the filtrate is washed with deionised water, dried over magnesium sulphate and concentrated. The crude product is purified by flash chromatography through silica gel, eluting with petrol, yielding a pure white solid product.

Step 1.3

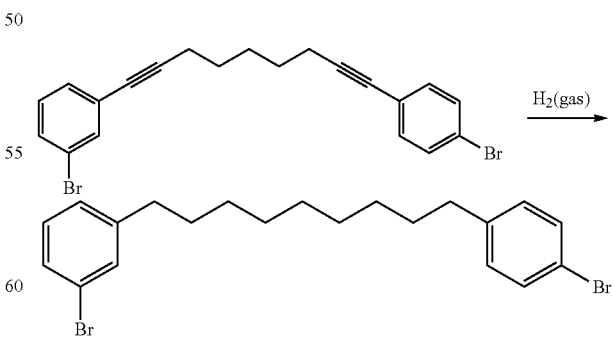

Conditions for the reaction: Pd(C), H$_2$, THF.

The hydrohenation apparatus "H-Cube" from ThalesNano Inc., Budapest, Hungary is equipped with a new Platinum/Carbon catalyst and set to a flow rate 10 mL/min at 20 bar and 40° C. 6.50 g of the product from the previous step, step 1.2, is mixed with THF (200 mL) and fed through the H-cube. Analysis shows the reaction is incomplete. The H-cube is reset to 30 bar and 50° C., the flow rate is kept the same and the solution passed through again, yielding the product. This is carried onto the next step without purification.

Step 1.4

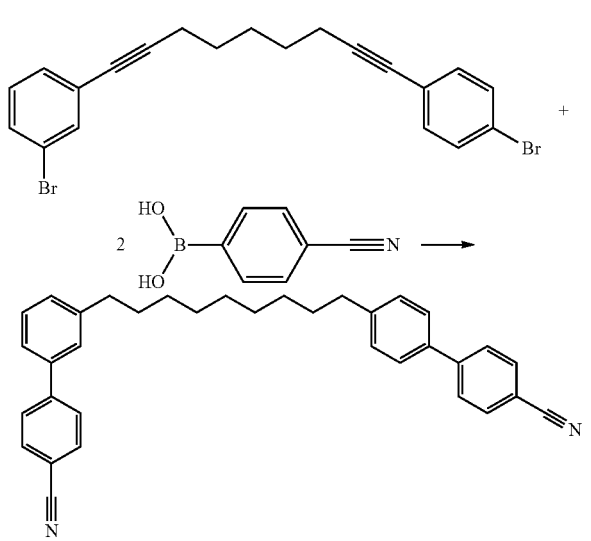

Conditions for the reaction: Pd(PPh$_3$)$_2$Cl$_2$, Na$_2$CO$_3$, H$_2$O, THF.

The product from the previous step, step, 1.3, (4.50 g, 10.27 mmol) and 4-Cyanophenylboronic acid (4.70 g, 20.5 mmol) are dissolved in 1,4-dioxane (40 mL) in a 250 mL 3-neck round bottom flask. Sodium carbonate (2.08 g, 19.61 mmol) and water (10 mL) are added to the reaction mixture and then (1,1'-bis(diphenylphosphino)ferrocene)palladium (II)dichloride (0.45 g, 0.61 mmol) is added. This reaction mixture is heated to a temperature of at 80.0° C. and stirred for 16 h. Once the reaction is complete, it the reaction mixture is filtered, the filtrate is neutralised with dilute Hydrochloric acid and then washed with water. The aqueous solutions are combined and extracted three times with diethyl ether. The combined extracts are dried over magnesium sulphate and concentrated in vacuo to give a brown oil. This is purified by column chromatography through silica gel eluting with ethyl acetate/petroleum ether (1:20) followed by two subsequent recrystallisations from acetonitrile and Isopropyl alcohol to yield the pure product.

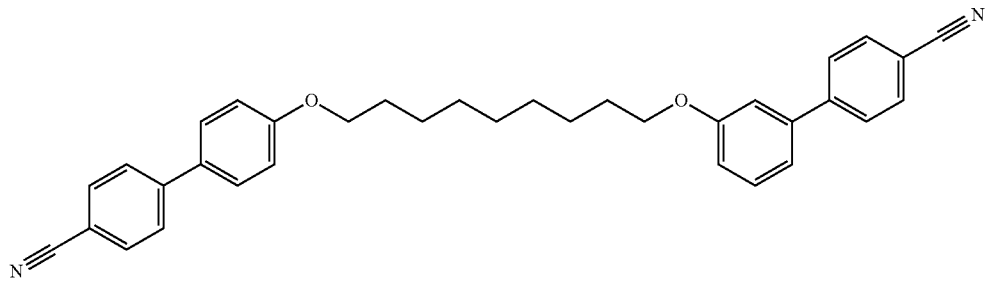 [SMILES: N#Cc1ccc(-c2ccc(OCCCCCCCCCOc3cccc(-c4ccc(C#N)cc4)c3)cc2)cc1]

Phase sequence: K 88.3 I; T*(N,I)=71.5° C.; e/K=1.85 V$^{-1}$.

(Remark: T*(N,I) and e/K extrapolated from 10% in host mixture H-0 with 2% of R-5011.)

SYNTHESIS EXAMPLE 2

Preparation of Nonyl-1-[4'-cyano-biphenyl-3-oxy]-9-[4'-cyano-biphenyl-4-oxy]

Step 2.1

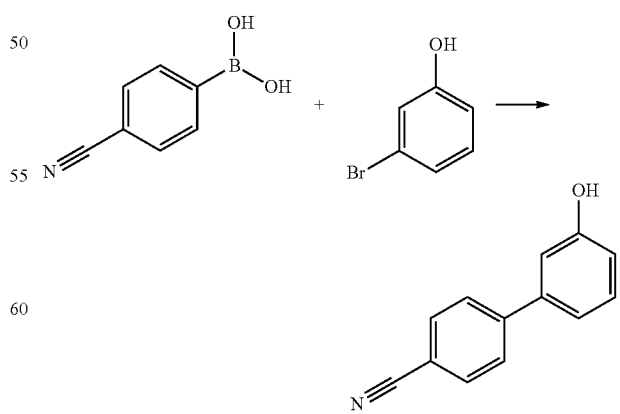

4-Cyanoboronic acid (9.936 g, 67.917 mmol) and 3-bromophenol (10.635 g, 61.470 mmol) are dissolved in 1,4- dioxane (70 mL) in a 250 mL 3-neck round bottom flask. Sodium carbonate (12.433 g, 117.408 mmol) is dissolved in water (21 mL) and (1,1'-bis(diphenylphosphino)ferrocene) palladium(II)dichloride (0.451 g, 0.610 mmol) is added to the reaction mixture. The reaction mixture is heated to a temperature of and stirred for 16 h. A GCMS sample is taken to monitor the degree of completion of the reaction. Once the reaction is complete, the reaction is filtered and the filtrate is separate to isolate the organic phase. This is washed, dried and concentrated. The crude product is dry loaded onto a silica column and the product eluted with 5% ethyl acetate in DCM and the product is obtained in good purity.

Step 2.2

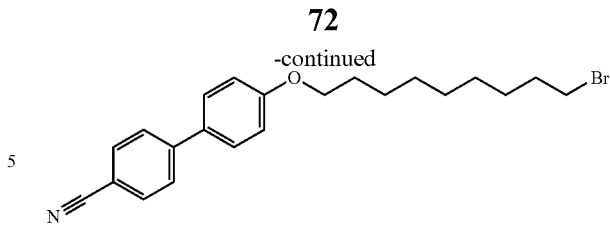

4'-Cyanobiphenol (12.5 g, 64.0 mmol) is dissolved in a minimum amount of acetone in a 500 mL round bottom flask. Potassium carbonate (19.0 g, 137 mmol) and 1,9-dibromononane (133.7 g, 467.3 mmol) are added. The reaction mixture is stirred and heated under reflux for 16 h. Upon completion of the reaction, the reaction mixture is cooled and filtered. The filtrate is separated and the organic phase is washed, dried and concentrated. The crude product is purified by recrystallisation from petrol to yield the product in good purity.

Step 2.3

The product from the previous step, step 2.2, (15.000 g, 37.467 mmol) and 3-cyanobiphenol, the product from step 2.1, (7.314 g, 37.467 mmol) are dissolved in minimum amount of acetone in a 500 mL round bottom flask. Potassium carbonate (10.874 g, 138.210 mmol) is added with stirring and the reaction is heated to gentle reflux for 24 hours. Once the reaction is complete, the reaction mixture is cooled and the precipitates removed by filtration in vacuo. The filter pad is washed well with acetone and the filtrate is washed with dilute Hydrochloric acid. The organic phase is separated, washed with deionised water and concentrated. The product is (purified by column chromatography through silica gel?) it is eluted using 100% DCM and then purified by recrystallisation from acetonitrile to yield the pure product.

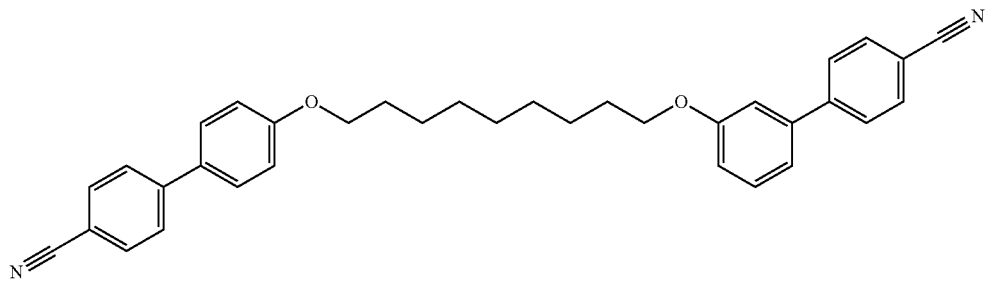 [SMILES: N#Cc1ccc(-c2ccc(OCCCCCCCCCOc3cccc(-c4ccc(C#N)cc4)c3)cc2)cc1]

Phase sequence: K 105.6 (N 75.0) I; T*(N,I)=81.0° C.; e/K=1.63 V$^{-1}$.
(Remark: T*(N,I) and e/K extrapolated from 10% in host mixture H-0 with 2% of R-5011.)

SYNTHESIS EXAMPLE 3

Undecanedioic acid 4'-cyano-biphenyl-3-yl ester 4'-cyano-biphenyl-4-yl)ester

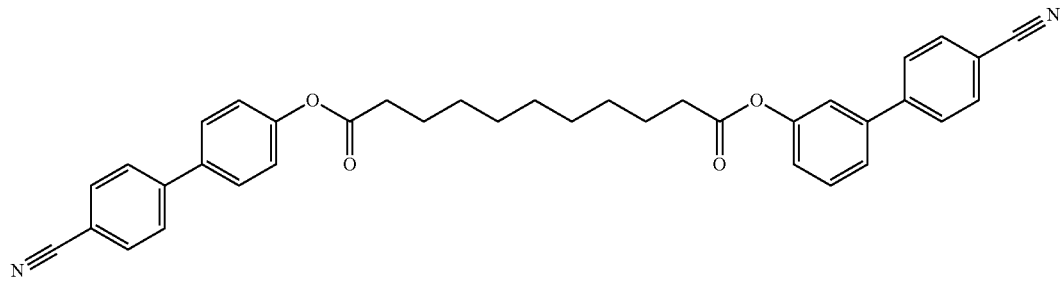 [SMILES: N#Cc1ccc(-c2ccc(OC(=O)CCCCCCCCCC(=O)Oc3cccc(-c4ccc(C#N)cc4)c3)cc2)cc1]

Step 3.1

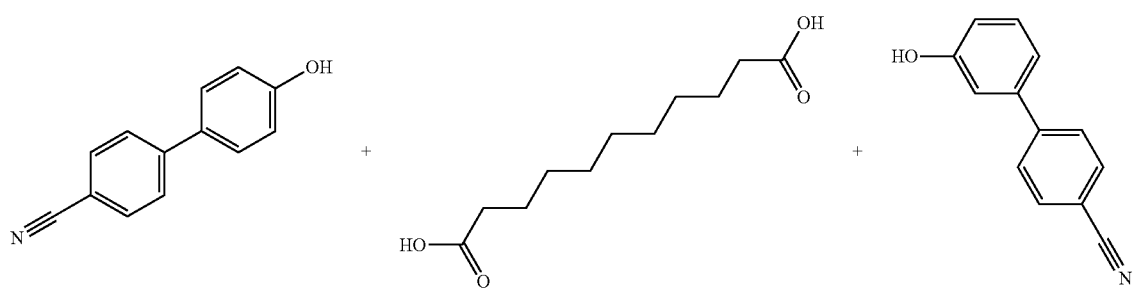

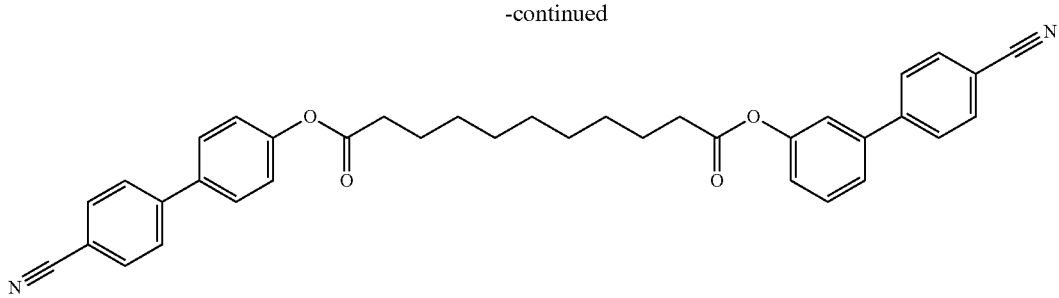

Undecanedioic acid (9.971 g, (46.103 mmol), Dicyclohexylcarbodiimide (DCC) (9.512 g, 46.103 mmol) and Dimethylaminopyridine (DMAP) (5.632 g, 46.103 mmol) are suspended in chilled DCM (140 mL) in a 250 mL round bottom flask. 4'-cyanobiphenol (9.000 g, 46.103 mmol) is added over a time span of 30 minutes and the reaction mixture is stirred at room temperature for 16 h. Once the first phenol has completely reacted the product from step 2.1 of Synthesis Example 2, 3'-cyanobiphenol (9.000 g, 46.103 mmol) and another equivalent of DCC (9.512 g, 46.103 mmol) are added to the reaction mixture. The reaction mixture is once more stirred at room temperature for 16 h. After completion of the reaction reaction mixture is filtered and the filtrate is reduced in vacuo. The crude product is purified using flash chromatography in DCM. The pure product is obtained and its structure confirmed by NMR.

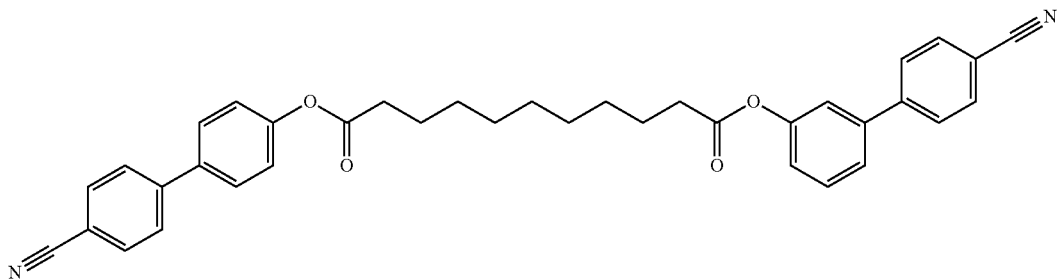 [SMILES: N#Cc1ccc(-c2ccc(OC(=O)CCCCCCCCCC(=O)Oc3cccc(-c4ccc(C#N)cc4)c3)cc2)cc1]

Phase sequence: K 73.0 X 93.0 Y 107.0 I; T*(N,I)=79.0° C.; e/K=1.81 V$^{-1}$.

(Remarks: T*(N,I) and e/K extrapolated from 10% in host mixture H-0 with 2% of R-5011, phases X and Y to be determined.)

SYNTHESIS EXAMPLE 4

Sebacic acid 4'-cyano-biphenyl-3-yl ester 4'-cyano-biphenyl-4-yl)ester

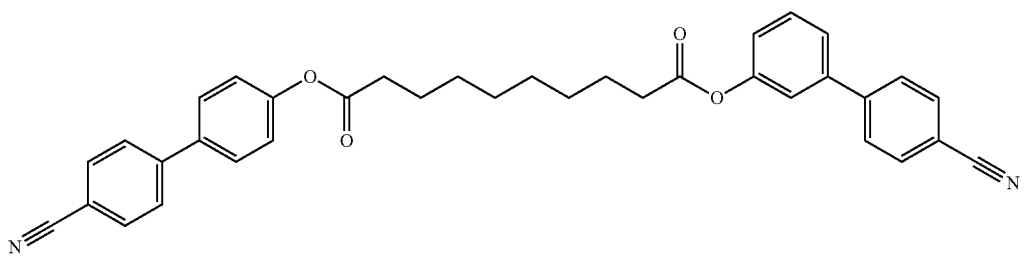 [SMILES: N#Cc1ccc(-c2ccc(OC(=O)CCCCCCCCC(=O)Oc3cccc(-c4ccc(C#N)cc4)c3)cc2)cc1]

Step 4.1

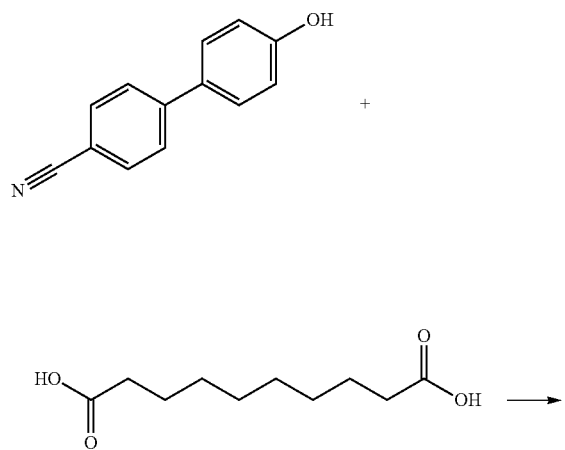

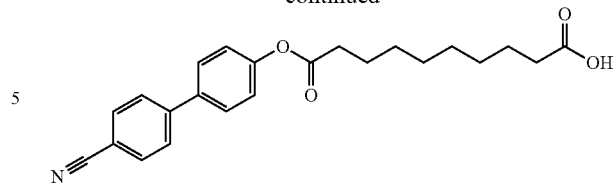

Sebacic acid (7.995 g, 39.531 mmol), DCC (8.156 g, 39.531 mmol) and DMAP (4.830 g, 39.531 mmol) are suspended in chilled DCM (120 mL) in a 250 mL round bottom flask. 4'-Cyanobiphenol (7.717 g, 39.531 mmol) is added slowly over a time span of 30 minutes and the reaction mixture is then stirred at room temperature for 16 h. On completion of the reaction the reaction mixture is filtered and the filtrate reduced in vacuo. Column chromatography is used to purify the asymmetric product but a certain amount of the symmetrical product is also isolated.

Step 4.2

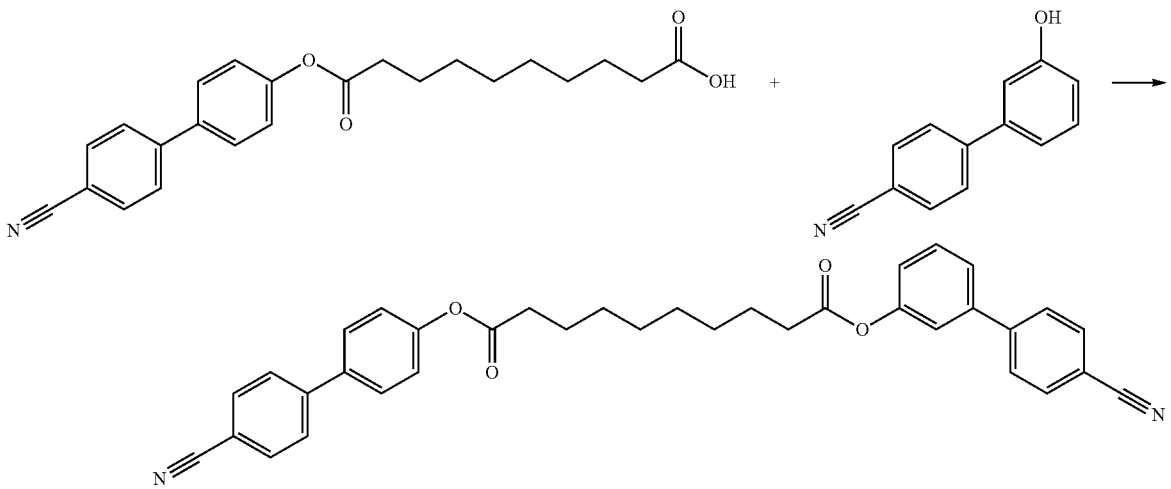

The intermediate product from the previous step, step 4.2, (4.890 g, 12.887 mmol), DCC (2.516 g, 12.887 mmol) and DMAP (1.574 g, 12.887 mmol) are suspended in chilled DCM (50 mL) in a 100 mL round bottom flask. 3'-Cyanobiphenol (2.516 g, 12.887 mmol) from step 2.1 of Synthesis Example 2, is added slowly over a time span of 30 minutes and the reaction mixture is stirred at room temperature for 16 h. After completion of the reaction the reaction mixture is filtered and the filtrate reduced in vacuo. The crude product is purified by column chromatography with 2% ethyl acetate in petrol yielding the pure product.

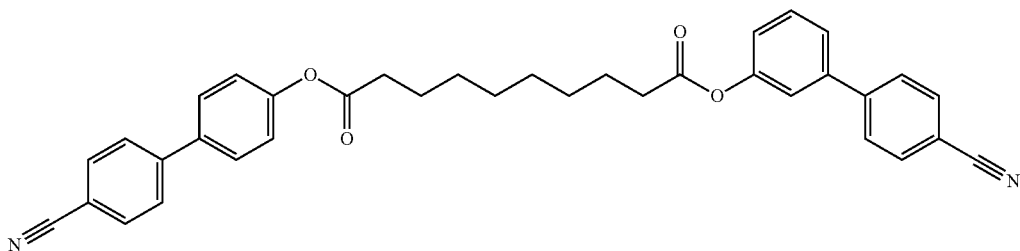 [SMILES: N#Cc1ccc(-c2ccc(OC(=O)CCCCCCCCC(=O)Oc3cccc(-c4ccc(C#N)cc4)c3)cc2)cc1]

Phase sequence: K 74 X 85 SmA 109 I; T*(N,I)=74.0° C.; e/K=1.75 V⁻¹.

(Remarks: T*(N,I) and e/K extrapolated from 10% in host mixture H-0 with 2% of R-5011, phase X to be determined.)

SYNTHESIS EXAMPLE 5

Nonyl-1-[(4'-difluoro-terphenyl-3-yl]-9-[4'-difluoro-biphenyl-4-yl]

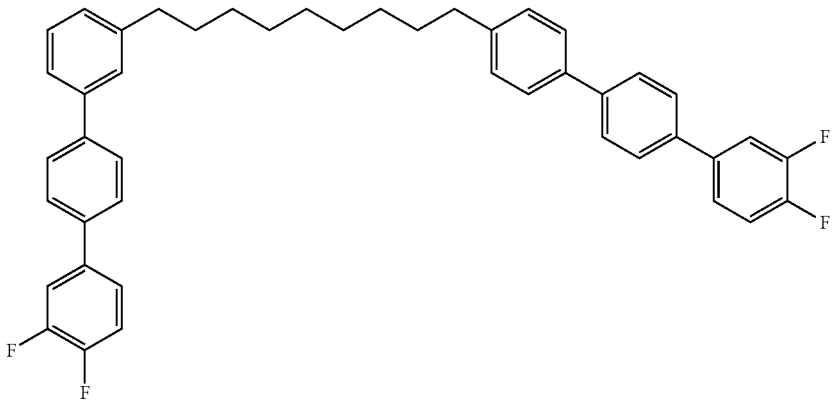 [SMILES: Fc1ccc(-c2ccc(-c3ccc(CCCCCCCCCc4cccc(-c5ccc(-c6ccc(F)c(F)c6)cc5)c4)cc3)cc2)cc1F]

Step 5.1

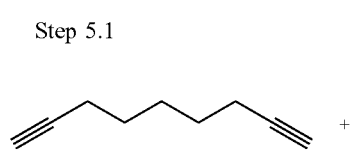

This reaction proceeds analogously to that of step 1.1. of Synthesis Example 1.

Step 5.2

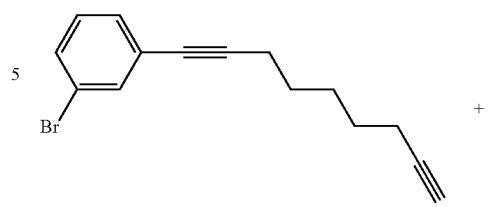

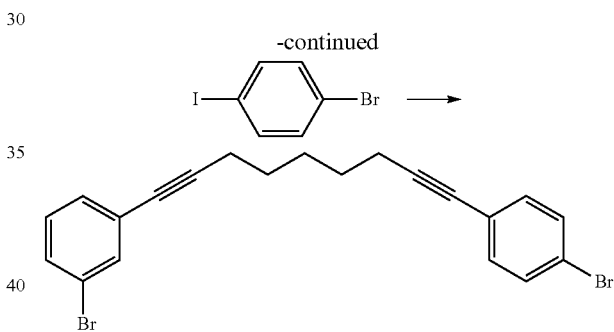

This reaction proceeds analogously to that of step 1.2 of Synthesis Example 1.

Step 5.3

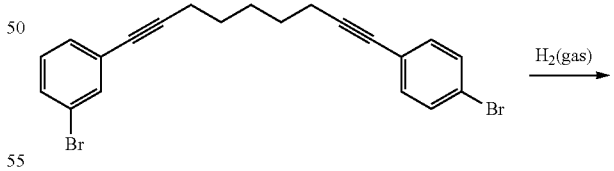

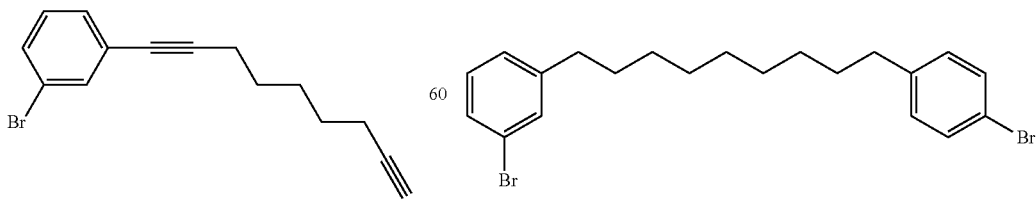

This reaction proceeds analogously to that of step 1.3 of Synthesis Example 1.

Step 5.4

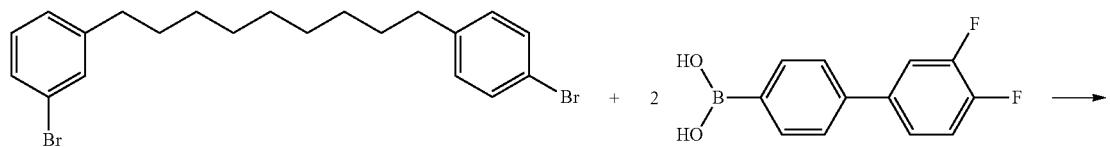

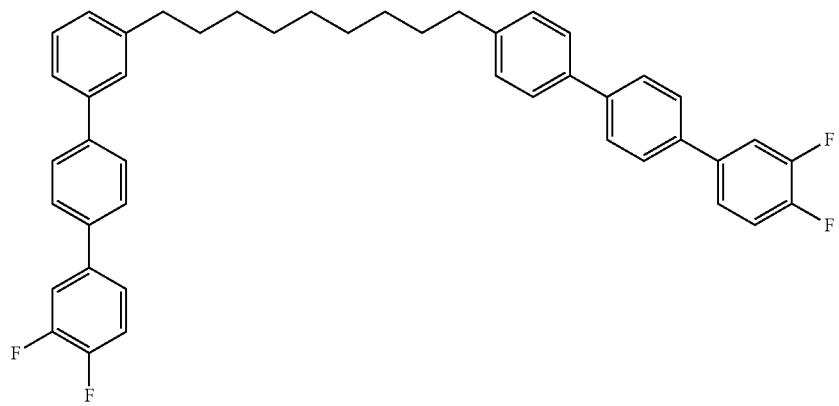

This reaction proceeds analogously to that of step 1.4 of Synthesis Example 1. 3,4-Difluorobiphenyl boronic acid (3.00 g, 12.819 mmol) and the product from step 5.1, (2.809 g, 6.410 mmol) are dissolved in 1,4-dioxane (20 mL) in a 100 mL 3-neck round bottom flask. Sodium carbonate (1.15 g, 10.897 mmol) is dissolved in water (5 mL) and bis(triphenylphosphine)palladium(II)dichloride (0.045 g, 0.064 mmol) is added. The reaction mixture is stirred and heated under reflux at 80.0° C. for 40 h. The reaction mixture is the filtered and the filtrate is separated. The organic phase is washed, dried and concentrated leading to the crude product. This is purified by column chromatography, eluting with dichloromethane/petrol mixture (3:1 ratio) to yield the pure product is.

Phase sequence: K 115 N 120 I; T*(N,I)=78.0° C.; e/K=1.71 V$^{-1}$.

(Remark: T*(N,I) and e/K extrapolated from 10% in host mixture H-0 with 2% of R-5011.)

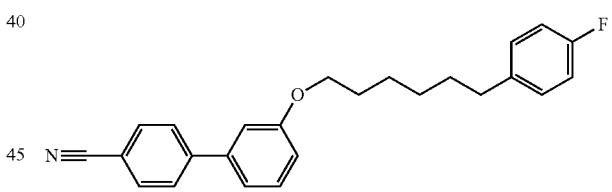

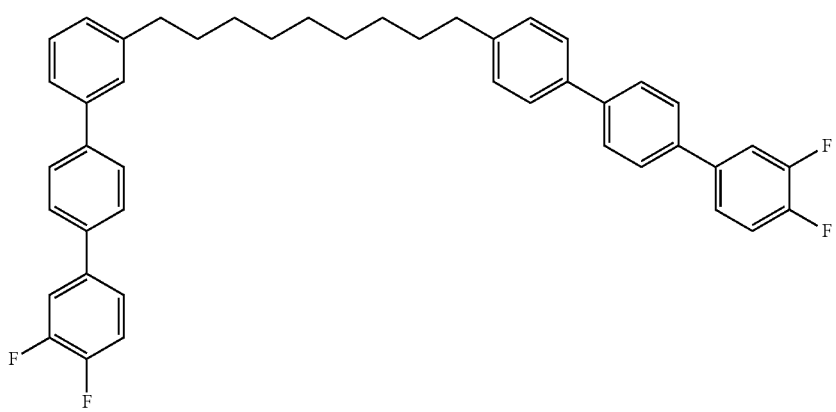 [SMILES: Fc1ccc(-c2ccc(-c3ccc(CCCCCCCCCc4cccc(-c5ccc(-c6ccc(F)c(F)c6)cc5)c4)cc3)cc2)cc1F]

SYNTHESIS EXAMPLE 6

Hexyl-1-[(4-fluorophenyl-4-yl]-6-[4'-cyano-biphenyl-4-yl]

Step 6.1

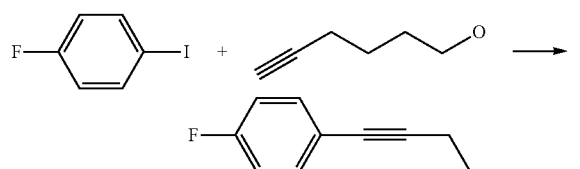

4-fluoro-iodobenzene (50.0 g, 225 mmol) is dissolved in tetrahydrofuran (280 ml) under stirring. Triethylamine (28 ml, 200 mmol) is added before the reaction mixture is evacuated and refilled with nitrogen, then sonicated for 10 minutes to degas the solvents. Copper(I)iodide (0.56 g, 2.9 mmol) and bis-(triphenylphosphine)palladium dichloride (5.6 g, 8 mmol) are added as catalysts, and the mixture is sonicated for a further 1 hour. Hex-5-yn-1-ol (25.1 ml, 227 mmol) is added slowly, keeping the temperature of the reaction mixture below 40° C. After stirring the reaction mixture for 1 additional hour at a temperature of 30° C. the reaction mixture is filtered in vacuo, the filter pad washed with Dichloromethane and the filtrate concentrated to dryness. The raw material is purified by column chromatography on silica gel, eluting with petroleum ether 40-60° to afford a coloured liquid.

Step 6.2

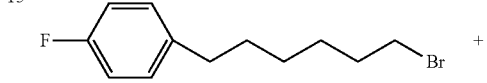

This reaction proceeds analogously to that of step 1.3 of Synthesis Example 1.

Step 6.3

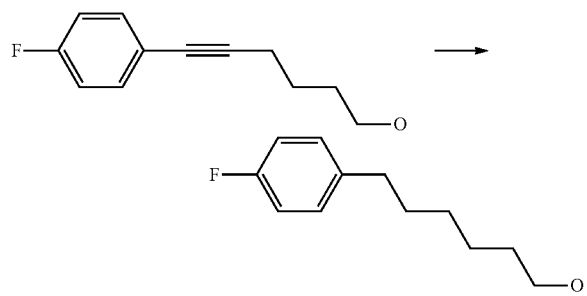

The intermediate alcohol from the previous step, Step 6.2, (30.0 g, 153 mmol) is dissolved in anhydrous dichloromethane together with triphenylphosphine (60.5 g, 230 mmol) and then the solution is cooled to a temperature in the range from 0 to −5° C. N-Bromosuccinimide (40.8 g, 229 mmol) is added in small portions before the mixture is stirred at a temperature of 25° C. for 16 hours. The solvent is removed in vacuo resulting in a black solid, which is purified by column chromatography on silica gel, eluting with petroleum ether 40-60° to afford a the product as a coloured liquid.

Step 6.4

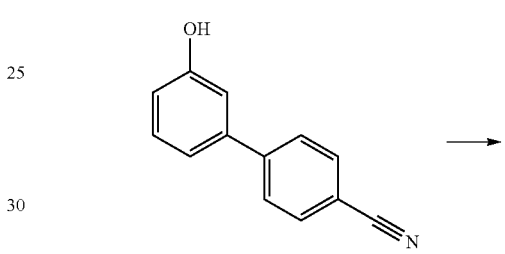

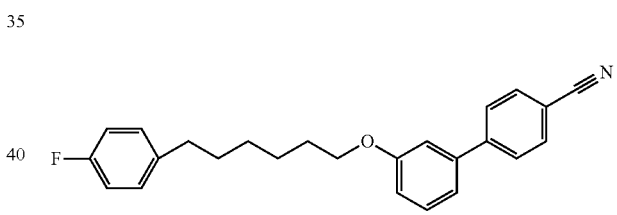

The intermediate bromide from the previous step, Step 6.3, (4.0 g, 15.4 mmol) and 4'-cyanobiphen-3"-ol (3.0 g, 15.4 mmol) are charged into a 250 ml round-bottom flask and dissolved in butanone (200 ml). Potassium carbonate (23.9 g, 173 mmol) is added and the resulting suspension is stirred for 16 hours under gentle reflux. The reaction mixture is cooled before the solids are removed in vacuo, the filter pad washed well with butanone. The filtrate is concentrated to dryness and purification is carried out by column chromatography through a short silica column, eluting with petroleum ether 40-60°/diethyl ether mixture (up to 2% diethyl ether concentration is used). The product is obtained as a white solid.

Phase sequence: K 45.2 I; T*(N,I)=67.0° C.; e/K=2.10 $V^{-1}$.

(Remark: T*(N,I) and e/K extrapolated from 10% in host mixture H-0 with 2% of R-5011.)

COMPOUND EXAMPLES 7 and Following

The following compounds of formula I are prepared analogously.

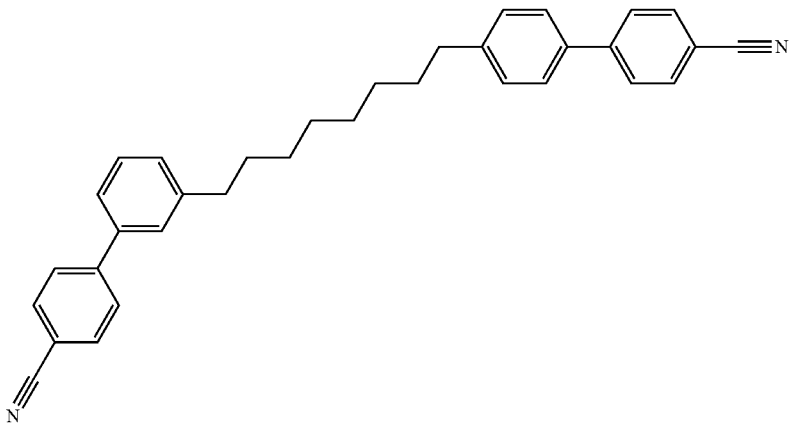 [SMILES: N#Cc1ccc(-c2ccc(CCCCCCCCc3cccc(-c4ccc(C#N)cc4)c3)cc2)cc1]

Phase sequence: K 92 (N 37) I; T*(N,I)=74.0° C.; e/K=1.96 V$^{-1}$.

(Remark: T*(N,I) and e/K extrapolated from 10% in host mixture H-0 with 2% of R-5011.)

The materials in the above table generally showed increased performance in the screening mixtures, as compared to known, more conventional bimesogenic compounds as e.g. those shown in the table below.

USE EXAMPLES, MIXTURE EXAMPLES

Typically a 5.6 μm thick cell, having an anti-parallel rubbed PI alignment layer, is filled on a hotplate at a temperature at which the flexoelectric mixture in the isotropic phase.

After the cell has been filled phase transitions, including clearing point, are measured using Differential Scanning Calorimetry (DSC) and verified by optical inspection. For optical phase transition measurements, a Mettler FP90 hot-stage controller connected to a FP82 hot-stage is used to control the temperature of the cell. The temperature is increased from ambient temperature at a rate of 5 degrees C. per minute, until the onset of the isotropic phase is observed. The texture change is observed through crossed polarizers using an Olympus BX51 microscope and the respective temperature noted.

Wires are then attached to the ITO electrodes of the cell using indium metal. The cell is secured in a Linkam THMS600 hot-stage connected to a Linkam TMS93 hot-stage controller. The hot-stage is secured to a rotation stage in an Olympus BX51 microscope.

The cell is heated until the liquid crystal is completely isotropic. The cell is then cooled under an applied electric field until the sample is completely nematic. The driving waveform is supplied by a Tektronix AFG3021 B arbitrary function generator, which is sent through a Newtons4th LPA400 power amplifier before being applied to the cell. The cell response is monitored with a Thorlabs PDA55 photodiode. Both input waveforms and optical response are measured using a Tektronix TDS 2024B digital oscilloscope.

In order to measure the flexoelastic response of the material, the change in the size of the tilt of the optic axis is measured as a function of increasing voltage. This is achieved by using the equation:

$$\tan\varphi = \frac{P_0}{2\pi}\frac{e}{K}E$$

wherein φ is the tilt in the optic axis from the original position (i.e. when E=0), E is the applied field, K is the elastic constant (average of $K_1$ and $K_3$) and e is the flexoelectric coefficient (where $e=e_1+e_3$). The applied field is monitored using a HP 34401A multimeter. The tilt angle is measured using the aforementioned microscope and oscilloscope. The undisturbed cholesteric pitch, $P_0$, is measured using an Ocean Optics USB4000 spectrometer attached to a computer. The selective reflection band is obtained and the pitch determined from the spectral data.

The mixtures shown in the following examples are well suitable for use in USH-displays. To that end an appropriate concentration of the chiral dopant or dopants used has to be applied in order to achieve a cholesteric pitch of 200 nm or less.

COMPARATIVE MIXTURE EXAMPLE 1.1

Host Mixture H-0

The host mixture H-0 is prepared and investigated.

| No. | Composition Compound Abbreviation | Conc./% |
|---|---|---|
| 1 | F-PGI-O9O-GP-F | 25.0 |
| 2 | F-PGI-O9O-PP-N | 25.0 |
| 3 | F-PGI-ZI9Z-GP-F | 25.0 |
| 4 | F-PGI-ZI9Z-PP-N | 25.0 |
| Σ | | 100.0 |

2% of the chiral dopant R-5011 are added to the mixture H-0 leading to the mixture H-1, which is investigated for its properties.

| No. | Composition Compound Abbreviation | Conc./% |
|---|---|---|
| 1 | R-5011 | 2.0 |
| 2 | F-PGI-O9O-GP-F | 24.5 |
| 3 | F-PGI-O9O-PP-N | 24.5 |
| 4 | F-PGI-ZI9Z-GP-F | 24.5 |
| 5 | F-PGI-ZI9Z-PP-N | 24.5 |
| Σ | | 100.0 |

The mixture H-1 may be used for the USH-mode. It has a clearing point of 82° C. and a lower transition temperature [T(N2,N)] of 33° C. It has a cholesteric pitch of 291 nm at 0.9T(N,I). The e/K of this mixture is 1.80 $Cm^{-1}N^{-1}$ at 0.9T(N,I).

MIXTURE EXAMPLES 1.1 to 1.14

2% of the chiral dopant R-5011 and 10% of the compound of synthesis example 1 are added to the mixture H-0 leading to the mixture M-1.1, which is investigated for its properties.

MIXTURE EXAMPLE 1

Mixture M-1

| No. | Composition Compound Abbreviation | Conc./% |
|---|---|---|
| 1 | R-5011 | 2.0 |
| 2 | F-PGI-O9O-GP-F | 22.0 |
| 3 | F-PGI-O9O-PP-N | 22.0 |
| 4 | F-PGI-ZI9Z-GP-F | 22.0 |
| 5 | F-PGI-ZI9Z-PP-N | 22.0 |
| 6 | Compound 1 | 10.0 |
| Σ | | 100.0 |

Remark: *) Compound of Synthesis Example 1.

This mixture (M-1) is prepared and investigated. It is well suitable for the ULH-mode. It has a cholesteric pitch of 294.4 nm at 35° C. The e/K of this mixture is 1.85 $Cm^{-1}N^{-1}$ at a temperature of 37° C.

MIXTURE EXAMPLE 2

Mixture M-2

| No. | Composition Compound Abbreviation | Conc./% |
|---|---|---|
| 1 | R-5011 | 2.0 |
| 2 | F-PGI-O9O-GP-F | 22.0 |
| 3 | F-PGI-O9O-PP-N | 22.0 |
| 4 | F-PGI-ZI9Z-GP-F | 22.0 |
| 5 | F-PGI-ZI9Z-PP-N | 22.0 |
| 6 | Compound 2 | 10.0 |
| Σ | | 100.0 |

Remark:
*) Compound of Synthesis Example 2.

This mixture (M-2) is prepared and investigated. It is well suitable for the ULH-mode. It has a cholesteric pitch of 331.4 nm at 35° C. The e/K of this mixture is 1.63 $Cm^{-1}N^{-1}$ at a temperature of 45.6° C.

MIXTURE EXAMPLE 3

Mixture M-3

| No. | Composition Compound Abbreviation | Conc./% |
|---|---|---|
| 1 | R-5011 | 2.0 |
| 2 | F-PGI-O9O-GP-F | 22.0 |
| 3 | F-PGI-O9O-PP-N | 22.0 |
| 4 | F-PGI-ZI9Z-GP-F | 22.0 |
| 5 | F-PGI-ZI9Z-PP-N | 22.0 |
| 6 | Compound 3 | 10.0 |
| Σ | | 100.0 |

Remark:
*) Compound of Synthesis Example 3.

This mixture (M-3) is prepared and investigated. It is well suitable for the ULH-mode. It has a cholesteric pitch of 309.6 nm at 35° C. The e/K of this mixture is 1.81 $Cm^{-1}N^{-1}$ at a temperature of 43.8° C.

The invention claimed is:
1. A compound of formula I

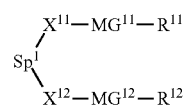

I wherein
$R^{11}$ is F, Cl, CN, NCS or a straight-chain or branched alkyl group with 1 to 25 C atoms which is unsubstituted, mono- or polysubstituted by halogen or CN, in which optionally one or more non-adjacent $CH_2$ groups are replaced, in each occurrence independently from one another, by —O—, —S—, —NH—, —N($CH_3$)—, —CO—, —COO—, —OCO—, —O—CO—O—, —S—CO—, —CO—S—, —CH=CH—, —CH=CF—, —CF=CF— or —C≡C—,
$R^{12}$ is H, F, Cl, CN, NCS or a straight-chain or branched alkyl group with 1 to 25 C atoms which is unsubstituted, mono- or polysubstituted by halogen or CN, in which optionally one or more non-adjacent $CH_2$ groups are replaced, in each occurrence independently from one another, by —O—, —S—, —NH—, —N($CH_3$)—, —CO—, —COO—, —OCO—, —O—CO—O—, —S—CO—, —CO—S, —CH=CH—, —CH=CF—, —CF=CF— or —C≡C—,
$MG^{11}$ is of formula II*,

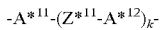

II*

$Z^{*11}$ is a single bond, —COO—, —OCO—, —O—CO—O—, —OCH_2—, —CH_2O—, —OCF_2—, —CF_2O—, —CH_2CH_2—, —(CH_2)_4—, —CF_2CF_2—, —CH=CH—, —CF=CF—, —CH=CH—COO—, —OCO—CH=CH— or —C≡C—, optionally substituted with one or more of F, S and/or Si,
one of $A^{*11}$ and $A^{*12}$ present in $MG^{11}$ is 1,3-phenylene, wherein optionally one or two non-adjacent CH groups each are optionally replaced by an N-atom, and which optionally is substituted by one or more halogen atoms and/or by one or more alkyl group(s) each independently having 1 to 9 C atoms, and/or by one more alkoxy group(s) each independently having 1 to 9 C atoms, the other of A*$^{11}$ and A*$^{12}$ present in MG$^{11}$ is 1,4-phenylene, wherein one or more CH groups are optionally replaced by N, trans-1,4-cyclo-hexylene in which, one or two non-adjacent CH$_2$ groups are optionally replaced by O and/or S, 1,4-cyclohexenylene, 1,4-bicyclo-(2,2,2)-octylene, piperidine-1,4-diyl, naphthalene-2,6-diyl, decahydro-naphthalene-2,6-diyl, 1,2,3,4-tetrahydro-naphthalene-2,6-diyl, cyclobutane-1,3-diyl, spiro[3.3]heptane-2,6-diyl or dispiro[3.1.3.1] decane-2,8-diyl, wherein all these groups are unsubstituted, mono-, di-, tri- or tetrasubstituted with F, Cl, CN or alkyl, alkoxy, alkylcarbonyl or alkoxycarbonyl groups with 1 to 7 C atoms, wherein one or more H atoms are optionally substituted by F or Cl, k is 0, 1, 2, 3 or 4, Sp$^1$ is a spacer group comprising 1, 2, 3, 4 or 5 to 40 C atoms, wherein one or more non-adjacent and non-terminal CH$_2$ groups are optionally replaced by —O—, —S—, —NH—, —N(CH$_3$)—, —CO—, —O—CO—, —S—CO—, —O —COO—, —CO—S—, —CO—O—, —CH(halogen)-, —CH(CN)—, —CH=CH— or —C≡C—, wherein one or more H atoms in —CH$_2$— groups are independently of each other optionally replaced by F or CH$_3$, and X$^{11}$ and X$^{12}$ are each independently of one another —CH=CH—, —C≡C—, —O—, —CF$_2$—O—, —O—CF$_2$—, —CO—O—, —O—CO—, —O—CO—O—, —S—, —CS—S—, —S—CS—, —CO—S—, —S—CO—, —S—CO—S—, —S—CS—S— or a single bond, MG$^{12}$ is selected from the group consisting of formulae II-0, II-0', II-1, II-2 and II-4 to II-26 and their mirror images

| | |
|---|---|
| -Phe- | II-0 |
| -PheL- | II-0' |
| -Phe-Z-Phe- | II-1 |
| -Phe-Z-Cyc- | II-2 |
| -Phe-Z-PheL- | II-4 |
| -PheL-Z-Phe- | II-5 |
| -PheL-Z-Cyc- | II-6 |
| -PheL-Z-PheL- | II-7 |
| -Phe-Z-Phe-Z-Phe- | II-8 |
| -Phe-Z-Phe-Z-Cyc- | II-9 |
| -Phe-Z-Cyc-Z-Phe- | II-10 |
| -Cyc-Z-Phe-Z-Cyc- | II-11 |
| -Phe-Z-Cyc-Z-Cyc- | II-12 |
| Cyc-Z-Cyc-Z-Cyc- | II-13 |
| -Phe-Z-Phe-Z-PheL- | II-14 |
| -Phe-Z-PheL-Z-Phe- | II-15 |
| -PheL-Z-Phe-Z-Phe- | II-16 |
| -PheL-Z-Phe-Z-PheL- | II-17 |
| -PheL-Z-PheL-Z-Phe- | II-18 |
| -PheL-Z-PheL-Z-PheL- | II-19 |
| -Phe-Z-PheL-Z-Cyc- | II-29 |
| -Phe-Z-Cyc-Z-PheL- | II-21 |
| Cyc-Z-Phe-Z-PheL- | II-22 |
| -PheL-Z-Cyc-Z-PheL- | II-23 |
| -PheL-Z-PheL-Z-Cyc- | II-24 |
| -PheL-Z-Cyc-Z-Cyc- | II-25 |
| Cyc-Z-PheL-Z-Cyc- | II-26 |

Cyc is 1,4-cyclohexylene,

Phe is 1,4-phenylene or alkyl-1,4-phenylene,

PheL is 1,4-phenylene, which is substituted by one, two or three fluorine atoms, by one or two Cl atoms, by one Cl atom and one F atom or by one alkyl or alkoxy group having 1 to 9 C—atoms, and Z is a single bond, —COO—, —OCO—, —O—CO—O—, —OCH$_2$—, —CH$_2$O—, —OCF$_2$—, —CF$_2$O—, —CH$_2$CH$_2$—, —(CH$_2$)$_4$—, —CF$_2$CF$_2$—, —CH=CH—, —CF=CF—, —CH=CH—COO—, —OCO—CH=CH— or —C≡C—, optionally substituted with one or more of F, S and/or Si, under the condition that in —X$^{11}$-Sp$^1$-X$^{12}$— no two O-atoms are adjacent to one another, no two —CH=CH—groups are adjacent to each other and no two groups selected from the group consisting of —O—CO—, —S—CO—, —O—COO—, —CO—S—, —CO—O— and —CH=CH— are adjacent to each other.

2. The compound according to claim 1, wherein Z*$^{11}$ is a single bond, —COO—, —OCO—, —O—CO—O—, —OCH$_2$—, —CH$_2$O—, —OCF$_2$—, —CF$_2$O—, —CH$_2$CH$_2$—, —(CH$_2$)$_4$—, —CF$_2$CF$_2$—, —CH=CH—, —CF=CF—, —CH=CH—COO—, —OCO—CH=CH— or —C≡C—,optionally substituted with one or more of F.

3. The compound according to claim 1, wherein MG$^{11}$ is selected from the group consisting of formulae II*-0 to II*-26 and their mirror images

| | |
|---|---|
| -Phe*- | II*-0 |
| -Phe*-Z-Phe- | II*-1 |
| -Phe*-Z-Cyc- | II*-2 |
| -Phe*-Z-PheL- | II*-4 |
| -Phe*L-Z-Phe- | II*-5 |
| -Phe*L-Z-Cyc- | II*-6 |
| -Phe*L-Z-PheL- | II*-7 |
| -Phe*-Z-Phe-Z-Phe- | II*-8 |
| -Phe*-Z-Phe-Z-Cyc- | II*-9 |
| -Phe*-Z-Cyc-Z-Phe- | II*-10 |

| | |
|---|---|
| -Cyc-Z-Phe*-Z-Cyc- | II*-11 |
| -Phe*-Z-Cyc-Z-Cyc- | II*-12 |
| -Phe*-Z-Phe-Z-PheL- | II*-13 |
| -Phe-Z-Phe*-Z-PheL- | II*-14 |
| -Phe*-Z-PheL-Z-Phe- | II*-15 |
| -Phe*L-Z-Phe-Z-Phe- | II*-16 |
| -Phe*L-Z-Phe-Z-PheL- | II*-17 |
| -Phe*L-Z-PheL-Z-Phe- | II*-18 |
| -Phe*L-Z-PheL-Z-PheL- | II*-19 |
| -Phe*-Z-PheL-Z-Cyc- | II*-20 |
| -Phe*-Z-Cyc-Z-PheL- | II*-21 |
| -Cyc-Z-Phe*-Z-PheL- | II*-22 |
| -Phe*L-Z-Cyc-Z-PheL- | II*-23 |
| -Phe*L-Z-PheL-Z-Cyc- | II*-24 |
| -Phe*L-Z-Cyc-Z-Cyc- | II*-25 |
| -Cyc-Z-Phe*L-Z-Cyc- | II*-26 | wherein
Cyc is 1,4-cyclohexylene,
Phe* is 1,3-phenylene or alkyl-1,3-phenylene,
Phe is 1,4-phenylene or alkyl-1,4-phenylene,
Phe*L is 1,3-phenylene, which is substituted by one, two or three fluorine atoms, by one or two Cl atoms or by one Cl atom and one F atom,
PheL is 1,4-phenylene, which is substituted by one, two or three fluorine atoms, by one or two Cl atoms or by one Cl atom and one F atom, and
Z is —COO—, —OCO—, —O—CO—O—, —OCH$_2$—, —CH$_2$O—, —OCF$_2$—, —CF$_2$O—, —CH$_2$CH$_2$—, —(CH$_2$)$_4$—, —CF$_2$CF$_2$—, —CH═CH—, —CF═CF—, —CH═CH—COO—, —OCO—CH═CH— or —C≡C—, optionally substituted with one or more of F.

4. The compound according to claim 1, wherein MG$^{12}$ is selected from the group consisting of formulae II-0, II-0', II-1,II-4, II-5, II-7, II-8, II-14, II-15, II-16, II-17,-II18 and II-19.

5. The compound according to claim 1, wherein R$^{11}$ and R$^{12}$ are independently of one another selected from the group consisting of OCF$_3$, CF$_3$, F, Cl and CN.

6. The compound according to claim 1, wherein Sp$^1$ is —(CH$_2$)$_o$— and o is 1, 3 or an integer from 5 to 15.

7. A liquid-crystalline medium, comprising one or more compounds according to claim 1.

8. The liquid-crystalline medium according to claim 7, which additionally comprises one or more compounds of formula III R$^{31}$-MG$^{31}$-X$^{31}$-Sp$^3$-X$^{32}$-MG$^{32}$-R$^{32}$     III wherein
R$^{31}$ and R$^{32}$ are each independently H, F, Cl, CN, NCS or a straight-chain or branched alkyl group with 1 to 25 C atoms which are unsubstituted, mono- or polysubstituted by halogen or CN, in which optionally one or more non-adjacent CH$_2$ groups are replaced, in each case independently from one another, by —O—, —S—, —NH—, —N(CH$_3$)—, —CO—, —COO—, —OCO—, —O—CO—O—, —S—CO—, —CO—S—, —CH═CH—, —CH═CF—, —CF═CF— or —C≡C—, MG$^{31}$ and MG$^{32}$ are each independently a mesogenic group, Sp$^3$ is a spacer group comprising 5 to 40 C atoms, wherein one or more non-adjacent CH$_2$ groups are optionally replaced by —O—, —S—, —NH—, —N(CH$_3$)—, —CO—, —O—CO—, —S—CO—, —O—COO—, —CO—S—, —CO—O—, —CH(halogen)-, —CH(CN)—, —CH═CH— or —C≡C—, and X$^{31}$ and X$^{32}$ are each independently —O—, —S—, —CO—, —COO—, —OCO—, —O—CO—O—, —CO—NH—, —NH—CO—, —CH$_2$CH$_2$—, —OCH$_2$—, —CH$_2$O—, —SCH$_2$—, —CH$_2$S—, —CH═CH—, —CH═CH—COO—, —OCO—CH═CH—, —C≡C— or a single bond.

9. A liquid crystal device comprising a liquid crystalline medium comprising two or more components, one or more of which is a compound of formula I according to claim 1.

10. The liquid crystal device according to claim 9, which is a flexoelectric device.

11. The compound according to claim 2, wherein Z*$^{11}$ is a single bond.

12. The compound according to claim 3, wherein Cyc is trans-1,4-cyclohexylene.

13. The compound according to claim 4, wherein Cyc is trans-1,4-cyclohexylene.

14. A compound of formula I

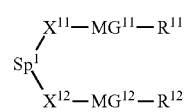

I wherein
R$^{11}$ and R$^{12}$ are each independently H, F, Cl, CN, NCS or a straight-chain or branched alkyl group with 1 to 25 C atoms which is unsubstituted, mono- or polysubstituted by halogen or CN, in which optionally one or more non-adjacent CH$_2$ groups are replaced, in each occurrence independently from one another, by —O,— S—, —NH—, —N(CH$_3$)—, —CO—, —COO—, —OCO—, —O—CO—O—, —S—CO—, —CO—S—, —CH═CH—, —CH═CF—, —CF═CF— or —C≡C—, MG$^{11}$ is selected from the group consisting of formulae II*-0, II*-0', II*-1 to II*-26 and their mirror images

| | |
|---|---|
| -Phe*- | II*-0 |
| -PheL*- | II*-0' |
| -Phe*-Z-Phe- | II*-1 |
| -Phe*-Z-Cyc- | II*-2 |
| -Phe*-Z-PheL- | II*-4 |
| -Phe*L-Z-Phe- | II*-5 |
| -Phe*L-Z-Cyc- | II*-6 |
| -Phe*L-Z-PheL- | II*-7 |

| | |
|---|---|
| -Phe*-Z-Phe-Z-Phe- | II*-8 |
| -Phe*-Z-Phe-Z-Cyc- | II*-9 |
| -Phe*-Z-Cyc-Z-Phe- | II-10 |
| -Cyc-Z-Phe*-Z-Cyc- | II*-11 |
| -Phe*-Z-Cyc-Z-Cyc- | II*-12 |
| -Phe*-Z-Phe-Z-PheL- | II*-13 |
| -Phe-Z-Phe*-Z-PheL- | II*-14 |
| -Phe*-Z-PheL-Z-Phe- | II*-15 |
| -Phe*L-Z-Phe-Z-Phe- | II*-16 |
| -Phe*L-Z-Phe-Z-PheL- | II*-17 |
| -Phe*L-Z-PheL-Z-Phe- | II*-18 |
| -Phe*L-Z-PheL-Z-PheL- | II*-19 |
| -Phe*-Z-PheL-Z-Cyc- | II*-20 |
| -Phe*-Z-Cyc-Z-PheL- | II-21 |
| -Cyc-Z-Phe*-Z-PheL- | II*-22 |
| -Phe*L-Z-Cyc-Z-PheL- | II*-23 |
| -Phe*L-Z-PheL-Z-Cyc- | II*-24 |
| -Phe*L-Z-Cyc-Z-Cyc- | II*-25 |
| -Cyc-Z-Phe*L - | II*-26 |

$MG^{12}$ is selected from the group consisting of formulae II-0, II-0', II-1, II-2 and II-4 to II-26 and their mirror images

| | |
|---|---|
| -Phe- | II-0 |
| -PheL- | II-0' |
| -Phe-Z-Phe- | II-1 |
| -Phe-Z-Cyc- | II-2 |
| -Phe-Z-PheL- | II-4 |
| -PheL-Z-Phe- | II-5 |
| -PheL-Z-Cyc- | II-6 |
| -PheL-Z-PheL- | II-7 |
| -Phe-Z-Phe-Z-Phe- | II-8 |
| -Phe-Z-Phe-Z-Cyc- | II-9 |
| -Phe-Z-Cyc-Z-Phe- | II-10 |
| - Cyc-Z-Phe-Z-Cyc- | II-11 |
| -Phe-Z-Cyc-Z-Cyc- | II-12 |
| -Cyc-Z-Cyc-Z-Cyc- | II-13 |
| -Phe-Z-Phe-Z-PheL- | II-14 |
| -Phe-Z-PheL-Z-Phe- | II-15 |
| -PheL-Z-Phe-Z-Phe- | II-16 |
| -PheL-Z-Phe-Z-PheL- | II-17 |
| -PheL-Z-PheL-Z-Phe- | II-18 |
| -PheL-Z-PheL-Z-PheL- | II-19 |
| -Phe-Z-PheL-Z-Cyc- | II-29 |
| -Phe-Z-Cyc-Z-PheL- | II-21 |
| -Cyc-Z-Phe-Z-PheL- | II-22 |
| - PheL-Z-Cyc-Z-PheL- | II-23 |
| -PheL-Z-PheL-Z-Cyc- | II-24 |
| -PheL-Z-Cyc-Z-Cyc- | II-25 |
| -Cyc-Z-PheL-Z-Cyc- | II-26 |

Cyc is 1,4-cyclohexylene,
Phe* is 1,3-phenylene or alkyl-1,3-phenylene,
Phe is 1,4-phenylene or alkyl-1,4-phenylene,
Phe*L is 1,3-phenylene, which is substituted by one, two or three fluorine atoms, by one or two Cl atoms or by one Cl atom and one F atom,
PheL in $MG^{11}$ is 1,4-phenylene, which is substituted by one, two or three fluorine atoms, by one or two Cl atoms or by one Cl atom and one F atom,
Z in $MG^{11}$ is —COO—, —OCO—, —O—CO—O—, —OCH$_2$—, —CH$_2$O—, —OCF$_2$—, —CF$_2$O—, —CH$_2$CH$_2$—, —(CH$_2$)$_4$—, —CF$_2$CF$_2$—, —CH=CH—, —CF=CF—, —CH=CH—COO—, —OCO—CH=CH— or —C≡C—, optionally substituted with one or more of F,
PheL in $MG^{12}$ is 1,4-phenylene, which is substituted by one, two or three fluorine atoms, by one or two Cl atoms, by one Cl atom and one F atom or by one alkyl or alkoxy group having 1 to 9 C-atoms,
Z in $MG^{12}$ is a single bond, —COO—, —OCO—, —O—CO—O—, —OCH$_2$—, —CH$_2$O—, —OCF$_2$—, —CF$_2$O—, —CH$_2$CH$_2$—, —(CH$_2$)$_4$—, —CF$_2$CF$_2$—, —CH=CH—, —CF=CF—, —CH=CH—COO—, —OCO—CH=CH— or —C≡C—, optionally substituted with one or more of F, S and/or Si,
$Sp^1$ is a spacer group comprising 1, 2, 3, 4 or 5 to 40 C atoms, wherein one or more non-adjacent and non-terminal CH$_2$ groups are optionally replaced by —O—, —S—, —NH—, —N(CH$_3$)—, —CO—, —O—CO—, —S—CO—, —O—COO—, —CO—S—, —CO—O—, —CH(halogen)-, —CH(CN)—, —CH=CH— or —C≡C—, wherein one or more H atoms in —CH$_2$—groups are independently of each other optionally replaced by F or CH$_3$, and
$X^{11}$ and $X^{12}$ are each independently of one another —CH=CH—, —C≡C—, —, —CF$_2$—O—, —O—CF$_2$—, —CO—O—, —O—CO—, —O—CO—O—, —S—, —CS—S—, —S—CS—, —CO—S—, —S—CO—, —S—CO—S—, —S—CS—S— or a single bond,
under the condition that in —$X^{11}$- $sp^1$-$X^{12}$ — no two O-atoms are adjacent to one another, no two —CH=CH—groups are adjacent to each other and no two groups selected from the group consisting of —O—CO—, —S—CO—, —O—COO—, —CO—S—, —CO—O— and —CH=CH— are adjacent to each other.

15. The compound according to claim 14, wherein $R^{11}$ and $R^{12}$ are independently of one another selected from the group consisting of $OCF_3$, $CF_3$, F, Cl and CN.

16. The compound according to claim 14, wherein $Sp^1$ is —$(CH_2)_o$— and o is 1, 3 or an integer from 5 to 15.

17. A liquid-crystalline medium, comprising one or more compounds according to claim 14.

18. The compound according to claim 14, wherein
$R^{11}$ is F, Cl, CN, NCS or a straight-chain or branched alkyl group with 1 to 25 C atoms which is unsubstituted, mono- or polysubstituted by halogen or CN, in which optionally one or more non-adjacent $CH_2$ groups are replaced, in each occurrence independently from one another, by —O—, —S—, —NH—, —N($CH_3$)—, —CO—, —COO—, —OCO—, —O—CO—O—, —S—CO—, —CO—S—, —CH=CH—, —CH=CF—, —CF=CF— or —C≡C—.

19. A liquid crystal flexoelectric device comprising a liquid crystalline medium comprising two or more components, one or more of which is a compound of formula I according to claim 14.

20. A liquid-crystalline medium, comprising one or more compounds of formula I and one or more liquid-crystalline compounds that are not of formula I

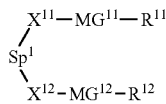   I where
$R^{11}$ and $R^{12}$ are each independently H, F, Cl, CN, NCS or a straight-chain or branched alkyl group with 1 to 25 C atoms which is unsubstituted, mono- or polysubstituted by halogen or CN, in which optionally one or more non-adjacent $CH_2$ groups are replaced, in each occurrence independently from one another, by —O—, —S—, —NH—, —N($CH_3$)—, —CO—, —COO—, —OCO—, —O—CO—O—, —S—CO—, —CO—S—, —CH=CH—, —CH=CF—, —CF=CF— or —C≡C—, $MG^{11}$ is of formula II*,

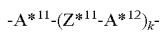   II*

$Z^{*11}$ is a single bond, —COO—, —OCO—, —O—CO—O—, —OCH_2—, —CH_2O—, —OCF_2—, —CF_2O—, —CH_2CH_2—, —(CH_2)_4—, —CF_2CF_2—, —CH=CH—, —CF=CF—, —CH=CH—COO—, —OCO—CH=CH— or —C≡C—, optionally substituted with one or more of F, S and/or Si, one of $A^{*11}$ and $A^{*12}$ present in $MG^{11}$ is 1,3-phenylene, wherein optionally one or two non-adjacent CH groups each are optionally replaced by an N-atom, and which optionally is substituted by one or more halogen atoms and/or by one or more alkyl group(s) each independently having 1 to 9 C atoms, and/or by one more alkoxy group(s) each independently having 1 to 9 C atoms, the other of $A^{*11}$ and $A^{*12}$ present in $MG^{11}$ is 1,4-phenylene, wherein one or more CH groups are optionally replaced by N, trans-1,4-cyclo-hexylene in which, one or two non-adjacent $CH_2$ groups are optionally replaced by O and/or S, 1,4-cyclohexenylene, 1,4-bicyclo-(2,2,2)-octylene, piperidine-1,4-diyl, naphthalene-2,6-diyl, deca-hydro-naphthalene-2,6-diyl, 1,2,3,4-tetrahydro-naphthalene-2,6-diyl, cyclobutane-1,3-diyl, spiro[3.3]heptane-2,6-diyl or dispiro[3.1.3.1] decane-2,8-diyl, wherein all these groups are unsubstituted, mono-, di-, tri- or tetrasubstituted with F, Cl, CN or alkyl, alkoxy, alkylcarbonyl or alkoxycarbonyl groups with 1 to 7 C atoms, wherein one or more H atoms are optionally substituted by F or Cl, k is 0, 1, 2, 3 or 4, $Sp^1$ is a spacer group comprising 1, 2, 3, 4 or 5 to 40 C atoms, wherein one or more non-adjacent and non-terminal $CH_2$ groups are optionally replaced by —O—, —S—, —NH—, —N($CH_3$)—, —CO—, —O—CO—, —S—CO—, —O—COO—, —CO—S—, —CO—O—, —CH(halogen)-, —CH(CN)—, —CH=CH— or —C≡C—, wherein one or more H atoms in —$CH_2$— groups are independently of each other optionally replaced by F or $CH_3$, and $X^{11}$ and $X^{12}$ are each independently of one another —CH=CH—, —C≡C—, —O—, —$CF_2$—O—, —O—$CF_2$—, —CO—O—, —O—CO—, —O—CO—O—, —S—, —CS—S—, —S—CS—, —CO—S—, —S—CO—, —S—CO—S—, —S—CS—S— or a single bond, $MG^{12}$ is selected from the group consisting of formulae II-0, II-0', II-1, II-2 and II-4 to II-26 and their mirror images

| | |
|---|---|
| -Phe- | II-0 |
| -PheL- | II-0' |
| -Phe-Z-Phe- | II-1 |
| -Phe-Z-Cyc- | II-2 |
| -Phe-Z-PheL- | II-4 |
| -PheL-Z-Phe- | II-5 |
| -PheL-Z-Cyc- | II-6 |
| -PheL-Z-PheL- | II-7 |
| -Phe-Z-Phe-Z-Phe- | II-8 |
| -Phe-Z-Phe-Z-Cyc- | II-9 |
| -Phe-Z-Cyc-Z-Phe- | II-10 |
| -Cyc-Z-Phe-Z-Cyc- | II-11 |
| -Phe-Z-Cyc-Z-Cyc- | II-12 |
| Cyc-Z-Cyc-Z-Cyc- | II-13 |
| -Phe-Z-Phe-Z-PheL- | II-14 |
| -Phe-Z-PheL-Z-Phe- | II-15 |
| -PheL-Z-Phe-Z-Phe- | II-16 |
| -PheL-Z-Phe-Z-PheL- | II-17 |
| -PheL-Z-PheL-Z-Phe- | II-18 |
| -PheL-Z-PheL-Z-PheL- | II-19 |
| -Phe-Z-PheL-Z-Cyc- | II-29 |
| -Phe-Z-Cyc-Z-PheL- | II-21 |

| | |
|---|---|
| Cyc-Z-Phe-Z-PheL- | II-22 |
| -PheL-Z-Cyc-Z-PheL- | II-23 |
| -PheL-Z-PheL-Z-Cyc- | II-24 |
| -PheL-Z-Cyc-Z-Cyc- | II-25 |
| Cyc-Z-PheL-Z-Cyc- | II-26 |

Cyc is 1,4-cyclohexylene,
Phe is 1,4-phenylene or alkyl-1,4-phenylene,
PheL is 1,4-phenylene, which is substituted by one, two or three fluorine atoms, by one or two Cl atoms, by one Cl atom and one F atom or by one alkyl or alkoxy group having 1 to 9 C—atoms, and
Z is a single bond, —COO—, —OCO—, —O—CO—O—, —OCH$_2$—, —CH$_2$O—, —OCF$_2$—, —CF$_2$O—, —CH$_2$CH$_2$—, —(CH$_2$)$_4$—, —CF$_2$CF$_2$—, —CH=CH—, —CF=CF—, —CH=CH—COO—, —OCO—CH=CH— or —C≡C—, optionally substituted with one or more of F, S and/or Si,
under the condition that in —X$^{11}$-Sp$^1$-X$^{12}$— no two O-atoms are adjacent to one another, no two —CH=CH—groups are adjacent to each other and no two groups selected from the group consisting of —O—CO—, —S—CO—, —O—COO—, —CO—S—, —CO—O— and —CH=CH— are adjacent to each other.

* * * * *